US009012427B2

(12) United States Patent
Blatt et al.

(10) Patent No.: US 9,012,427 B2
(45) Date of Patent: Apr. 21, 2015

(54) PHARMACEUTICAL COMBINATIONS COMPRISING A THIONUCLEOTIDE ANALOG

(71) Applicants: Alios BioPharma, Inc., South San Francisco, CA (US); Vertex Pharmaceuticals Inc., Cambridge, MA (US)

(72) Inventors: Lawrence M Blatt, Healdsburg, CA (US); Leonid Beigelman, San Mateo, CA (US); Hua Tan, Daly City, CA (US); Julian Alexander Symons, San Carlos, CA (US); David Bernard Smith, San Mateo, CA (US); Min Jiang, Lexington, MA (US); Tara Lynn Kieffer, Brookline, MA (US); Cornelis Arie Rijnbrand, Jamaica Plain, MA (US)

(73) Assignee: Alios BioPharma, Inc., South San Francisco, CA (US)

( * ) Notice: Subject to any disclaimer, the term of this patent is extended or adjusted under 35 U.S.C. 154(b) by 29 days.

(21) Appl. No.: 13/797,511

(22) Filed: Mar. 12, 2013

(65) Prior Publication Data
US 2013/0252920 A1 Sep. 26, 2013

Related U.S. Application Data

(60) Provisional application No. 61/613,854, filed on Apr. 19, 2012, provisional application No. 61/614,494, filed on Mar. 22, 2012.

(51) Int. Cl.
*A01N 43/04* (2006.01)
*A61K 31/70* (2006.01)
*A61K 31/7072* (2006.01)
*A61K 31/4709* (2006.01)
*A61K 31/4178* (2006.01)
*A61K 31/497* (2006.01)
*A61K 31/381* (2006.01)
*A61K 38/55* (2006.01)

(52) U.S. Cl.
CPC ......... *A61K 31/7072* (2013.01); *A61K 31/4709* (2013.01); *A61K 31/4178* (2013.01); *A61K 31/497* (2013.01); *A61K 31/381* (2013.01); *A61K 38/55* (2013.01)

(58) Field of Classification Search
None
See application file for complete search history.

(56) References Cited

U.S. PATENT DOCUMENTS

| | | |
|---|---|---|
| 2,844,579 A | 7/1958 | Turner et al. |
| 3,180,859 A | 4/1965 | Hoeksema |
| 3,431,252 A | 3/1969 | Walton |
| 3,816,399 A | 6/1974 | Shaw et al. |
| 3,872,084 A | 3/1975 | Jones et al. |
| 3,872,098 A | 3/1975 | Jones et al. |
| 4,093,714 A | 6/1978 | Tolman et al. |
| 4,808,614 A | 2/1989 | Hertel |
| 5,378,825 A | 1/1995 | Cook et al. |
| 5,432,272 A | 7/1995 | Benner |
| 5,552,311 A | 9/1996 | Sorscher et al. |
| 5,578,718 A | 11/1996 | Cook et al. |
| 5,580,967 A | 12/1996 | Joyce |
| 5,602,240 A | 2/1997 | De Mesmaeker et al. |
| 5,610,289 A | 3/1997 | Cook et al. |
| 5,616,488 A | 4/1997 | Sullivan et al. |
| 5,620,676 A | 4/1997 | Jacobson et al. |
| 5,625,056 A | 4/1997 | Genieser et al. |
| 5,631,359 A | 5/1997 | Chowrira et al. |
| 5,631,360 A | 5/1997 | Usman et al. |
| 5,639,647 A | 6/1997 | Usman et al. |
| 5,646,128 A | 7/1997 | Firestein et al. |
| 5,658,780 A | 8/1997 | Stinchcomb et al. |
| 5,677,437 A | 10/1997 | Teng et al. |
| 5,681,940 A | 10/1997 | Wang et al. |
| 5,686,599 A | 11/1997 | Tracz |
| 5,693,532 A | 12/1997 | McSwiggen et al. |
| 5,714,383 A | 2/1998 | Thompson |
| 5,721,350 A | 2/1998 | Chattopadhyaya |
| 5,728,684 A | 3/1998 | Cheng et al. |
| 5,744,595 A | 4/1998 | Srivastava et al. |
| 5,767,097 A | 6/1998 | Tam |
| 5,783,425 A | 7/1998 | Dudycz et al. |
| 5,804,683 A | 9/1998 | Usman et al. |
| 5,807,718 A | 9/1998 | Joyce et al. |
| 5,811,300 A | 9/1998 | Sullivan et al. |
| 5,831,071 A | 11/1998 | Usman et al. |

(Continued)

FOREIGN PATENT DOCUMENTS

| | | |
|---|---|---|
| CA | 2252144 | 4/2000 |
| CN | 1290707 A | 12/2001 |

(Continued)

OTHER PUBLICATIONS

Aivazashvili et al., Use of 5'-C-methylnucleoside triphosphates in the synthesis of RNA catalyzed by RNA-polymerase of *Escherichia coli*, MOLBBJ, 1987, vol. 21, Issue 4, pp. 898-908.
Aivasashvilli et al., Utilization of 5'-C-methylnucleoside triphosphates in RNA synthesis reaction catalyzed by *Escherichia coli* RNA-polymerase, Molekulyarnaya Biologiya (Moscow), 1987, vol. 21, Issue 4, pp. 1080-1091.
Aspelund et al., 5-Isopropyl- and 5-propyl-1-methyl-3-phenyldialuric acids, Acta Acad. Aboensis, Math. & Phys., 1958, vol. 21, Issue 11, pp. 3-11.

(Continued)

*Primary Examiner* — Patrick Lewis
(74) *Attorney, Agent, or Firm* — Knobbe Martens Olson & Bear LLP

(57) ABSTRACT

Disclosed herein are pharmaceutical compositions that can include a thionucleotide analog for use in combination therapy with other agents. Also disclosed herein are methods of treating diseases and/or conditions with a pharmaceutical composition that can include a thionucleotide analog in combination therapy with other agents.

41 Claims, 12 Drawing Sheets

(56) References Cited

U.S. PATENT DOCUMENTS

| | | |
|---|---|---|
| 5,837,542 A | 11/1998 | Grimm et al. |
| 5,837,855 A | 11/1998 | Chowrira et al. |
| 5,871,918 A | 2/1999 | Thorp et al. |
| 5,892,024 A | 4/1999 | Chaturvedula et al. |
| 5,902,880 A | 5/1999 | Thompson |
| 5,952,478 A | 9/1999 | Baxter et al. |
| 5,965,721 A | 10/1999 | Cook et al. |
| 5,968,745 A | 10/1999 | Thorp et al. |
| 5,977,343 A | 11/1999 | Tracz |
| 5,985,621 A | 11/1999 | Usman et al. |
| 6,004,939 A | 12/1999 | Chen et al. |
| 6,017,896 A | 1/2000 | Sorscher et al. |
| 6,022,962 A | 2/2000 | Chowrira et al. |
| 6,030,957 A | 2/2000 | Uckun et al. |
| 6,063,566 A | 5/2000 | Joyce |
| 6,063,628 A | 5/2000 | Loeb et al. |
| 6,087,482 A | 7/2000 | Teng et al. |
| 6,130,326 A | 10/2000 | Ramasamy et al. |
| 6,132,971 A | 10/2000 | Thorp et al. |
| 6,156,501 A | 12/2000 | McGall et al. |
| 6,191,266 B1 | 2/2001 | Wang |
| 6,232,463 B1 | 5/2001 | Cook et al. |
| 6,326,174 B1 | 12/2001 | Joyce et al. |
| 6,353,098 B1 | 3/2002 | Usman et al. |
| 6,361,951 B1 | 3/2002 | Thorp et al. |
| 6,365,374 B1 | 4/2002 | Usman et al. |
| 6,437,117 B1 | 8/2002 | Usman et al. |
| 6,440,705 B1 | 8/2002 | Stanton, Jr. et al. |
| 6,455,513 B1 | 9/2002 | McGuigan et al. |
| 6,458,945 B1 | 10/2002 | Stanton, Jr. et al. |
| 6,469,158 B1 | 10/2002 | Usman et al. |
| 6,482,932 B1 | 11/2002 | Beigelman et al. |
| 6,491,905 B1 | 12/2002 | Sorscher et al. |
| 6,495,677 B1 | 12/2002 | Ramasamy et al. |
| 6,503,890 B1 | 1/2003 | Uckun |
| 6,528,640 B1 | 3/2003 | Beigelman et al. |
| 6,552,183 B1 | 4/2003 | Ramasamy et al. |
| 6,566,059 B1 | 5/2003 | Stanton, Jr. et al. |
| 6,569,630 B1 | 5/2003 | Vivekananda et al. |
| 6,573,248 B2 | 6/2003 | Ramasamy et al. |
| 6,582,923 B2 | 6/2003 | Stanton, Jr. et al. |
| 6,589,941 B1 | 7/2003 | Fahrig et al. |
| 6,596,700 B2 | 7/2003 | Sommadossi et al. |
| 6,617,438 B1 | 9/2003 | Beigelman et al. |
| 6,642,206 B2 | 11/2003 | Ramasamy et al. |
| 6,649,750 B1 | 11/2003 | Capaldi et al. |
| 6,649,751 B2 | 11/2003 | Usman et al. |
| 6,670,461 B1 | 12/2003 | Wengel et al. |
| 6,677,314 B2 | 1/2004 | Klecker et al. |
| 6,677,315 B2 | 1/2004 | Klecker et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,161 B2 | 8/2004 | Ismaili et al. |
| 6,787,526 B1 | 9/2004 | Bryant et al. |
| 6,794,499 B2 | 9/2004 | Wengel et al. |
| 6,812,219 B2 | 11/2004 | LaColla et al. |
| 6,815,542 B2 | 11/2004 | Hong et al. |
| 6,831,069 B2 | 12/2004 | Tam et al. |
| 6,875,752 B2 | 4/2005 | Aszodi et al. |
| 6,887,707 B2 | 5/2005 | Loeb et al. |
| 6,914,054 B2 | 7/2005 | Sommadossi et al. |
| 6,958,318 B2 | 10/2005 | Sorscher et al. |
| 6,974,865 B2 | 12/2005 | Cook et al. |
| 6,995,148 B2 | 2/2006 | Jones et al. |
| 7,018,989 B2 | 3/2006 | McGuigan et al. |
| 7,034,133 B2 | 4/2006 | Wengel et al. |
| 7,037,718 B2 | 5/2006 | Ealick et al. |
| 7,041,817 B2 | 5/2006 | Usman et al. |
| 7,049,068 B2 | 5/2006 | Thorp et al. |
| 7,064,114 B2 | 6/2006 | Yiv et al. |
| 7,081,449 B2 | 7/2006 | Pietrzkowski et al. |
| 7,091,315 B1 | 8/2006 | Ruben et al. |
| 7,094,768 B2 | 8/2006 | Roberts et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,112,406 B2 | 9/2006 | Behlke et al. |
| 7,125,855 B2 | 10/2006 | Bhat et al. |
| 7,138,501 B2 | 11/2006 | Ruben et al. |
| 7,141,574 B2 | 11/2006 | Beaulieu et al. |
| 7,141,665 B1 | 11/2006 | Joyce et al. |
| 7,148,206 B2 | 12/2006 | Sommadossi et al. |
| 7,151,089 B2 | 12/2006 | Roberts et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,235,649 B2 | 6/2007 | Gewirth et al. |
| 7,268,119 B2 | 9/2007 | Cook et al. |
| 7,285,658 B2 | 10/2007 | Cook et al. |
| 7,335,648 B2 | 2/2008 | Plourde, Jr. et al. |
| 7,339,054 B2 | 3/2008 | Xu et al. |
| 7,351,841 B2 | 4/2008 | Owada et al. |
| 7,365,057 B2 | 4/2008 | LaColla et al. |
| 7,368,438 B2 | 5/2008 | Plourde, Jr. et al. |
| 7,378,402 B2 | 5/2008 | Martin |
| 7,384,924 B2 | 6/2008 | LaColla et al. |
| 7,407,965 B2 | 8/2008 | Chen et al. |
| 7,427,636 B2 | 9/2008 | Cannizzaro et al. |
| 7,429,565 B2 | 9/2008 | Boojamra et al. |
| 7,432,261 B2 | 10/2008 | Cannizzaro et al. |
| 7,452,901 B2 | 11/2008 | Boojamra et al. |
| 7,470,724 B2 | 12/2008 | Cannizzaro et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,625,875 B2 | 12/2009 | Gosselin et al. |
| 7,629,328 B2 | 12/2009 | Roberts et al. |
| 7,635,689 B2 | 12/2009 | LaColla et al. |
| 7,645,747 B2 | 1/2010 | Boojamra et al. |
| 7,713,941 B2 | 5/2010 | Cook et al. |
| 7,718,790 B2 | 5/2010 | Stuyver et al. |
| 7,749,983 B2 | 7/2010 | Hostetler et al. |
| 7,953,557 B2 | 5/2011 | Johnson et al. |
| 2001/0011075 A1 | 8/2001 | Townsend et al. |
| 2002/0132237 A1 | 9/2002 | Algate et al. |
| 2002/0150922 A1 | 10/2002 | Stolk et al. |
| 2003/0004122 A1 | 1/2003 | Beigelman et al. |
| 2003/0008841 A1 | 1/2003 | Devos et al. |
| 2003/0050320 A1 | 3/2003 | Hashimoto et al. |
| 2003/0073144 A1 | 4/2003 | Benson et al. |
| 2003/0144489 A1 | 7/2003 | Burgin et al. |
| 2003/0166064 A1 | 9/2003 | King et al. |
| 2003/0170891 A1 | 9/2003 | McSwiggen |
| 2003/0207271 A1 | 11/2003 | Holwitt |
| 2004/0009491 A1 | 1/2004 | Birse |
| 2004/0023265 A1 | 2/2004 | Vivekananda et al. |
| 2004/0023266 A1 | 2/2004 | Vivekananda et al. |
| 2004/0063658 A1 | 4/2004 | Roberts et al. |
| 2004/0077585 A1 | 4/2004 | Peterson et al. |
| 2004/0082635 A1 | 4/2004 | Hashimoto et al. |
| 2004/0127436 A1 | 7/2004 | Daifuku et al. |
| 2004/0171028 A1 | 9/2004 | Baker et al. |
| 2004/0171032 A1 | 9/2004 | Baker et al. |
| 2004/0229839 A1 | 11/2004 | Babu et al. |
| 2004/0259934 A1 | 12/2004 | Olsen et al. |
| 2005/0031588 A1 | 2/2005 | Sommadossi et al. |
| 2005/0032067 A1 | 2/2005 | Prakash et al. |
| 2005/0042632 A1 | 2/2005 | Radka |
| 2005/0042647 A1 | 2/2005 | Baker et al. |
| 2005/0186568 A1 | 8/2005 | Bandman et al. |
| 2005/0203044 A1 | 9/2005 | Zinnen |
| 2005/0214901 A1 | 9/2005 | Ealick et al. |
| 2005/0233358 A1 | 10/2005 | Thorp et al. |
| 2005/0239733 A1 | 10/2005 | Jurk et al. |
| 2005/0245463 A1 | 11/2005 | Pham et al. |

(56) References Cited

U.S. PATENT DOCUMENTS

| | | |
|---|---|---|
| 2005/0256073 A1 | 11/2005 | Lipford |
| 2005/0261237 A1 | 11/2005 | Boojamra et al. |
| 2006/0003952 A1 | 1/2006 | Ravikumar et al. |
| 2006/0014689 A1 | 1/2006 | Vesely |
| 2006/0058254 A1 | 3/2006 | Dina et al. |
| 2006/0074035 A1 | 4/2006 | Hong et al. |
| 2006/0094678 A1 | 5/2006 | Vornlocher et al. |
| 2006/0100166 A1 | 5/2006 | De Koning et al. |
| 2006/0105976 A1 | 5/2006 | Soutschek et al. |
| 2006/0121086 A1 | 6/2006 | Boyer et al. |
| 2006/0122146 A1 | 6/2006 | Chun et al. |
| 2006/0142238 A1 | 6/2006 | McGuigan |
| 2006/0193869 A1 | 8/2006 | Barrat et al. |
| 2006/0217330 A1 | 9/2006 | Hartmann et al. |
| 2006/0229265 A1 | 10/2006 | Milburn et al. |
| 2006/0240462 A1 | 10/2006 | Todd et al. |
| 2006/0264404 A1 | 11/2006 | Boojamra et al. |
| 2006/0269517 A1 | 11/2006 | Blatt et al. |
| 2006/0287260 A1 | 12/2006 | Manoharan et al. |
| 2007/0027116 A1 | 2/2007 | Cho et al. |
| 2007/0032448 A1 | 2/2007 | Hong et al. |
| 2007/0037773 A1 | 2/2007 | Sommadossi et al. |
| 2007/0042350 A1 | 2/2007 | Li et al. |
| 2007/0042988 A1 | 2/2007 | Klumpp et al. |
| 2007/0066552 A1 | 3/2007 | Clarke et al. |
| 2007/0093446 A1 | 4/2007 | Douglass, III et al. |
| 2007/0105122 A1 | 5/2007 | Ota et al. |
| 2007/0105806 A1 | 5/2007 | Sah et al. |
| 2007/0123544 A1 | 5/2007 | Plourde, Jr. et al. |
| 2007/0135372 A1 | 6/2007 | MacLachlan et al. |
| 2007/0196824 A1 | 8/2007 | Stuyver et al. |
| 2007/0197463 A1 | 8/2007 | Chun et al. |
| 2007/0207973 A1 | 9/2007 | Daifuku et al. |
| 2007/0213292 A1 | 9/2007 | Stoffel et al. |
| 2007/0219365 A1 | 9/2007 | Joyce et al. |
| 2007/0231810 A1 | 10/2007 | Todd et al. |
| 2007/0238099 A1 | 10/2007 | Cohen et al. |
| 2007/0238678 A1 | 10/2007 | Barrat et al. |
| 2007/0258921 A1 | 11/2007 | Dalko |
| 2007/0259832 A1 | 11/2007 | Cook et al. |
| 2007/0265224 A1 | 11/2007 | Cook et al. |
| 2007/0275912 A1 | 11/2007 | Bhat et al. |
| 2007/0281899 A1 | 12/2007 | Bumcrot et al. |
| 2007/0299068 A1 | 12/2007 | Karp et al. |
| 2008/0009462 A1 | 1/2008 | Hostetler et al. |
| 2008/0015161 A1 | 1/2008 | Vornlocher et al. |
| 2008/0026362 A1 | 1/2008 | Ho et al. |
| 2008/0027068 A1 | 1/2008 | Owada et al. |
| 2008/0064753 A1 | 3/2008 | Palladino et al. |
| 2008/0070935 A1 | 3/2008 | Huang et al. |
| 2008/0152621 A1 | 6/2008 | Johansson et al. |
| 2008/0161246 A1 | 7/2008 | Klein et al. |
| 2008/0161324 A1 | 7/2008 | Johansen et al. |
| 2008/0199870 A1 | 8/2008 | Guenther et al. |
| 2008/0200423 A1 | 8/2008 | Cook et al. |
| 2008/0207542 A1 | 8/2008 | McSwiggen et al. |
| 2008/0207554 A1 | 8/2008 | Beigelman et al. |
| 2008/0261913 A1 | 10/2008 | Sommadossi et al. |
| 2008/0286230 A1 | 11/2008 | Sommadossi et al. |
| 2008/0293665 A1 | 11/2008 | Undheim et al. |
| 2009/0131372 A1 | 5/2009 | Chen et al. |
| 2009/0169504 A1 | 7/2009 | Sommadossi et al. |
| 2009/0176732 A1 | 7/2009 | Beigelman et al. |
| 2009/0181921 A1 | 7/2009 | Blatt et al. |
| 2009/0220950 A1 | 9/2009 | Stuyver et al. |
| 2009/0221684 A1 | 9/2009 | Grinstaff et al. |
| 2009/0227543 A1 | 9/2009 | Cannizzaro et al. |
| 2009/0233872 A1 | 9/2009 | Ariga et al. |
| 2009/0238790 A2 | 9/2009 | Sommadossi et al. |
| 2009/0247488 A1 | 10/2009 | Cannizzaro et al. |
| 2009/0275535 A1 | 11/2009 | Boojamra et al. |
| 2009/0280084 A1 | 11/2009 | Schinazi et al. |
| 2009/0280086 A1 | 11/2009 | Sommadossi et al. |
| 2009/0318380 A1 | 12/2009 | Sofia et al. |
| 2010/0016251 A1 | 1/2010 | Sofia et al. |
| 2010/0022467 A1 | 1/2010 | Boojamra et al. |
| 2010/0035835 A1 | 2/2010 | Narjes et al. |
| 2010/0081628 A1 | 4/2010 | Du et al. |
| 2010/0093656 A1 | 4/2010 | Adelfinskaya et al. |
| 2010/0137237 A1 | 6/2010 | Undheim et al. |
| 2010/0137576 A1 | 6/2010 | Stec et al. |
| 2010/0152128 A1 | 6/2010 | Attenni et al. |
| 2010/0249068 A1 | 9/2010 | Beigelman et al. |
| 2010/0297079 A1 | 11/2010 | Almond et al. |
| 2010/0305060 A1 | 12/2010 | Hecker et al. |
| 2010/0311684 A1 | 12/2010 | Cook et al. |
| 2010/0331397 A1 | 12/2010 | Beigelman et al. |
| 2011/0015383 A1 | 1/2011 | Stec et al. |
| 2012/0070411 A1 | 3/2012 | Beigelman et al. |
| 2012/0070415 A1 | 3/2012 | Beigelman et al. |
| 2012/0071434 A1* | 3/2012 | Smith et al. ............ 514/48 |
| 2012/0108533 A1 | 5/2012 | Herdewijn et al. |
| 2012/0165286 A1 | 6/2012 | Beigelman et al. |
| 2013/0017171 A1 | 1/2013 | Sommadossi et al. |
| 2013/0149283 A1 | 6/2013 | Sommadossi et al. |
| 2013/0164261 A1 | 6/2013 | Wang et al. |
| 2013/0165400 A1 | 6/2013 | Beigelman et al. |
| 2013/0252920 A1 | 9/2013 | Blatt et al. |
| 2013/0253181 A1 | 9/2013 | Serebryany et al. |
| 2013/0281687 A1 | 10/2013 | Serebryany et al. |
| 2013/0315862 A1 | 11/2013 | Sommadossi et al. |
| 2013/0315863 A1 | 11/2013 | Sommadossi et al. |
| 2014/0179627 A1 | 6/2014 | Beigelman et al. |
| 2014/0179910 A1 | 6/2014 | Beigelman et al. |

FOREIGN PATENT DOCUMENTS

| | | |
|---|---|---|
| CN | 1337401 A | 2/2002 |
| CN | 1343673 A | 4/2002 |
| CN | 101108870 A | 1/2008 |
| DE | 3824110 A1 | 1/1990 |
| DE | 279247 A1 | 5/1990 |
| DE | 4341161 A1 | 6/1995 |
| EP | 0547008 A1 | 6/1993 |
| EP | 0629633 A2 | 12/1994 |
| EP | 0799834 A1 | 10/1997 |
| EP | 1 256 628 | 11/2002 |
| EP | 0742287 B1 | 1/2006 |
| GB | 1209654 A | 10/1970 |
| GB | 1319303 A | 6/1973 |
| GB | 2136425 | 9/1984 |
| JP | 04-046124 | 2/1992 |
| JP | 06-228186 A | 8/1994 |
| JP | 2006-248949 A | 9/2006 |
| JP | 2006-248975 A | 9/2006 |
| NZ | 216172 | 8/1989 |
| NZ | 224189 | 9/1991 |
| NZ | 226844 | 10/1991 |
| NZ | 231444 | 9/1992 |
| NZ | 505531 | 7/2001 |
| PL | 144471 B1 | 5/1988 |
| WO | WO 84/04748 A1 | 12/1984 |
| WO | WO 88/03147 A1 | 5/1988 |
| WO | WO 91/17159 | 11/1991 |
| WO | WO 92/12718 A1 | 8/1992 |
| WO | WO 92/20822 A1 | 11/1992 |
| WO | WO 94/17803 A1 | 8/1994 |
| WO | WO 94/22890 A1 | 10/1994 |
| WO | WO 95/18139 A1 | 7/1995 |
| WO | WO 96/07666 A1 | 3/1996 |
| WO | WO 96/23506 A1 | 8/1996 |
| WO | WO 96/29336 A1 | 9/1996 |
| WO | WO 96/30383 A1 | 10/1996 |
| WO | WO 97/26270 A2 | 7/1997 |
| WO | WO 98/00434 A1 | 1/1998 |
| WO | WO 98/17679 | 4/1998 |
| WO | WO 99/07733 | 2/1999 |
| WO | WO 99/07734 | 2/1999 |
| WO | WO 99/10365 A2 | 3/1999 |
| WO | WO 99/46362 A1 | 9/1999 |
| WO | WO 99/55857 A2 | 11/1999 |
| WO | WO 00/00501 A1 | 1/2000 |
| WO | WO 00/09543 | 2/2000 |
| WO | WO 00/09558 | 2/2000 |

(56) References Cited

FOREIGN PATENT DOCUMENTS

| | | |
|---|---|---|
| WO | WO 00/14263 A2 | 3/2000 |
| WO | WO 00/56366 A1 | 9/2000 |
| WO | WO 00/06529 | 10/2000 |
| WO | WO 00/59929 | 10/2000 |
| WO | WO 01/27114 A1 | 4/2001 |
| WO | WO 01/47883 | 7/2001 |
| WO | WO 01/49701 A1 | 7/2001 |
| WO | WO 01/68663 A1 | 9/2001 |
| WO | WO 01/72779 A1 | 10/2001 |
| WO | WO 01/85172 | 11/2001 |
| WO | WO 01/90121 A2 | 11/2001 |
| WO | WO 02/03997 A1 | 1/2002 |
| WO | WO 02/06246 | 1/2002 |
| WO | WO 02/18369 | 3/2002 |
| WO | WO 02/22660 A2 | 3/2002 |
| WO | WO 02/26930 A2 | 4/2002 |
| WO | WO 02/29103 A2 | 4/2002 |
| WO | WO 02/057287 | 7/2002 |
| WO | WO 02/057425 | 7/2002 |
| WO | WO 02/060926 | 8/2002 |
| WO | WO 02/069903 A2 | 9/2002 |
| WO | WO 02/088385 A1 | 11/2002 |
| WO | WO 02/090526 A2 | 11/2002 |
| WO | WO 02/092006 | 11/2002 |
| WO | WO 02/096927 A2 | 12/2002 |
| WO | WO 02/097031 A2 | 12/2002 |
| WO | WO 02/098424 | 12/2002 |
| WO | WO 02/100415 A2 | 12/2002 |
| WO | WO 02/100846 | 12/2002 |
| WO | WO 02/100851 | 12/2002 |
| WO | WO 03/000254 | 1/2003 |
| WO | WO 03/010140 | 2/2003 |
| WO | WO 03/016475 A2 | 2/2003 |
| WO | WO 03/016497 A2 | 2/2003 |
| WO | WO 03/016572 A1 | 2/2003 |
| WO | WO 03/019189 A1 | 3/2003 |
| WO | WO 03/026587 | 4/2003 |
| WO | WO 03/029271 A2 | 4/2003 |
| WO | WO 03/031419 A1 | 4/2003 |
| WO | WO 03/035012 A2 | 5/2003 |
| WO | WO 03/035060 | 5/2003 |
| WO | WO 03/038052 A2 | 5/2003 |
| WO | WO 03/039348 A2 | 5/2003 |
| WO | WO 03/039523 A2 | 5/2003 |
| WO | WO 03/042357 A2 | 5/2003 |
| WO | WO 03/051896 A1 | 6/2003 |
| WO | WO 03/054152 A2 | 7/2003 |
| WO | WO 03/054219 A2 | 7/2003 |
| WO | WO 03/062257 A1 | 7/2003 |
| WO | WO 03/062376 A2 | 7/2003 |
| WO | WO 03/062379 A2 | 7/2003 |
| WO | WO 03/062385 A2 | 7/2003 |
| WO | WO 03/062391 A2 | 7/2003 |
| WO | WO 03/063688 A2 | 8/2003 |
| WO | WO 03/072602 A2 | 9/2003 |
| WO | WO 03/072729 A2 | 9/2003 |
| WO | WO 03/072757 A2 | 9/2003 |
| WO | WO 03/076586 A2 | 9/2003 |
| WO | WO 03/077875 A2 | 9/2003 |
| WO | WO 03/083082 A2 | 10/2003 |
| WO | WO 03/083084 A2 | 10/2003 |
| WO | WO 03/083085 A2 | 10/2003 |
| WO | WO 03/087092 | 10/2003 |
| WO | WO 03/087300 A2 | 10/2003 |
| WO | WO 03/090674 A2 | 11/2003 |
| WO | WO 03/093439 A2 | 11/2003 |
| WO | WO 03/094848 A2 | 11/2003 |
| WO | WO 04/001008 A2 | 12/2003 |
| WO | WO 2004/003000 A2 | 1/2004 |
| WO | WO 2004/003162 A2 | 1/2004 |
| WO | WO 2004/009797 A2 | 1/2004 |
| WO | WO 2004/014313 | 2/2004 |
| WO | WO 2004/014852 | 2/2004 |
| WO | WO 2004/026890 A1 | 4/2004 |
| WO | WO 2004/028454 A2 | 4/2004 |
| WO | WO 2004/041924 A2 | 5/2004 |
| WO | WO 2004/050899 A2 | 6/2004 |
| WO | WO 2004/080466 A1 | 9/2004 |
| WO | WO 2004/092161 | 10/2004 |
| WO | WO 2004/092162 | 10/2004 |
| WO | WO 2004/106356 A1 | 12/2004 |
| WO | WO 2005/003766 A2 | 1/2005 |
| WO | WO 2005/007681 | 1/2005 |
| WO | WO 2005/010150 A2 | 2/2005 |
| WO | WO 2005/020885 A2 | 3/2005 |
| WO | WO 2005/028502 | 3/2005 |
| WO | WO 2005/035525 | 4/2005 |
| WO | WO 2005/039552 A2 | 5/2005 |
| WO | WO 2005/040174 A1 | 5/2005 |
| WO | WO 2005/047255 A1 | 5/2005 |
| WO | WO 2005/077966 A2 | 8/2005 |
| WO | WO 2005/077969 | 8/2005 |
| WO | WO 2005/123755 A2 | 12/2005 |
| WO | WO 2006/019831 | 2/2006 |
| WO | WO 2006/034373 A2 | 3/2006 |
| WO | WO 2006/038865 A1 | 4/2006 |
| WO | WO 2006/039488 | 4/2006 |
| WO | WO 2006/062240 A1 | 6/2006 |
| WO | WO 2006/066080 A1 | 6/2006 |
| WO | WO 2006/094347 A1 | 9/2006 |
| WO | WO 2006/105440 A2 | 10/2006 |
| WO | WO 2006/106169 A1 | 10/2006 |
| WO | WO 2006/116512 A1 | 11/2006 |
| WO | WO 2006/119507 A2 | 11/2006 |
| WO | WO 2006/121820 A1 | 11/2006 |
| WO | WO 2006/133326 | 12/2006 |
| WO | WO 2007/006544 A2 | 1/2007 |
| WO | WO 2007/020018 A1 | 2/2007 |
| WO | WO 2007/027248 A2 | 3/2007 |
| WO | WO 2007/028051 A2 | 3/2007 |
| WO | WO 2007/056191 A2 | 5/2007 |
| WO | WO 2007/089731 A2 | 8/2007 |
| WO | WO 2007/149554 A2 | 12/2007 |
| WO | WO 2008/021927 | 2/2008 |
| WO | WO 2008/021928 | 2/2008 |
| WO | WO 2008/021936 | 2/2008 |
| WO | WO 2008/033432 A2 | 3/2008 |
| WO | WO 2008/033466 | 3/2008 |
| WO | WO 2008/039267 A2 | 4/2008 |
| WO | WO 2008/052770 A2 | 5/2008 |
| WO | WO 2008/073661 A2 | 6/2008 |
| WO | WO 2008/083949 A2 | 7/2008 |
| WO | WO 2008/101157 A1 | 8/2008 |
| WO | WO 2008/103276 A2 | 8/2008 |
| WO | WO 2008/104408 A2 | 9/2008 |
| WO | WO 2008/106803 A2 | 9/2008 |
| WO | WO 2008/121634 | 10/2008 |
| WO | WO 2008/144380 | 11/2008 |
| WO | WO 2009/005382 A2 | 1/2009 |
| WO | WO 2009/020825 | 2/2009 |
| WO | WO 2009/020828 | 2/2009 |
| WO | WO 2009/073506 A3 | 6/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/127230 A1 | 10/2009 |
| WO | WO 2009/146123 | 12/2009 |
| WO | WO 2010/017401 | 2/2010 |
| WO | WO 2010/019954 A2 | 2/2010 |
| WO | WO 2010/020786 A1 | 2/2010 |
| WO | WO 2010/030858 | 3/2010 |
| WO | WO 2010/048552 A3 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010/091386 A2 | 8/2010 |
| WO | WO 2010/091413 | 8/2010 |
| WO | WO 2010/096302 | 8/2010 |
| WO | WO 2010/096462 | 8/2010 |
| WO | WO 2010/096777 | 8/2010 |
| WO | WO 2010/0940077 | 8/2010 |
| WO | WO 2010/099527 | 9/2010 |

(56) References Cited

FOREIGN PATENT DOCUMENTS

| WO | WO 2010/108140 A1 | 9/2010 |
|---|---|---|
| WO | WO 2010/111483 | 9/2010 |
| WO | WO 2010/117635 | 10/2010 |
| WO | WO 2010/117704 | 10/2010 |
| WO | WO 2010/0117977 | 10/2010 |
| WO | WO 2010/120621 | 10/2010 |
| WO | WO 2010/120935 | 10/2010 |
| WO | WO 2010/122162 | 10/2010 |
| WO | WO 2010/126967 | 11/2010 |
| WO | WO 2010/132538 | 11/2010 |
| WO | WO 2011/005860 A2 | 1/2011 |
| WO | WO 2011/094489 | 8/2011 |
| WO | WO 2011/156757 A1 | 12/2011 |
| WO | WO 2012/040126 A1 | 3/2012 |
| WO | WO 2012/040127 | 3/2012 |
| WO | WO 2012/088155 A1 | 6/2012 |
| WO | WO 2012/142085 | 10/2012 |
| WO | WO 2013/142124 | 9/2013 |
| WO | WO 2013/142159 | 9/2013 |
| WO | WO 2013/142525 | 9/2013 |
| WO | WO 2014/100498 | 6/2014 |

OTHER PUBLICATIONS

Bajwa et al., Thymidine nucleoside 3',5'-cyclic phosphoramidites and phosphites—configuration at phosphorus in trivalent and pentavalent cyclic nucleotides by phosphorus-31 and carbon-13 NMR, Tetrahedron Letters, 1978, vol. 5, pp. 421-424.

Baker et al., Synthesis of potential anticancer agents. VI. Use of the O-benzoyl blocking group from synthesis of 6-chloropurine nucleosides, Journal of Organic Chemistry, 1957, vol. 22, pp. 954-959.

Baker et al., Synthesis of potential anticancer agents. VII. Nucleosides derived from L-rhamnofuranose, Journal of Organic Chemistry, 1957, vol. 22, pp. 959-966.

Baker et al., Synthesis of potential anticancer agents. VIII. Nucleosides derived from L-rhamnofuranose, Journal of Organic Chemistry, 1957, vol. 22, pp. 966-971.

Baraniak et al., Ribonucleoside cyclic 3',5'-phosphoramidates: Synthesis, stereochemistry, and conversion into ribonucleoside cyclic 3',5'-phosphorothioates and -[180] phosphates, Journal of the Chemical Society, Perkin Transactions 1: Organic and Bio-Organic Chemistry, 1987, vol. 8, pp. 1645-1656.

Baraniak et al., Synthesis of adenosine cyclic 3',5'-phosphorofuoridate (cAMP-F), Tetrahedron Letters, 1995, vol. 36, Issue 44, Elsevier, pp. 8119-8122.

Baraniak, Deoxyribonucleoside cyclic 3',5'-phosphorofluoridates phosphorus, Sulfur Silicon Relat. Elem., 1996, vol. 111, pp. 80.

Beaulieu et al., Inhibitors of the HCV NS5B polymerase: New hope for the treatment of hepatitis C infections, Curr. Opin. Invest. Drugs, 2004, vol. 5, Issue 8, pp. 838-850.

Beigelman et al., Synthesis of 5'-C-methyl-D-allo- & L-talo-ribonucleoside 3'-O-phosphoramidites & their incorporation into hammerhead ribozymes, Nucleosides & Nucleotides, 1995, vol. 14, Issue 5, pp. 901-905.

Bergstrom, Nucleoside phosphorylation and related modifications, Current Protocols in Nucleic Acid Chemistry, Chapter 13, John Wiley & Sons, 2008, Suppl. 33, pp. 13.0.1-13.0.2.

Bennett et al., Designer gene therapy using an *Escherichia coli* purine nucleoside phosphorylase/prodrug system, Chemistry & Biology, 2003, vol. 10, Issue 12, pp. 1173-1181.

Billich et al., Synthesis, conformation and enzymatic properties of 1-(62-D-allofuranosyl) uracil and some derivatives, Nucleic Acids Research, 1983, vol. 11, Issue 21, pp. 7611-7624.

Bindal et al., The relationship of vasodilator activity of adenosine analogs with molecular connectivity and van der Waals volume, Arzneimittel-Forschung, 1980, vol. 30, Issue 6, pp. 924-928.

Botelho et al., Inhibition of cAMP-dependent protein kinase by adenosine cyclic 3',5'-phosphorodithioate, a second cAMP antagonist, Journal of Biological Chemistry, 1988, vol. 263, Issue 11, pp. 5301-5305.

Bottka et al., Evidence for the stereoelectronic control of the acid hydrolysis of adenosine cyclic 3', 5'-phosphoramidate diastereoisomers, Nucleosides & Nucleotides, 1989, vol. 8, Issue 7, pp. 1217-1229.

Bruns, Adenosine receptor activation in human fibroblasts: nucleoside agonists and antagonists, Canadian Journal of Physiology and Pharmacology, 1980, vol. 58, Issue 6, pp. 673-691.

Bundgaard, "Design of prodrugs", Elsevier Science Publishers B.V. (1985), Table of Contents only.

Cahard et al., Aryloxy phosphoramidate triesters as pro-tides, Mini-Reviews in Medicinal Chemistry, 2004, vol. 4, pp. 371-381.

Cappuccino et al., Growth inhibition of clostridium feseri by carcinostatic purine and pyrimidine analogs. I. Effect of medium on growth inhibition, Cancer Research, 1964, vol. 24, pp. 1243-1248.

Carroll et al., Inhibition of hepatitis C virus RNA replication by 2'-modified nucleoside analogs, Journal of Biological Chemistry, 2003, vol. 278, Issue 14, pp. 11979-11984.

Carey, Francis, Organic Chemistry, 2nd ed., McGraw Hill, Inc., New York (1992), pp. 328-331.

CAS RN 486446-48-4, STNEasy, Entry Date Feb. 6, 2003, (https://stneasy.cas.org), retrieved on Nov. 17, 2011.

CASS et al., Mediated transport of nucleosides by human erythrocytes. Specificity toward purine nucleosides as permeants, Biochemica et Biophysica Acta, Biomembranes, 1973, vol. 291, Issue 3, pp. 734-746.

Chidgeavadze et al., Synthesis and substrate properties of C-methyl-2'-deoxynucleoside 5'-triphosphates in DNA synthesis reactions catalyzed by DNA polymerases, Bioorganicheskaya Khimiya, 1991, vol. 17, Issue 5, pp. 678-684.

Chidgeavadze et al., 5'-C- and 3'-C-Methyl-2'-deoxynucleoside 5'-triphosphates and their substrate properties in DNA-polymerase-catalyzed DNA synthesis reactions, Soviet Journal of Bioorganic Chemistry (a translation of Bioorganicheskaya Khimiya), 1992, vol. 17, Issue 5, pp. 389-395.

Cullis, The stereospecific conversion of p-chiral dialkyl phosphorothioates into $^{18}$O-phosphates, Tetrahedron Letters, 1983, vol. 24, Issue 50, pp. 5677-5680.

Cusack et al., Simple syntheses of glycofuranosylamines derived from D-xylose, D-mannose, and L-rhamnose, intermediates in the preparation of some N-glycofuranosyl uracils, Chemical Communications, 1971, vol. 4, pp. 190-191.

David et al., Synthesis of the two epimeric 5'-methylcytidines, their 5'-phosphates and [5-$^3$H]-5'-pyrophosphates, and the two 5'-methyldeoxycytidines. A novel cytosine anhydronucleoside with two oxygen bridges between the base and the sugar, Journal of the Chemical Society, Perkin Transactions 1: Organic and Bio-Organic Chemistry, 1982, vol. 1, pp. 385-393.

De Vroom et al., Synthesis of ribonucleoside 3',5'-cyclic phosphorothioates using a modified hydroxybenzotriazole phosphotriester approach, Recueil des Travaux Chimiques des Pays-Bas, 1987, vol. 106, Issue 11, pp. 577-580.

Del Vecchio et al., Small molecule and biologic inhibitors of hepatitis C virus: A symbiotic approach, Mini-Reviews in Medicinal Chemistry, Nov. 2006, vol. 6, Issue 11, pp. 1263-1268.

Deval et al., Pyrophosphorolytic excision of nonobligate chain terminators by hepatitis C virus NS5B polymerase, Antimicrobial Agents and Chemotherapy, Aug. 2007, vol. 51, Issue 8, pp. 2920-2928.

De Zwart et al., A functional screening of adenosine analogs at the adenosine A2B receptor: A search for potent agonists, Nucleosides & Nucleotides, 1998, vol. 17, Issue 6, pp. 969-985.

Dutartre et al., General catalytic deficiency of hepatitis C virus RNA polymerase with an S282T mutation and mutually exclusive resistance towards 2'-modified nucleotide analogues, Antimicro. Agts. Chemother., 2006, vol. 50, Issue 12, pp. 4161-4169.

Dzhavadova et al., Molecular and crystal structures of 1-(6-desoxy-β-D-allofuranosyl) cytosine and 1-(6-desoxy-α-L-talofuranosyl) cytosine, Sov. Phys. Crystallog., 1988, vol. 33, Issue 6, pp. 837-841.

Dzhavadova et al., The molecular and crystal structures of 1-(6-deoxy-β-D-allofuranosyl) cytosine and 1-(6-deoxy-α-L-talofuranosyl) cytosine, Kristallografiya, 1988, vol. 33, Issue 6, pp. 1408-1414.

(56) References Cited

OTHER PUBLICATIONS

Dzhavadova et al., The molecular and crystal structure of 1-(2, 6-dideoxy-α-L-lyxo-hexofuranosyl) thymine, Bioorganicheskaya Khimiya, 1989, vol. 15, Issue 7, pp. 976-982.
Eliahu, S. et al, A Novel Insulin Secretagogue Based on a Dinucleoside Polyphosphate Scaffold, Journal of Medicinal Chemistry, 2010, vol. 53, No. 6, pp. 2472-2481.
Eppacher et al., Synthesis and incorporation of C(5')-ethynylated uracil-derived phosphoramidites into RNA, Helvetica Chimica Acta, 2004, vol. 87, pp. 3004-3020.
Estrada et al., In silico studies toward the discovery of new anti-HIV nucleoside compounds with the use of TOPS-MODE and 2D/3D connectivity indices. 1. Pyrimidyl derivatives, Journal of Chemical Information and Computer Sciences, 2002, vol. 42, Issue 5, pp. 1194-1203.
Feldwisch et al., Purification & characterization of a cAMP-binding protein of Volvox carteri f. nagariensis iyengar, European Journal of Biochemistry, 1995, vol. 228, Issue 2, pp. 480-489.
Ferrini et al., Free amino acids in the egg of Ciona intestinalis during some development stages, Ricerca Scientifica, Parte 2: Rendiconti, Sezione B: Biologica, 1964, vol. 5, Issue 3, pp. 213-217.
Fingl et al., The Pharmacological Basis of Therapeutics, 5th ed., MacMillan Publishing Co., Inc. (1975) Chapter 1, General Principles, pp. 1-46.
Fischer, B. et al., 2-Thioether 5'-o-(1-Thiotriphosphate)adenosine Derivatives as New Insulin Secretagogues Acting through P2Y-Receptors, Journal of Medicinal Chemistry, 1999, vol. 42, No. 18, pp. 3636-3646.
Follman et al., Novel nucleosides derived from 5'-C-methyl adenosine, Eur. Biophys. Congr., Proc., $1^{st}$, 1971, vol. 1, pp. 285-287.
Follman et al., Adenine nucleosides in solution. Stabilization of the anti-conformation by C-5' substituents, European Journal of Biochemistry, 1974, vol. 47, Issue 1, pp. 187-197.
Follman et al., Adenine nucleosides in solution: Circular dichroism studies and base conformation, European Journal of Biochemistry, 1975, vol. 58, Issue 1, pp. 31-41.
Gangjee et al., Vasodilator activity of adenosine analogs, Journal of Pharmaceutical Sciences, 1978, vol. 67, Issue 1, pp. 121-123.
Gao et al. "Chemical genetics strategy identifies an HCV NS5A inhibitor with a potent clinical effect" Nature (2010) vol. 465, pp. 96-100.
Gardner et al. "Comparative Kinetics of Nucleotide Analog Incorporation by Vent DNA Polymerase" J. Bio. Chem. (2004) 279(12):11834-11842.
Gimisis et al., Tuning the reactivity of O-tert-butyldimethylsilylimidazolyl aminals towards organolithium reagents, Synlett, 2003, vol. 10, pp. 1451-1454.
Girardet et al., Synthesis and cytotoxicity of 4-amino-5-oxopyrido [2, 3-d] pyrimidine nucleosides, Journal of Medicinal Chemistry, 2000, vol. 43, Issue 20, pp. 3704-3713.
Gonzalez et al., A radial distribution function approach to predict A2B agonist effect of adenosine analogues, Bioorganic & Medicinal Chemistry, 2005, vol. 13, Issue 3, pp. 601-608.
Gopalakrishnan et al., A virtual screening approach for thymidine monophosphate kinase inhibitors as antitubercular agents based on docking and pharmacophore models, Journal of Chemical Information and Modeling, 2005, vol. 45, pp. 1101-1108.
Grant et al., Binding specificities of adenosine aminohydrolase from calf intestinal mucosa with dialdehydes derived from hexofuranosyladenine nucleosides, Journal of Medicinal Chemistry, 1980, vol. 23, Issue 1, pp. 39-42.
Grant et al., Hexofuranosyladenine nucleosides as substrates and inhibitors of calf intestinal adenosine deaminase, Journal of Medicinal Chemistry, 1979, vol. 22, Issue 8, pp. 1016-1018.
Greene et al., Protective Groups in Organic Synthesis, 3. Ed., John Wiley & Sons, (1999) Cover & Contents pages.
Greco et al., "The search for synergy: a critical review from a response surface perspective" Pharmacol. Rev. (1995) vol. 47, Issue 2, pp. 331-385.
Gunic et al., Synthesis & cytotoxicity of 4'-C- and 5'-C-substituted toyocamycins, Bioorganic & Medicinal Chemistry, 2001, vol. 9, Issue 1, pp. 163-170.
Gurskaya et al., X-ray crystallographic studies of nucleoside analogs. I. The crystal structure of 1-(6-deoxy-β-D-allofuranosyl) cytosine, $C_{10}H_{15}N_3O_5$, Crystal Structure Communications, 1982, vol. 11, Issue 4, pp. 1245-1252.
Hai et al., Species- or isozyme-specific enzyme inhibitors. 9. Selective effects in inhibitions of rat pyruvate kinase isozymes by adenosine 5'-diphosphate derivatives, Journal of Medicinal Chemistry, 1982, vol. 25, Issue 10, pp. 1184-1188.
Hai et al., Species- or isozyme-specific enzyme inhibitors. 7. Selective effects in inhibitions of rat adenylate kinase isozymes by adenosine 5'-phosphate derivatives, Journal of Medicinal Chemistry, 1982, vol. 25, Issue 7, pp. 806-812.
Hampton et al., Substrate properties of cycloadenosines with adenosine aminohydrolase as evidence for the conformation of enzyme-bound adenosine, Biochemistry, 1972, vol. 11, Issue 25, pp. 4736-4739.
Hampton et al., Interactions of epimeric 5'-C-methyl and 5'-C-carbamyl derivatives of adenosine monophosphate with adenosine monophosphate utilizing enzymes, Biochemistry, 1973, vol. 12, Issue 17, pp. 3328-3332.
Hayakawa et al., A strategy for the stereoselective preparation of thymidine phosphorothioates with the (R) or the (S) configuration at the stereogenic oligodeoxyribonucleotides with stereochemically pure phosphate/phosphorothioate chimeric backbones, European Journal of Organic Chemistry, 2006, vol. 17, pp. 3834-3844.
Hayatshahi et al., QSARs and activity predicting models for competitive inhibitors of adenosine deaminase, FEBS Letters, 2007, vol. 581, Issue 3, pp. 506-514.
Hebert et al., Structural features of the noncatalytic cGMP binding sites of frog photoreceptor phosphodiesterase using cGMP analogs, Journal of Biological Chemistry, 1998, vol. 273, Issue 10, pp. 5557-5565.
Heinemann et al., Comparison of the cellular pharmacokinetics and toxicity of 2'.2'-difluorodeoxycytidine and 1-beta-D-arabinofuranosylcytosine, Cancer Research, 1988, vol. 48, pp. 4024-4031.
Henderson et al., Inhibitors of adenine phosphoribosyltransferase, Cancer Chemotherapy Reports Supplement, 1968, vol. 1, Issue 2, pp. 363-373.
Henderson et al., Mechanisms of inhibition of adenine phosphoribosyltransferase by adenine nucleosides and nucleotides, Canadian Journal of Biochemistry, 1970, vol. 48, Issue 5, pp. 573-579.
Hiebl et al., Side-chain derivatives of biologically active nucleosides. Part 1. Side-chain analogs of 3'-azido-3'-deoxythymidine (AZT), Journal of Medicinal Chemistry, 1992, vol. 35, Issue 16, pp. 3016-3023.
Hiebl et al., Side-chain derivatives of biologically active nucleosides. Part 2: Synthesis and anti-HIV activity of 5'-C-methyl derivatives of 3'-fluoro-3'-deoxythymidine, Antiviral Chemistry and Chemotherapy, 1996, vol. 7, Issue 3, pp. 173-77.
Higuchi et al., "Pro-drugs as novel drug delivery systems", A.C.S. Symposium Series, American Chemical Society, 1975, vol. 14, pp. 154-183.
Hillaire-Buys, D. et al., Pharmacological Evaluation and Chemical Stability of 2-benzylthioether-5'-O-(1-thiotriphosphate)-Adenosine, A New Insulin Secretagogue Acting Through P2Y Receptors, Drug Development Research, 2001, vol. 53, No. 1, pp. 33-43.
Hong, J. A. et al., Identification of Critical Ligand Binding Determinants in *Mycrobacterium tuberculosis* Adenosine-5'-phosphosulfate Reductase, Journal of Medicinal Chemistry, 2009, vol. 52, No. 17, pp. 5485-5495.
Howgate et al., Conversion of 2',3'-O-isopropylideneadenosine into 9-(6-deoxy-β-D-allofuranosyl)- and 9-(6-deoxy-α-L-talofuranosyl) adenines, Carbohydrate Research, 1972, vol. 2, pp. 309-315.
Hrdlicka et al., Synthesis and biological evaluation of branched and conformationally restricted analogs of the anticancer compounds

(56) References Cited

OTHER PUBLICATIONS

3'-C-ethynyluridine (EUrd) and 3'-C-ethynylcytidine (ECyd), Bioorganic & Medicinal Chemistry, 2005, vol. 13, vol. 7, pp. 2597-2621.

Hrebabecky et al., Synthesis of 1-(3-azido-2,3-dideoxy-B-D-allofuranosyl)thymine, 1-(2,3-dideoxy-B-D-allofuranosyl)thymine, and 1-(2,3-dideoxy-B-D-erythro-hex-2-enofuranosyl)thymine*, Carbohydrate Research, 1991, vol. 216, pp. 179-186.

Huang et al., Recent development of therapeutics for chronic HCV infection, Antiviral Research, 2006, vol. 71, Issue 2&3, pp. 351-362.

Hung et al., A New Nonhydrolyzable Reactive cGMP Analogue, (Rp) -Guanosine-3',5'-cyclic-S-(4-bromo-2,3-dioxobutyl) monophosphorothioate Which Targets the cGMP Binding Site of Human Platelet PDE3A, Bioorganic Chemistry, 2008, vol. 36, Issue 3, Elsevier Inc., pp. 141-147.

Hung et al., A new nonhydrolyzable reactive cAMP analog, (Sp)-adenosine-3',5'-cyclic-S-(4-bromo-2,3-dioxobutyl) monophosphorothioate irreversibly inactivates human platelet cGMP-inhibited cAMP phosphodiesterase, Bioorganic Chemistry, 2002, vol. 30, vol. 1, pp. 16-31.

Hung et al., New insights from the structure-function analysis of the catalytic region of human platelet phosphodiesterase 3A: A role for the unique 44-amino acid insert, Journal of Biological Chemistry, 2006, vol. 281, Issue 39, pp. 29236-29244.

Hung et al., A nonhydrolyzable reactive cAMP analogue, (Sp) -8-[4-bromo-2,3-dioxobutyl) thio]adenosine 3', 5'-cyclic S-(methyl) monophosphorothioate, irreversibly inactivates human platelet cGMP-inhibited cAMP phosphodiesterase at micromolar concentrations, Biochemistry, 2002, vol. 41, Issue 9, pp. 2962-2969.

Iimori et al., A study on conformationally restricted sangivamycins and their inhibitory abilities of protein kinases, Nucleic Acids Symposium Series, 1992, vol. 27, pp. 169-170.

Iimori et al., 2'-C-, 3'-C-, and 5'-C-Methylsangivamycins: Conformational lock with the methyl group, Tetrahedron Letters, 1991, vol. 32, Issue 49, pp. 7273-7276.

IUPAC-IUB Commission on Biochemical Nomenclature, Biochemistry, 1972, vol. 11, pp. 942-944.

Jacobson et al., Structure-activity relationships of 9-alkyladenine and ribose-modified adenosine derivatives at rat A3 adenosine receptors, Journal of Medicinal Chemistry, 1995, vol. 38, Issue 10, pp. 1720-1735.

Kappler et al., Isozyme-specific enzyme inhibitors. 10. Adenosine 5'-triphosphate derivatives as substrates or inhibitors of methionine adenosyltransferases of rat normal and hepatoma tissues, Journal of Medicinal Chemistry, 1986, vol. 29, Issue 3, pp. 318-322.

Kappler et al., Species- or isozyme-selective enzyme inhibitors. 8. Synthesis of disubstituted two-substrate condensation products as inhibitors of rat adenylate kinases, Journal of Medicinal Chemistry, 1982, vol. 25, Issue 10, pp. 1179-1184.

Karpeiskii et al., Conformational analogs of nucleotides. V. Synthesis of 5'-C-methylnucleosides from 6-deoxy-D-allose, Bioorganicheskaya Khimiya, 1979, vol. 5, No. 6, pp. 895-905.

Karpeiskii et al., Conformational analogs of nucleotides. V. Synthesis of 5'-C-methylnucleosides from 6-deoxy-D-allose, Soviet Journal of Bioorganic Chemistry (a translation of Bioorganicheskaya Khimiya), 1979, vol. 5, No. 1, pp. 672-680.

Karpeiskii et al., Study of substrate specificity of nuclease S1 from *Aspergillus oryzae* in the hydrolysis of low molecular weight substrates, Bioorganicheskaya Khimiya, 1982, vol. 8, Issue 3, pp. 386-395.

Karpeiskii et al., A study of substrate specificity of nuclease S1 from *Aspergillus oryzae* in the hydrolysis of low-molecular-weight substrates, Soviet Journal of Bioorganic Chemistry (a translation of Bioorganicheskaya Khimiya), 1983, vol. 8, Issue 3, pp. 196-204.

Karpeiskii et al., Snthesis of 5'-C-methyluridines (D-allo and L-talo), 5'-mono-, di- and triphosphates, and dinucleoside phosphates on their basis, Nucleic Acids Symposium Series, 1981, Issue 9, pp. 157-160.

Karpeiskii et al., Synthesis of 5'-mono-, di- and triphosphates of 5'-C-methyluridines, Bioorganicheskaya Khimiya, 1982, vol. 8, Issue 7, pp. 933-939.

Karpeiskii et al., Synthesis of 5'-mono-, 5'-di- and 5'-triphosphates of 5'-C-methyluridines, Soviet Journal of Bioorganic Chemistry (a translation of Bioorganicheskaya Khimiya), 1983, vol. 8, Issue 7, pp. 498-504.

Kett et al., Heterocyclic derivatives of sugars: An NMR study of the formation of 1-glycosyl-3, 5-dimethyl-1H-pyrazoles from hydrazones, Carbohydrate Research, 1997, vol. 299, Issue 3, pp. 129-141.

Kim et al., The effect of thalidomide and its derivatives on thyroxine-induced metamorphosis of tadpole, Canadian Journal of Biochemistry and Physiology, 1965, vol. 43, Issue 6, pp. 769-779.

Klumpp et al., The novel nucleoside analog R1479 (4'-azidocytidine) is a potent inhibitor of NS5B-dependent RNA synthesis and hepatitis C virus replication in cell culture, Journal of Biological Chemistry, 2006, vol. 281, Issue 7, pp. 3793-3799.

Krakowiak et al., Stereochemistry of rHint1 hydrolase assisted cleavage of P-N bond in nucleoside 5'-O-phosphoramidothioates, Chemical Communications, 2007, vol. 21, pp. 2163-2165.

Kiuru et al., Synthesis and enzymatic deprotection of biodegradably protected dinucleoside-2',5'-monophosphates: 3-(acetyloxy)-2,2-bis(ethoxycarbonyl)propyl phosphoesters of 3'-O-(acyloxymethyl)adenylyl-2',5'-adenosines, Chemistry and Biodiversity, 2011, vol. 8, Issue 2, pp. 266-286.

Lau et al., Synthesis and evaluation of antiviral activity of L-acosamine and L-ristosamine nucleosides of furanose configuration, Acta Chemica Scandinavica, 1991, vol. 45, Issue 6, pp. 616-620.

Leisvouri et al., Chemical and enzymatic stability of amino acid derived phosphoramidates of antiviral nucleoside 5'-monophosphates bearing a biodegradable protecting group, Organic and Biomolecular Chemistry, 2010, vol. 8, Issue 9, pp. 2131-2141.

Lepage et al., Metabolism of purine nucleoside analogs, Cancer Research, 1965, vol. 25, pp. 46-52.

Lerner, 9-α-L-Rhamnofuranosyladenine. An improved synthesis of a 6-deoxyhexofuranosyl nucleoside, Nucleic Acid Chem., 1991, vol. 4, pp. 274-280.

Lerner, 9-(6-Deoxyhexofuranosyl) adenine nucleosides. Further studies on the acetolysis of hexofuranosides, Journal of Organic Chemistry, 1978, vol. 43, Issue 5, pp. 962-965.

Lerner, Adenine nucleosides derived from 6-deoxyhexofuranoses, Journal of Organic Chemistry, 1976, vol. 41, Issue 2, pp. 306-310.

Lerner, Interconversions of hexofuranosyl nucleosides. IV. Synthesis of nucleosides derived from 6-deoxy-L-glucose, Journal of Organic Chemistry, 1972, Issue 37, vol. 26, pp. 4386-4391.

Lerner, Interconversions of hexofuranosyl nucleosides. V. Synthesis and reexamination of the structure of 9-(6-deoxy-α-L-mannofuranosyl) adenine, Journal of Organic Chemistry, 1973, vol. 21, pp. 3704-3709.

Lerner et al., Preparation and antileukemic screening of some new 6'-deoxyhexopyranosyladenine nucleosides, J. Med. Chem., 1987, vol. 30, Issue 8, pp. 1521-1525.

Lerner, Preparation of nucleosides via isopropylidene sugar derivatives. V. Coupling reactions using the titanium tetrachloride method, Carbohydrate Research, 1970, vol. 14, Issue 3, pp. 297-303.

Lerner, Synthesis of 9-α-D-rhamofuranosyladenine, Carbohydrate Research, 1974, vol. 38, pp. 328-332.

Lesiak et al., A new approach to syntheses of organic phosphoroselenoates and phosphorodiselenoates. Proof of absolute configuration assignment in diastereomers of cTMPS [thymidine cyclic 3',5'-phosphorothioates], Polish Journal of Chemistry, 1979, vol. 53, Issue 10, pp. 2041-2050.

Lesnikowski et al., A simple procedure for synthesis of diastereoisomers of thymidine cyclic 3',5'- phosphate derivatives, Nucleic Acids Symposium Series, 1987, vol. 18, pp. 273-276.

Lesnikowski et al., Some aspects of the electron impact induced fragmentation of diastereoisomeric thymidine cyclic 3',5'-phosphoranilidothioates, Organic Mass Spectrometry, 1980, vol. 15, Issue 9, pp. 454-455.

Lin, C. et al. Synthesis of Dinucleotide Thiophosphoramidates as Anti-HIV New Prodrugs, Synthesis, 2003, No. 13, pp. 1989-1994.

Lin et al., Novel 3', 5'-cyclic nucleotide analog. Adenosine 3',5'-cyclic boranomonophosphate, Organic Letters, 2001, vol. 3, pp. 795-797.

(56) References Cited

OTHER PUBLICATIONS

Lohmann et al., "Replication of subgenomic hepatitis C virus RNAs in a hepatoma cell line" Science (1999) vol. 285, Issue 5424, pp. 110-113.

Long et al., Structure-activity relationship for adenosine kinase from mycobacterium tuberculosis. II. Modifications to the ribofuranosyl moiety, Biochemical Pharmacology, 2008, vol. 75, Issue 8, pp. 1588-1600.

Malmsjo et al., "Characterization of Contractile P2 Receptors in Human Coronary Arteries by Use of the Stable Pyrimidine Uridine 5'-O-Thiodisphosphate and Uridine 5'-O-3-Thiotriphosphate" J. Pharmcology and Experimental Therapeutics (2000), 293(3):755-760.

Markiewicz et al., The reaction of 1,3-dichloro-1,1,3,3-tetraisopropyldisiloxane with cytosine arabinoside and 1-(6-deoxy-α-L-talofuranosyl) uracil, Collection of Czechoslovak Chemical Communications, 1980, vol. 45, Issue 6, pp. 1860-1865.

Marx et al., Synthesis of 4'-C-acylated thymidines, Helvetica Chimica Acta, 1996, vol. 79, Issue 7, pp. 1980-1994.

McGuigan et al., Phosphate prodrugs derived from N-acetyglucosamine have enhanced chondroprotective activity in explant cultures and represent a new lead in antiosteoarthritis drug discovery, Journal of Medicinal Chemistry, 2008, vol. 51, Issue 18, pp. 5807-5812.

McKenzie et al., Characteristics of the relaxant response of adenosine and its analogs in intestinal smooth muscle, European Journal of Pharmacology, 1977, vol. 41, Issue 2, pp. 183-191.

McKenzie et al., Effects of adenosine and related compounds on adenylate cyclase and cyclic AMP levels in smooth muscle, European Journal of Pharmacology, 1977, vol. 41, Issue 2, pp. 193-203.

McKenzie et al., Hepatic failure and lactic acidosis due to fialuridine (FIAU), an investigational nucleoside analogue for chronic hepatitis B, New England Journal of Medicine, 1995, vol. 333, pp. 1099-1105.

McMurry, Organic Chemistry, 5th ed., Brooks/Cole, Pacific Grove, CA (2000), Chapter 11.5, pp. 398 & 408.

McOmie, Protective Groups in Organic Chemistry, Plenum Press (1973), Cover & Contents pages only.

Miao et al., One pot synthesis of aryl thiophosphoramidate derivatives of AZT, Synthetic Communications, 2002, vol. 32, Issue 21, pp. 3301-3309.

Miao et al., A stepwise one pot synthesis of alkyl thiophosphoramidate derivitaves of nucleosides, Synthetic Communications, 2002, vol. 32, Issue 8, pp. 1159-1167.

Miao et al., One pot synthesis of nucleoside 5'-thiophosphoramidates, Synthetic Communications, 2002, vol. 32, Issue 7, pp. 1069-1076.

Mikhailov, Conformational analogs of nucleotides. Synthesis of 5'-C-methyl nucleosides, Sint. Issled. Biol. Soedin., Tezisy Dokl. Konf. Molodykh Uch., 1978, vol. 6, pp. 38-39.

Mikhailov et al., Conformational peculiarities of 5'-C-methylnucleosides, Bioorganicheskaya Khimiya, 1989, vol. 15, Issue 7, pp. 969-975.

Mikhailov et al., Conformational features of 5'-C-methylnucleosides, Soviet Journal of Bioorganic Chemistry (a translation of Bioorganicheskaya Khimiya), 1990, vol. 15, Issue 7, pp. 532-538.

Misiura et al., Synthesis, chemical and enzymatic reactivity, and toxicity of dithymidylyl-3',5'-phosphorofluoridate and -phosphorothiofluoridate, Bioorganic & Medicinal Chemistry, 2001, vol. 9, Issue 6, pp. 1525-1532.

Murai et al., A synthesis and an x-ray analysis of 2'-C-, 3'-C- and 5'-C-methylsangivamycins, Heterocycles, 1992, vol. 33, Issue 1, pp. 391-404.

Myers et al., Synthetic studies of the tunicamycin antibiotics. Preparation of (+)-tunicaminyluracil, (+)-tunicamycin-V, and 5'-epi-tunicamycin-V, Journal of the American Chemical Society, 1994, vol. 116, Issue 11, pp. 4697-4718.

Nelson et al., Synthesis and antitumor activity of 7- and 9-(6'-deoxy-α-L-talofuranosyl)-hypoxathine and 9-(6'-deoxy-α-L-talofuranosyl)-6-thiopurine, Journal of Medicinal Chemistry, 1983, vol. 26, Issue 10, pp. 1527-1530.

Nelson et al., Synthesis of hypoxanthine, guanine, and 6-thiopurine nucleosides of 6-deoxy-D-allofuranose, Journal of Medicinal Chemistry, 1983, vol. 26, Issue 7, pp. 1071-1074.

Nelson et al., Synthesis of methyl 3,5-di-O-benzoyl-2,6-dideoxy-β-L-lyxo-hexofuranoside, a nucleoside precursor, Carbohydrate Research, 1983, vol. 124, Issue 1, pp. 161-165.

Nutt et al., Branched-chain sugar nucleosides. II. 5',5'-Di-C-methyladenosine, Journal of Medicinal Chemistry, 1968, vol. 11, Issue 1, pp. 151-153.

Oivanen et al., Hydrolysis of isomeric cytidyl-(3' ,5')-5'-C-methyluridines by acids, bases and metal ions: Steric effects in the hydrolysis of the phosphodiester bonds of RNA, Acta Chemica Scandinavica, 1995, vol. 49, Issue 4, pp. 307-310.

Ora et al., Hydrolytic stability of nucleoside phosphotriesters derived from bis(hydroxymethyl)-1,3-dicarbonyl compounds and their congeners: Towards a novel pro-drug strategy for antisense oligonucleotides, J. Chem. Soc. Perkin Trans. 2, 2001, vol. 6, pp. 881-885.

Ora et al., Biodegradable protections for nucleoside 5'-monophosphates: Comparative study on the removal of O-acetyl and O-acetyloxymethyl protected 3-hydroxy-2,2-bis(ethoxycarbonyl)propyl groups, Journal of Organic Chemistry, 2009, vol. 74, Issue 14, pp. 4992-5001.

Padyukova et al., Synthesis of thymidine 5'-derivatives, Bioorganicheskaya Khimiya, 1990, vol. 16, Issue 5, pp. 668-673.

Padyukova et al., Synthesis of 5'-derivatives of thymidine, Soviet Journal of Bioorganic Chemistry (a translation of Bioorganicheskaya Khimiya), 1991, vol. 16, Issue 5, pp. 370-375.

Padyukova et al., Synthesis of dinucleoside phosphates containing 5'-O-bonded 1-(6-deoxy-β-D-allofuranosyl) uracil and 1-(6-deoxy-α-L-talofuranosyl) uracil, Collection of Czechoslovak Chemical Communications, 1980, vol. 45, Issue 9, pp. 2550-2557.

Panova et al., Substrate specificity of escherichia coli thymidine phosphorylase, Biochemistry, 2007, vol. 72, Issue 1, pp. 21-28.

Parker et al., Design and evaluation of 5'-modified nucleoside analogs as prodrugs for an E. coli purine nucleoside phosphorylase mutant, Nucleosides Nucleotides and Nucleic Acids, 2005, vol. 24, Issues 5/6/7, pp. 387-392.

Poijärvi et al., Towards nucleotide prodrugs derived from 2,2-bis(hydroxymethyl)malonate and its congeners: Hydrolytic cleavage of 2-cyano-2-(hydroxymethyl)-3-methoxy-3-oxopropyl and 3-(alkylamino)-2-cyano-2-(hydroxymethyl)-3-oxopropyl protections from the internucleosidic phosphodiester and phosphorothioate linkages, Helv. Chim Acta., 2002, vol. 85, pp. 1869-1876.

Poijärvi et al., Towards oligonucleotide pro-drugs: 2,2-Bis(ethoxycarbonyl) and 2-(alkylaminocarbonyl)-2-cyano substituted 3-(pivaloyloxy)propyl groups as biodegradable protecting groups for internucleosidic phosphoromonothioate linkages, Lett. Org. Chem., 2004, vol. 1, pp. 183-188.

Poijärvi et al., 2,2-Bis(ethoxycarbonyl)- and 2-(alkylaminocarbonyl)-2-cyano-substituted 3-(pivaloyloxy)propyl groups as biodegradable phosphate protections of oligonucleotides, Bioconjugate Chem., 2005, vol. 16, pp. 1564-1571.

Prakash et al., Synthesis and evaluation of S-acyl-2-thioethyl esters of modified nucleoside 5'-monophosphates as inhibitors of hepatitis C virus RNA replication, Journal of Medicinal Chemistry, 2005, vol. 48, Issue 4, pp. 1199-1210.

Pravdina et al., Inhibition by nucleoside 5'-triphosphate analogs of RNA synthesis catalyzed by RNA polymerase of influenza A virus, Molekulyarnaya Genetika, Mikrobiologiya I Virusologiya, 1990, vol. 11, pp. 22-25.

Prichard et al., "A three-dimensional model to analyze drug-drug interactions" Antiviral Res. (1990) vol. 14 Issue 4-5, pp. 181-205.

Ranganathan et al., Model analogs of nucleoside 3', 5'-cyclic phosphates. I. 5'-Mono- and dimethyl analogs of adenosine 3',5'-cyclic phosphate, Journal of Organic Chemistry, 1974, vol. 39, Issue 3, pp. 290-298.

(56) References Cited

OTHER PUBLICATIONS

Reimer et al., Inhibition of hepatitis B virus DNA polymerase by thymidine triphosphate analogs in vitro, Antiviral Chemistry and Chemotherapy, 1991, vol. 2, Issue 4, pp. 249-253.
Reist et al., Potential anticancer agents. LXXVII. Synthesis of nucleosides of purine-6-thiol (6-mercaptopurine) containing "fraudulent" sugars, Journal of Organic Chemistry, 1962, vol. 27, pp. 3279-3283.
Reist et al., Potential anticancer agents. VIII. Synthesis of nucleosides derived from L-talofuranose, Journal of the American Chemical Society, 1958, vol. 80, pp. 5775-5779.
Reist et al., Potential anticancer agents. IV. Synthesis of nucleosides derived from 6-deoxy-D-allofuranose, Journal of the American Chemical Society, 1958, vol. 80, pp. 3962-3966.
Reist et al., Potential anticancer agents. XI. Synthesis of nucleosides derived from 6-deoxy-L-idofuranose, Journal of Organic Chemistry, 1958, vol. 23, pp. 1757-1760.
Reist et al., Potential anticancer agents. X. Synthesis of nucleosides derived from 6-deoxy-D-glucofuranose, Journal of Organic Chemistry, 1958, vol. 23, pp. 1753-1757.
Roche, Bioreversible carriers in drug design: Theory and application, Pergamon Press: New York, 1987, pp. 14-21.
Saha et al., 5'-Methyl-DNA—A new oligonucleotide analog: Synthesis and biochemical properties, Journal of Organic Chemistry, 1995, vol. 60, Issue 4, pp. 788-789.
Sakai et al., Isolation from nocardioides sp. strain CT16, purification, and characterization of a deoxycytidine deaminase extremely thermostable in the presence of D,L-dithiothreitol, Biosci. Biotechnol. Biochem., 2002, vol. 66, Issue 8, pp. 1646-1651.
Scott et al., Mapping ligand interactions with the hyperpolarization activated cyclic nucleotide modulated (HCN) ion channel binding domain using a soluble construct, Biochemistry, 2007, vol. 46, Issue 33, pp. 9417-9431.
Secrist et al., Gene therapy of cancer: Activation of nucleoside prodrugs with *E. coli* purine nucleoside phosphorylase, Nucleosides & Nucleotides, 1999, vol. 18, Issue 4&5, pp. 745-757.
Severe Toxicity of Fialuridine (letters to the editor), New England Journal of Medicine, 1996, vol. 334, pp. 1135-1138.
Shaw et al., Mass spectrometry of nucleic acid components Analogs of adenosine, Journal of the American Chemical Society, 1970, vol. 92, Issue 8, pp. 2510-2522.
Sheid et al., Enzymatic formation of potential anticancer and antiviral inosine analogs, Experientia, 1996, vol. 52, Issue 9, pp. 878-881.
Shigeura et al., Structural basis for phosphorylation of adenosine congeners, Nature, 1967, vol. 215, Issue 5099, pp. 419-420.
Shuto et al., Stereo- and regioselective introduction of 1- or 2-hydroxyethyl group via intramolecular radical cyclization reaction with a novel silicon-containing tether. An efficient synthesis of 4'α-branched 2'-deoxyadenosines, Journal of Organic Chemistry, 1998, vol. 63, Issue 3, pp. 746-754.
Smith et al., The design, synthesis, and antiviral activity of monofluoro and difluoro analogues of 4'- azidocytidine and against hepatitis C virus replication: The discovery of 4'-azido-2'-deoxy-2'-fluorocytidine and 4'-azido-2'-dideoxy-2',2'-difluorocytidine, Journal of Medicinal Chemistry, 2009, vol. 52, pp. 2971-2978.
Sopchik et al., Facile preparation of the individual diastereoisomers of thymidine 3',5'-cyclic phosphorothioate (cTMPS), Tetrahedron Letters, 1981, vol. 22, Issue 4, pp. 307-310.
Spormann et al., Synthesis and photoreaction of 4'-pivaloyl guanosides, Synthesis, 2001, vol. 14, pp. 2156-2164.
Srivastava et al., Enantiomeric forms of 9-(5,6-dideoxy-α-D-arabino-hex-5-enofuranosyl) adenine and preparation of 9-(6-deoxy-β-D-galactofuranosyl) adenine. Further results with the acetolysis of hexofuranosides, Tetrahedron, 1978, vol. 34, Issue 17, pp. 2627-2631.
Streitwieser et al., Introduction to Organic Chemistry, 3rd ed., Macmillan Publishing Co. Inc., New York, NY, 1985, pp. 113-139.
Streitwieser et al., Introduction to Organic Chemistry, 2nd ed., Macmillan Publishing Co. Inc., New York, NY, 1981, pp. 169-171.

Sun et al., Effects of cGMP, cAMP and two other cAMP derivatives on the anscription system of isolated rat liver nuclei, Shengwu Huaxue Zazhi, 1987, vol. 3, Issue 5, pp. 455-461.
Tian et al., Synthesis of 8-chloroadenosine 3',5'-cyclophosphotriesters and phosphoramidates, Progress in Natural Science, 1994, vol. 4, Issue 6, pp. 726-731.
Tomassini et al., Inhibitory effect of 2'-substituted nucleosides on hepatitis C virus replication correlates with metabolic properties in replicon cells, Antimicrobial Agents and Chemotherapy, 2005, vol. 49, Issue 5, pp. 2050-2058.
Tomei et al., HCV antiviral resistance: The impact of in vitro studies on the development of antiviral agents targeting the viral NS5B polymerase, Antiviral Chemistry and Chemotherapy, 2005, vol. 16, Issue 4, pp. 225-245.
Trafelet et al., Synthesis of (5'S)-5'-C-alkyl-2'-deoxynucleosides, Helvetica Chimica Acta, 2001, vol. 84, Issue 1, pp. 87-105.
Tunitskaya et al., Substrate properties of C'-methyl UTP derivatives in T7 RNA polymerase reactions. Evidence for N-type NYP conformation, FEBS Letters, 1997, vol. 400, Issue 3, pp. 263-266.
Ueno et al., Nucleosides and nucleotides. 174. Synthesis of oligodexynucleotides containing 4'-C-[2-[[N-(2-aminoethyl)carbamoyl]oxy]ethyl]thymidine and their thermal stability and nuclease-resistance properties, Journal of Organic Chemistry, 1998, vol. 63, Issue 5, pp. 1660-1667.
Venkatachalam et al., A comparative study of the hydrolysis pathways of substituted aryl phosphoramidate versus aryl thiophosphoramidate derivatives of stavudine, European Journal of Medicinal Chemistry, 2004, vol. 39, pp. 665-683.
Vilar et al., Probabilistic neural network model for the in silico evaluation of anti-HIV activity and mechanism of action, Journal of Medicinal Chemistry, 2006, vol. 49, Issue 3, pp. 1118-1124.
Walczak et al., Synthesis of 1-(3-(1,2,4-triazol-1-yl)-2,3,6-trideoxy-L-arabino-hexofuranosyl) uracils via an α, β-unsaturated aldehydohexose, Monatshefte für Chemie, 1992, vol. 123, Issue 4, pp. 349-354.
Wang et al., Study on the structure-activity relationship of new anti-HIV nucleoside derivatives based on the Support Vector Machine method, QSAR & Combinatorial Science, 2007, vol. 26, Issue 2, pp. 161-172.
Wang et al., Synthesis and cytokine modulation properties of pyrrolo [2,3-d]-4-pyrimidone nucleosides, Journal of Medicinal Chemistry, 2000, vol. 43, Issue 13, pp. 2566-2574.
Wu et al., The cyclophosphorylation of adenosine, Huaxue Xuebao, 1986, vol. 44, Issue 6, pp. 635-638.
Yakovlev et al., Stereoelectronic effects in the enzymatic cleavage of dinucleoside phosphates by Rnases, Bioorganicheskaya Khimiya, 1985, vol. 11, Issue 2, pp. 205-210.
Yakovlev et al., Stereoelectronic effects in the reactions involved in the enzymatic cleavage of dinucleoside phosphates by Rnases, Soviet Journal of Bioorganic Chemistry (a translation of Bioorganicheskaya Khimiya), 1985, vol. 11, Issue 2, pp. 107-112.
Yakovlev et al., Stereoelectronic effects in Rnase-catalyzed reactions of dinucleoside phosphate cleavage, FEBS Letters, 1985, vol. 179, Issue 2, pp. 217-220.
Zinchenko et al., 2'-, 3'- and 5'-C-Methyl derivatives of uridine in the reaction of microbiological transglycosylation, Doklady Akademii Nauk SSSR, 1987, vol. 297, Issue 3, pp. 731-734.
Zinchenko et al., Substrate specificity of uridine and purine nucleoside phosphorylases of *Escherichia coli* whole cells, Biopolimery I Kletka, 1988, vol. 4, Issue 6, pp. 298-302.
Zinchenko et al., Substrate specificity of uridine and purine nucleoside phosphorylases of the whole cells of *Escherichia coli*, Nucleic Acids Symposium Series, 1987, vol. 18, Issue 7, pp. 137-140.
International Search Report and Written Opinion dated Jun. 4, 2013 for PCT Application No. PCT/US2013/030609, filed Mar. 12, 2013.
International Search Report and Written Opinion issued on May 10, 2013 in PCT Application No. PCT/US2013/030594, filed on Mar. 12, 2013.
Carroll, S. S. et al., "Nucleoside Analog Inhibitors of Hepatitis C Virus Replication" Infectious Disorders—Drug Targets (2006) 6:17-29.

(56) References Cited

OTHER PUBLICATIONS

CAS Reg. No. 18883-94-8, STNEasy, Entry Date Nov. 16, 1984, (https://stneasy.cas.org), retrieved on Aug. 27, 2013.
CAS Reg. No. 71738-02-8, STNEasy, Entry Date Nov. 16, 1984, (https://stneasy.cas.org), retrieved on Aug. 27, 2013.
CAS Reg. No. 80875-87-2, STNEasy, Entry Date Nov. 16, 1984, (https://stneasy.cas.org), retrieved on Aug. 27, 2013.
Feng et al. "Kinetic and mechanistic studies on the dephosphoryl reaction catalyzed in nucleoside 5'-amino acid phosphoramidates" Journal of Molecular Catalysis A: Chemical. (2005) 239: 239-242.
Gemcitabine, The Merck Index (15$^{th}$ Ed. 2013) p. 809.
Gwack et. Al., "DNA Helicase Activity of the Hepatitis C Virus Nonstructural Protein 3," European Journal of Biochemistry (1997) 250(1):47-54.
Lamivudine, The Merck Index (15$^{th}$ Ed. 2013) p. 994.
Lee, C., "Discovery of Hepatitis C Virus NS5A Inhibitors as a New Class of Anti-HCV Therapy" Arch. Pharm. Res., (2011) 34(9):1403-1407.
Pockros, P. J., "Drugs in Development for Chronic Hepatitis C: A Promising Future" Expert Opin. Biol. Ther., (2011) 11(12):1611-1622.
Stanton, G. J., et al., "Interferon Review" Invest. Radiol., (1987) 22(3):259-273.
Zhong W. et al. "Dinucleotide analogues as novel inhibitors of RNA-dependent RNA polymerase of hepatitis C virus." (Aug. 1, 2003) Antimicrobial Agents and Chemotherapy, American Society of Microbiology, US, 47(8):2674-2681.

\* cited by examiner

Figure 1 (cont.)

| # | Formula (A) Structure |
|---|---|
| 1015 | |
| 1016 | |

| # | Formula (A) Structure |
|---|---|
| 1012 | |
| 1013 | |
| 1014 | |

Figure 1 (cont.)

| # | Formula (A) Structure |
|---|---|
| 1026 | (structure with 3-pyridyl aryloxy, alanine isopropyl ester phosphoramidate of 2'-C-methyluridine) |
| 1027 | (structure with phenyl aryloxy, methionine isopropyl ester phosphoramidate of 2'-C-methyluridine) |
| 1028 | (structure with phenyl aryloxy, glycine isopropyl ester phosphoramidate of 2'-C-methyluridine) |

| # | Formula (A) Structure |
|---|---|
| 1023 | (structure with p-tolyl aryloxy, alanine isopropyl ester phosphoramidate of 2'-C-methyluridine) |
| 1024 | (structure with p-methoxyphenyl aryloxy, alanine isopropyl ester phosphoramidate of 2'-C-methyluridine) |
| 1025 | (structure with 5-isoquinolinyl aryloxy, alanine isopropyl ester phosphoramidate of 2'-C-methyluridine) |

Figure 2

| # | Name | Structure |
|---|---|---|
| 3000 | Standard of Care for HCV | Standard of Care for HCV |
| 3001 | Telaprevir VX-950 | 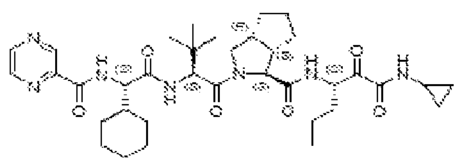 |
| 3002 | MK-5172 | 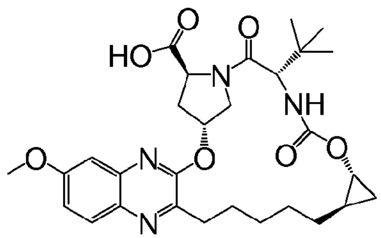 |
| 3003 | ABT-450 | |

| # | Name | Structure |
|---|---|---|
| 3004 | BILN-2061 | 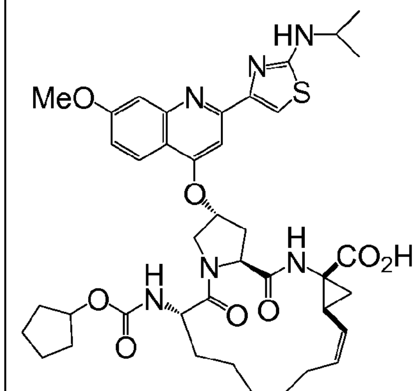 |
| 3005 | BI-201335 BI335 | 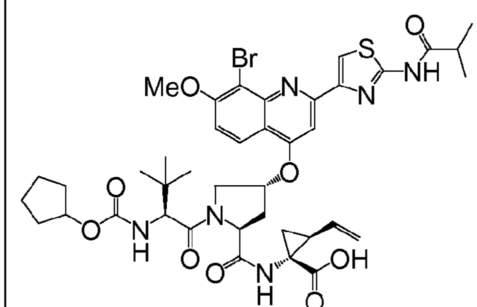 |

| # | Name | Structure |
|---|------|-----------|
| 3013 | TMC-435<br>TMC-435350 | 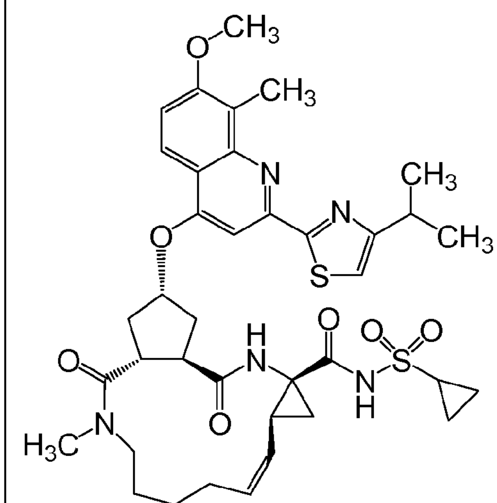 |
| 3014 | Danoprevir<br>ITMN-191<br>RG7227<br>RO5190591 | 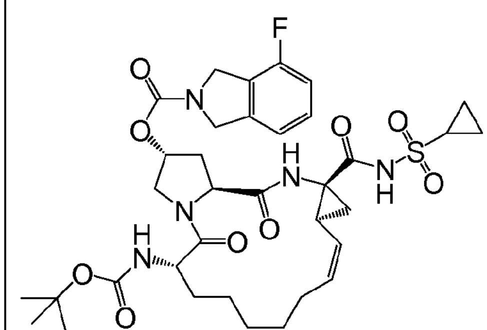 |

| # | Name | Structure |
|---|------|-----------|
| 3006 | BMS-650032<br>BM032<br>Asunaprevir | 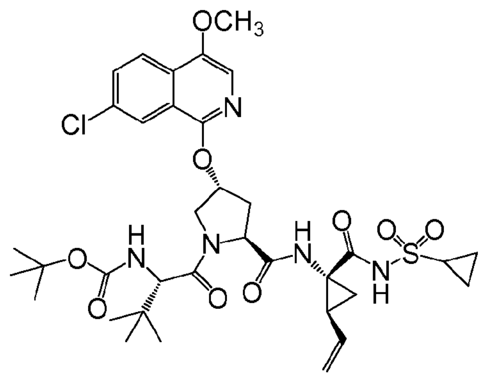 |
| 3007 | Boceprevir<br>SCH 503034 | 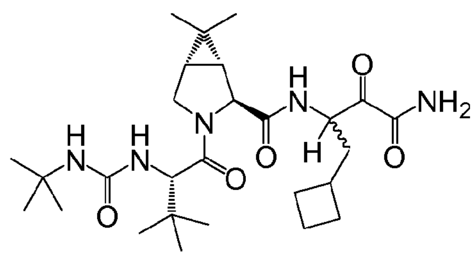 |
| 3008 | GS-9256 | |
| 3009 | GS-9451 | |
| 3010 | IDX-320 | |
| 3011 | ACH-1625 | |
| 3012 | ACH-2684 | |

Figure 2 (cont.)

| # | Name | Structure |
|---|---|---|
| 3019 | PSI-7977 GS-7977, Sofosbuvir | (structure shown) |
| 3020 | PSI-352938 GS-938 | (structure shown) |
| 3021 | 4'-azidouridine and its prodrugs | (structure shown) |
| 3022 | PSI-661 | |
| 3023 | GS-6620 | |
| 3024 | TMC649128 | |

| # | Name | Structure |
|---|---|---|
| 3015 | MK-7009 Vaniprevir | (structure shown) |
| 3016 | PHX1766 | |
| 3017 | RG7128 Mericitabine | (structure shown) |
| 3018 | PSI-7851 | (structure shown) |

| # | Name | Structure |
|---|---|---|
| 3025 | NM283 | 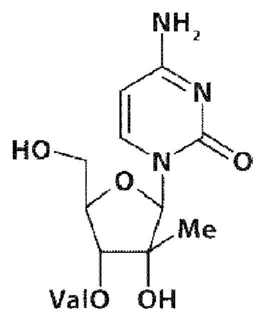 |
| 3026 | BCX5191 | |
| 3027 | IDX19368 | |
| 3028 | IDX19370 | |
| 3029 | ABT-333 | |
| 3030 | ANA-598 Setrobuvir | 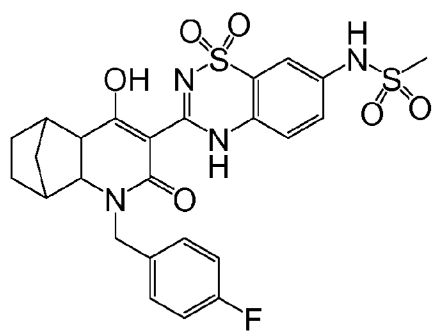 |

| # | Name | Structure |
|---|---|---|
| 3031 | VX-222 S1480 VCH-222 | 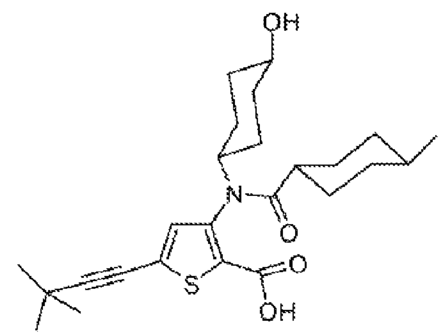 |
| 3032 | HCV-796 | 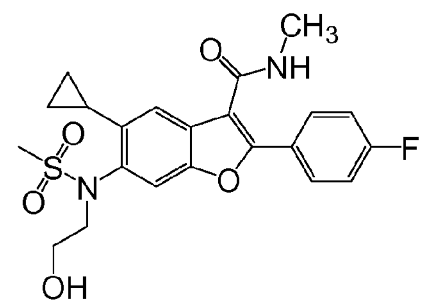 |
| 3033 | BI-207127 | |

| # | Name | Structure |
|---|---|---|
| 3034 | GS-9190 | 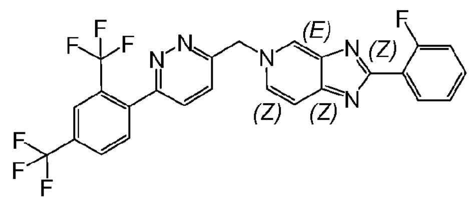 |
| 3035 | Filibuvir PF-00868554 | 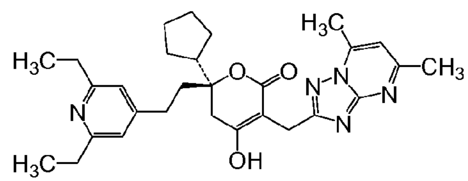 |
| 3036 | VX-497 | 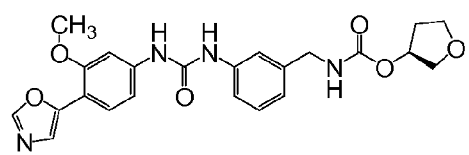 |
| 3037 | ABT-072 | |
| 3038 | MK-3281 | |
| 3039 | TMC647055 | |
| 3040 | BMS-791325 | |
| 3041 | PPI-383 | |
| 3042 | GS9669 | |

| # | Name | Structure |
|---|---|---|
| 3043 | BMS-790052 BMS052 S1482 Daclatasvir | 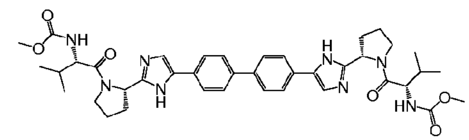 |
| 3044 | PPI-461 | |
| 3045 | ACH-2928 | |
| 3046 | GS-5885 | |
| 3047 | BMS-824393 | |
| 3048 | ABT 267 | |
| 3049 | ACH-3102 | |
| 3050 | AZD-7295 | |
| 3051 | IDX719 | |
| 3052 | PPI-668 | |
| 3053 | MK8742 | |
| 3054 | GSK2336805 GSK805 | |
| 3055 | Debio-025 Alisporivir | |
| 3056 | MIR-122 | |

| # | Name | Structure |
|---|---|---|
| 3057 | clemizole | |
| 3058 | ITX 5061 | |
| 3059 | BIT225 | |
| 3060 | NIM811 | |
| 3061 | SCY-635 | |
| 3062 | Nitazoxanide | 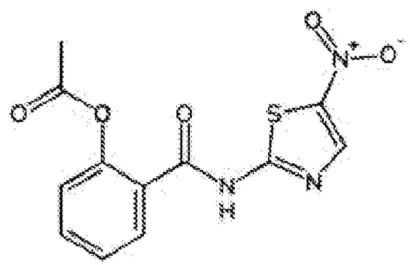 |
| 3063 | Miravirsen | |
| 3064 | Celgosivir | 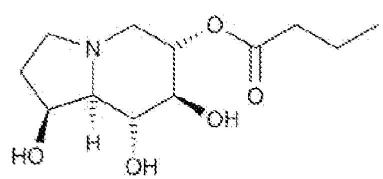 |
| 3065 | GS9620 | |

| # | Name | Structure |
|---|---|---|
| 3066 | Ribavirin |  |
| 3067 | GS-5816 | |

US 9,012,427 B2

PHARMACEUTICAL COMBINATIONS COMPRISING A THIONUCLEOTIDE ANALOG

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57, and include U.S. provisional application Nos. 61/614,494, filed Mar. 22, 2012 and 61/613,854, filed Apr. 19, 2012.

BACKGROUND

1. Field

The present application relates to the fields of chemistry, biochemistry and medicine. More particularly, disclosed herein are a thiophosphoroamidate nucleotide analog for use in combination therapy with one or more other agents. Also disclosed herein are methods of treating diseases and/or conditions with a thiophosphoroamidate nucleotide analog in combination with one or more agents.

2. Description

Nucleoside analogs are a class of compounds that have been shown to exert antiviral and anticancer activity both in vitro and in vivo, and thus, have been the subject of widespread research for the treatment of viral infections and cancer. Nucleoside analogs are usually therapeutically inactive compounds that are converted by host or viral enzymes to their respective active metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a combination of a compound of Formula (A) and one or more compounds of Formula (C), or pharmaceutically acceptable salts, hydrates, and solvates of the aforementioned compounds.

Some embodiments disclosed herein relate to methods of ameliorating and/or treating a viral infection (for example, a hepatitis C viral infection) that can include administering to a subject suffering from the viral infection an effective amount of a combination of a compound of Formula (A) and one or more compounds of Formula (C), or pharmaceutically acceptable salts, hydrates, and solvates of the aforementioned compounds. Other embodiments described herein relate to using a combination of a compound of Formula (A) and one or more compounds of Formula (C), or pharmaceutically acceptable salts, hydrates, and solvates of the aforementioned compounds, in the manufacture of a medicament for ameliorating and/or treating a viral infection (for example, a hepatitis C viral infection). Still other embodiments described herein relate to a combination of a compound of Formula (A) and one or more compounds of Formula (C), or pharmaceutically acceptable salts, hydrates, and solvates of the aforementioned compounds, that can be used for ameliorating and/or treating a viral infection (for example, a hepatitis C viral infection).

Some embodiments disclosed herein relate to methods of ameliorating and/or treating a viral infection (for example, a hepatitis C viral infection) that can include contacting a cell infected with the virus (such as the hepatitis C virus) with an effective amount of a combination of a compound of Formula (A) and one or more compounds of Formula (C), or pharmaceutically acceptable salts, hydrates, and solvates of the aforementioned compounds. Other embodiments described herein relate to using one or more compounds described herein, or a pharmaceutically acceptable salt of one or more compounds described herein, in the manufacture of a medicament for ameliorating and/or treating a viral infection (for example, a hepatitis C viral infection) that can include contacting a cell infected with the virus (such as the hepatitis C virus) with an effective amount of a combination of a compound of Formula (A) and one or more compounds of Formula (C), or pharmaceutically acceptable salts, hydrates, and solvates of the aforementioned compounds. Still other embodiments described herein relate to one or more compounds described herein, or a pharmaceutically acceptable salt of one or more compounds described herein, that can be used for ameliorating and/or treating a viral infection (for example, a hepatitis C viral infection) by contacting a cell infected with the virus (such as the hepatitis C virus) with an effective amount of a combination of a compound of Formula (A) and one or more compounds of Formula (C), or pharmaceutically acceptable salts, hydrates, and solvates of the aforementioned compounds.

Some embodiments disclosed herein relate to methods of inhibiting replication of a virus that can include contacting a cell infected with the virus (for example, a hepatitis C virus) with an effective amount of a combination of a compound of Formula (A) and one or more compounds of Formula (C), or pharmaceutically acceptable salts, hydrates, and solvates of the aforementioned compounds. Other embodiments described herein relate to using one or more compounds described herein, or a pharmaceutically acceptable salt of one or more compounds described herein, in the manufacture of a medicament for inhibiting replication of a virus (for example, a hepatitis C virus) that can include contacting a cell infected with the virus with an effective amount of a combination of a compound of Formula (A) and one or more compounds of Formula (C), or pharmaceutically acceptable salts, hydrates, and solvates of the aforementioned compounds. Still other embodiments described herein relate to one or more compounds described herein, or a pharmaceutically acceptable salt of one or more compound described herein, that can be used for inhibiting replication of a virus (for example, a hepatitis C virus) by contacting a cell infected with the virus with an effective amount of an effective amount of a combination of a compound of Formula (A) and one or more compounds of Formula (C), or pharmaceutically acceptable salts, hydrates, and solvates of the aforementioned compounds.

Some embodiments described herein relate to a method of inhibiting a polymerase (for example, NS5B polymerase of a hepatitis C virus) that can include contacting a cell (for example, a cell infected with a hepatitis C virus) with an effective amount of a combination of one or more compounds described herein. Other embodiments described herein relate to using a combination of compounds described herein in the manufacture of a medicament for inhibiting a polymerase (for example, NS5B polymerase of a hepatitis C virus) that can include contacting a cell (for example, a cell infected with a hepatitis C virus) with an effective amount of said combination of compounds. Still other embodiments described herein relate to a combination of compounds described herein that can be used for inhibiting a polymerase (for example, NS5B polymerase of a hepatitis C virus can include contacting a cell (for example, a cell infected with a hepatitis C virus) that with an effective amount of said combination of compounds.

DETAILED DESCRIPTION

Figure 1:
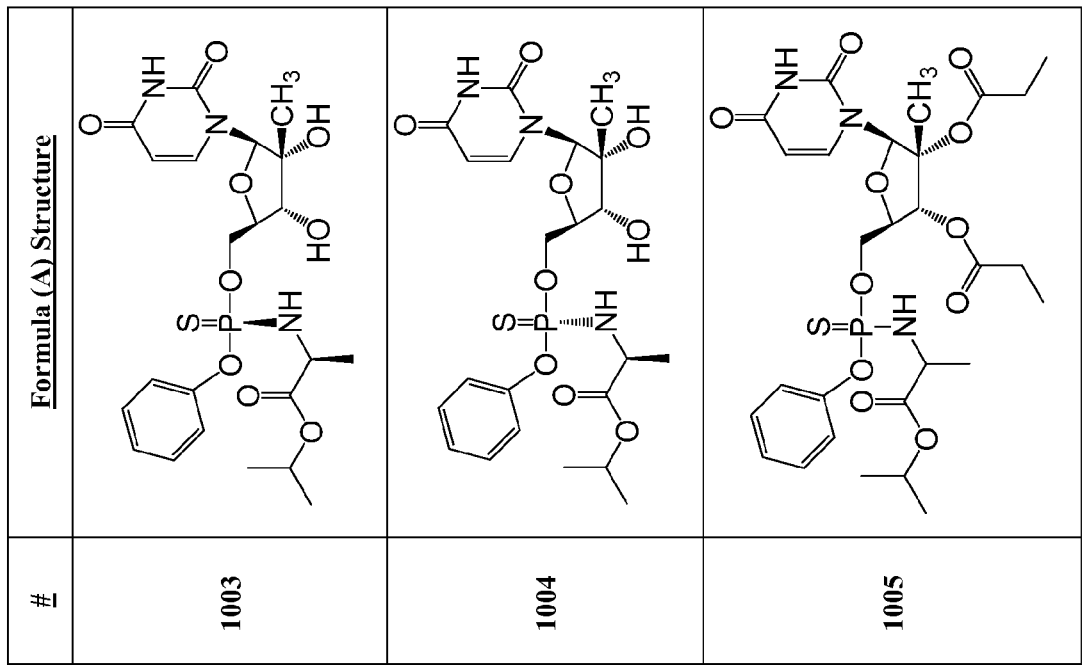
FIG. 1 shows example compounds of Formula (A), including Compounds 1000 through 1032.
Figure 1:
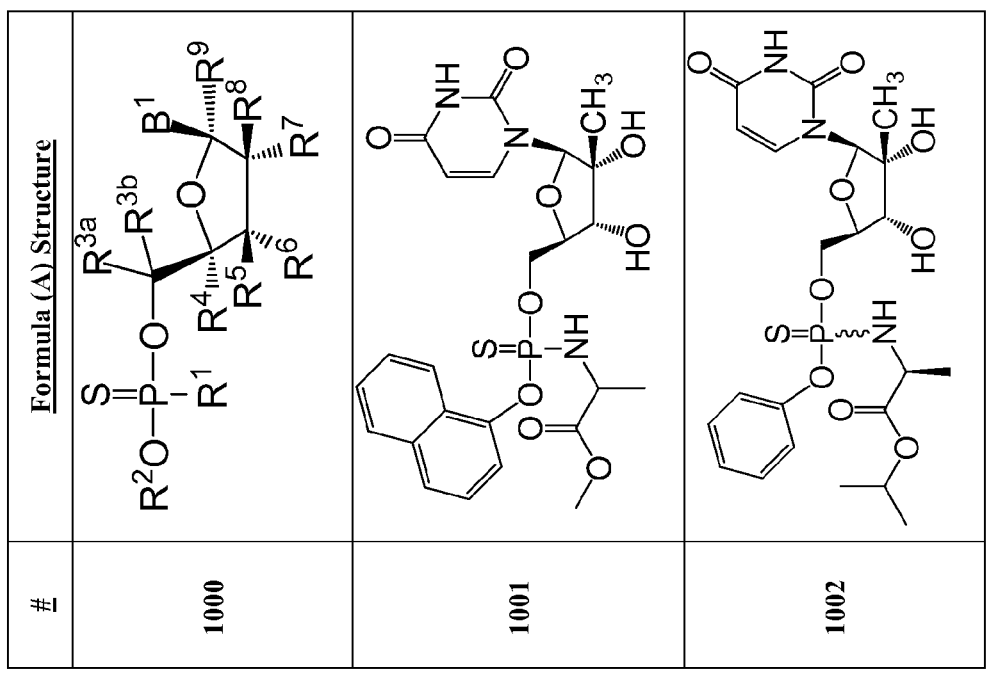
Figure 1:
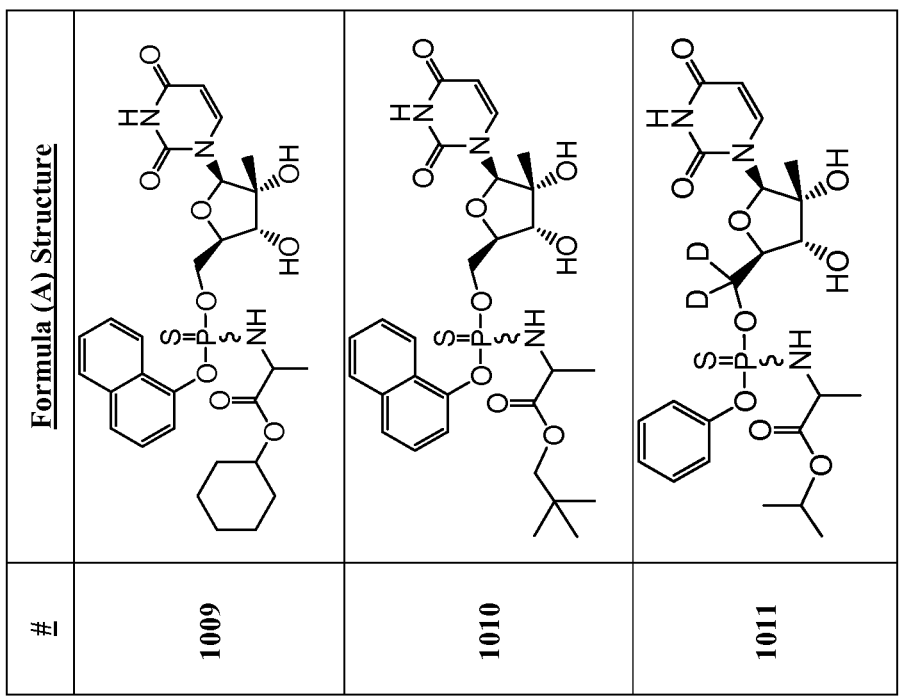
Figure 1:
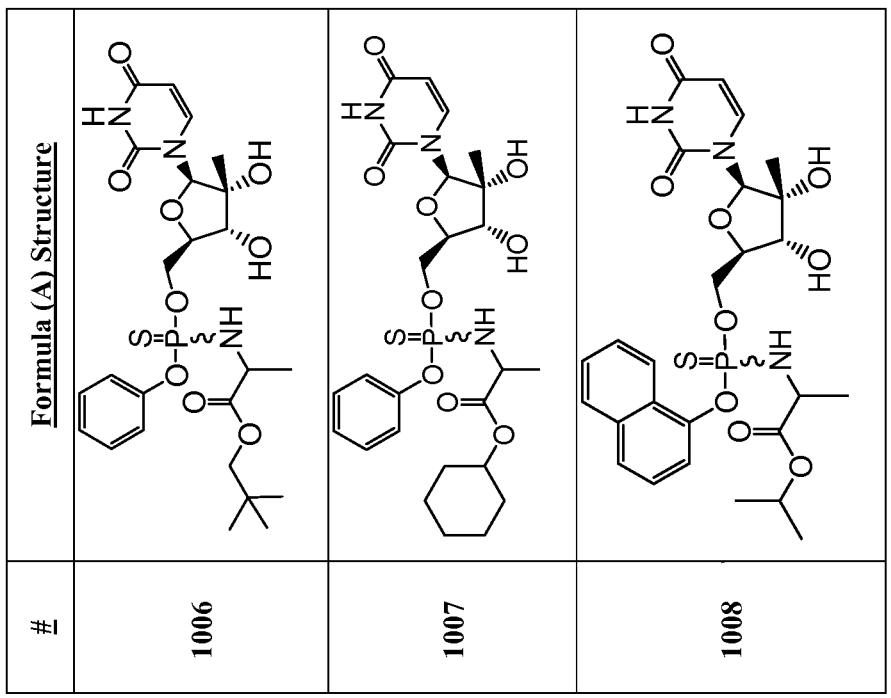
Figure 1:
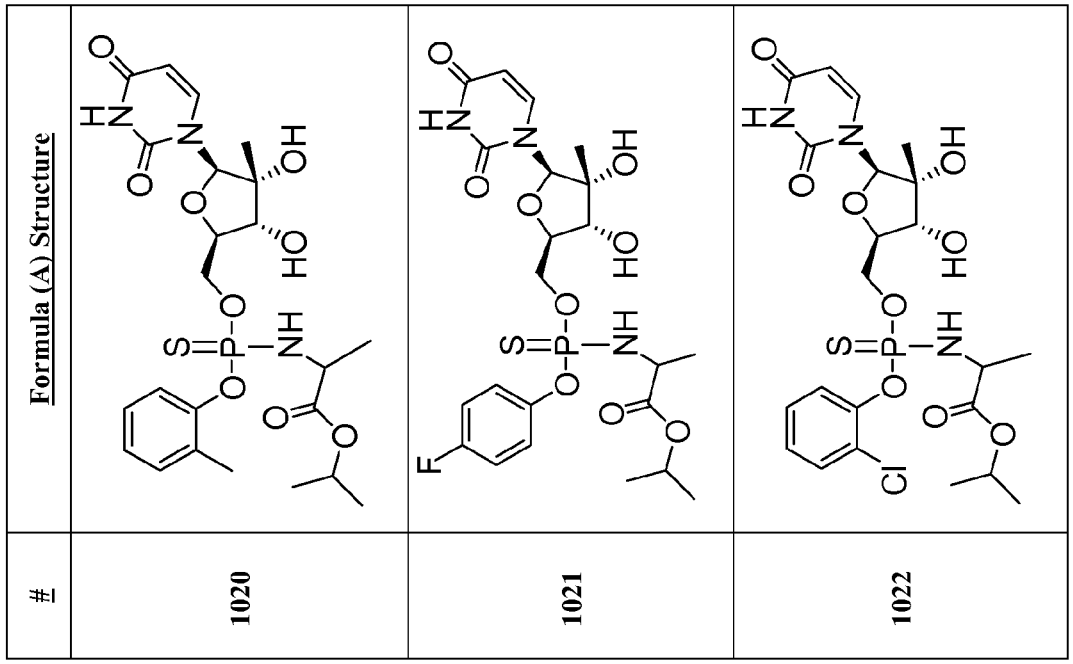
Figure 1:
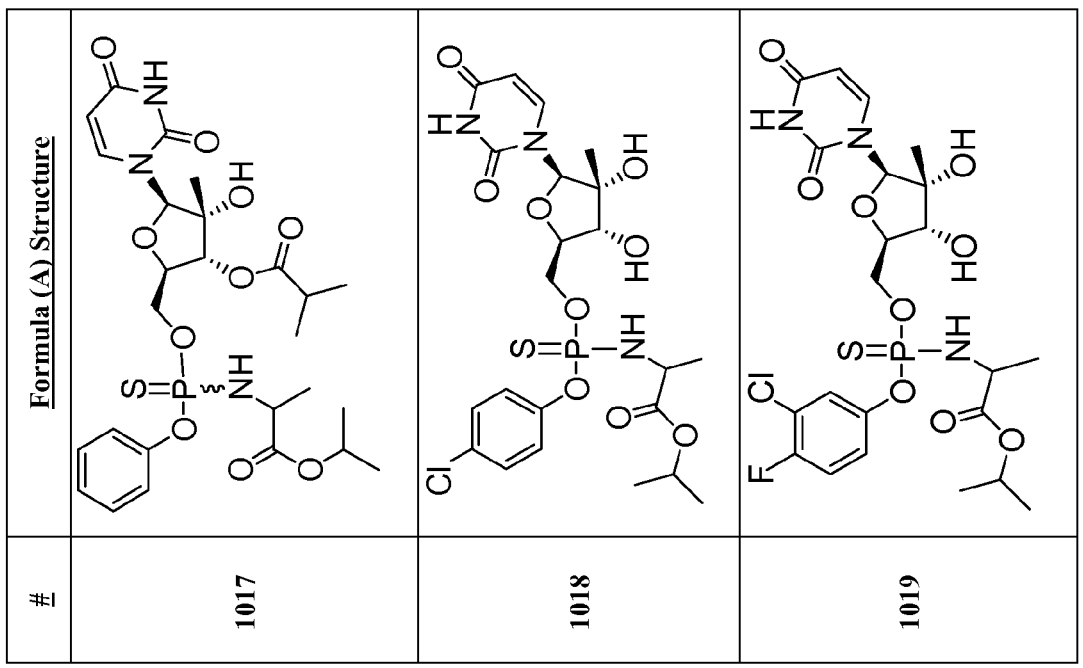
Figure 1:
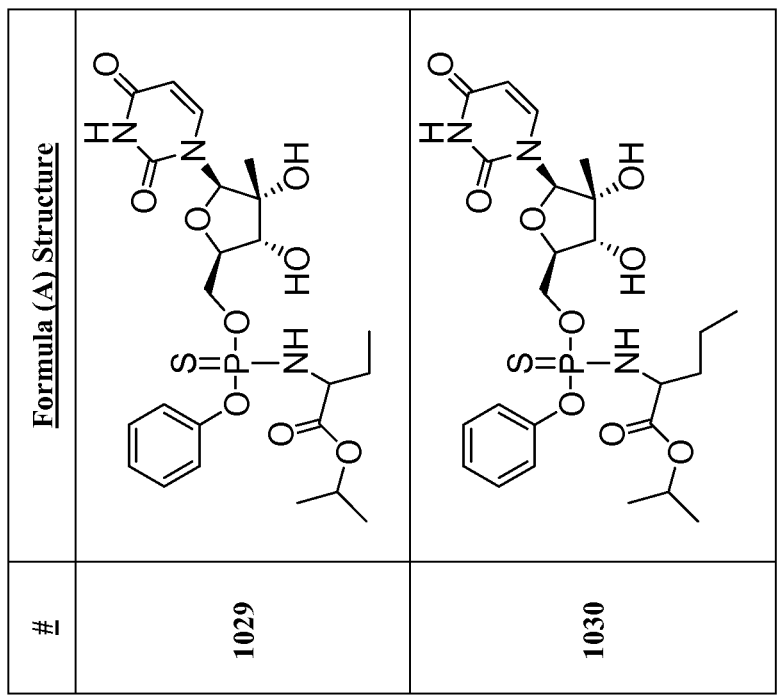
Figure 1:
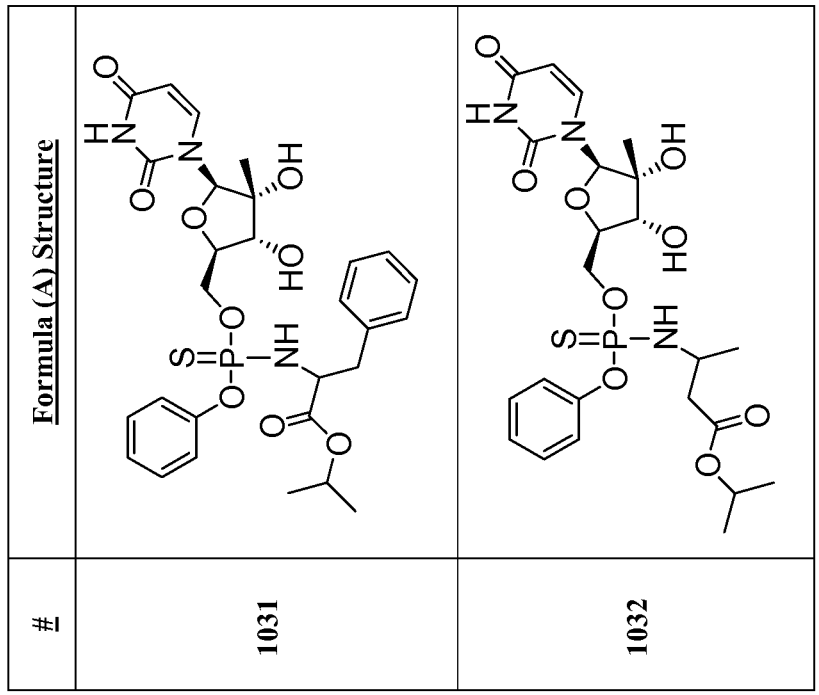

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, R, $R^1$, $R^2$, $R^{3a}$, $R^{3b}$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{1A}$, $R^{2A}$, $R^{3A}$, $R^{3B}$, $R^{4A}$, $R^{5A}$, $R^{6A}$, $R^{7A}$, $R^{8A}$ and R" represent substituents that can be attached to the indicated atom. An R group may be substituted or unsubstituted. If two "R" groups are described as being "taken together" the R groups and the atoms they are attached to can form a cycloalkyl, cycloalkenyl, cycloalkynyl, aryl, heteroaryl or heterocycle. For example, without limitation, if $R^a$ and $R^b$ of an $NR^aR^b$ group are indicated to be "taken together," it means that they are covalently bonded to one another to form a ring:

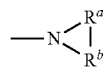

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to a three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" and "(heterocyclyl)alkyl" refer to a heterocyclic or a heteroalicylylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, a cycloalkynyl, aryl, heteroaryl, heteroalicyclyl, aralkyl, (heteroaryl)alkyl or (heteroalicyclyl)alkyl as defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl, and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, and 2-fluoroisobutoxy. A haloalkoxy may be substituted or unsubstituted.

As used herein, "arylthio" refers to RS—, in which R is an aryl, such as but not limited to phenyl. An arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$-" group wherein X is a halogen.

A "trihalomethanesulfonamido" group refers to an "X$_3$CS(O)$_2$N(R$_A$)—" group wherein each X is a halogen and R$_A$ hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl.

The term "amino" as used herein refers to a —NH$_2$ group.
As used herein, the term "hydroxy" refers to a —OH group.
A "cyano" group refers to a "—CN" group.
The term "azido" as used herein refers to a —N$_3$ group.
An "isocyanato" group refers to a "—NCO" group.
A "thiocyanato" group refers to a "—CNS" group.
An "isothiocyanato" group refers to an "—NCS" group.
A "mercapto" group refers to an "—SH" group.
A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g., 7-methylguanine), theobromine, caffeine, uric acid and isoguanine Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The terms "phosphorothioate" and "phosphothioate" refer to a compound of the general formula

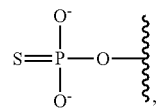

its protonated forms (for example,

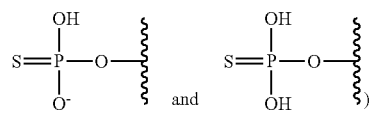 [SMILES: *OP([O-])(O)=S ; *OP(O)(O)=S]

and its tautomers (such as

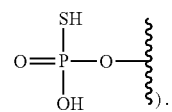

As used herein, the term "phosphate" is used in its ordinary sense as understood by those skilled in the art, and includes its protonated forms (for example,

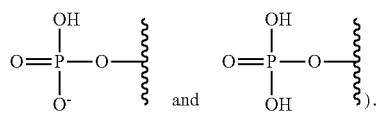

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g., methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g., benzoate ester); carbonates (e.g., methoxymethylcarbonate); sulfonates (e.g. tosylate or mesylate); acyclic ketal (e.g., dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a thiophosphate are intended to be included. Examples of tautomers of a phosphorothioate include the following:

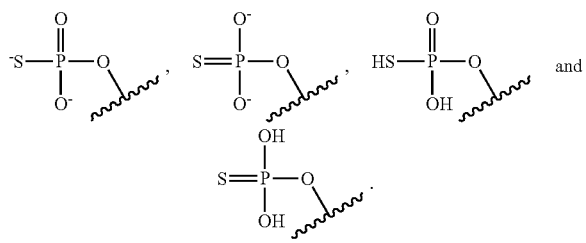

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compound of Formula (A)

Some embodiments disclosed herein relate to a compound of Formula (A) or a pharmaceutically acceptable salt thereof:

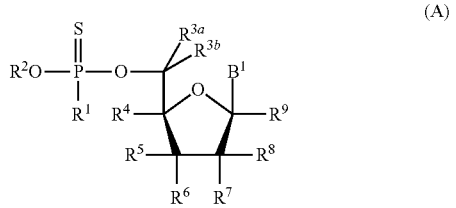

(A)

wherein: $B^1$ can be an optionally substituted heterocyclic base or an optionally substituted heterocyclic base with a protected amino group; $R^1$ can be selected from $O^-$, OH, an optionally substituted N-linked amino acid and an optionally substituted N-linked amino acid ester derivative; $R^2$ can be selected from an optionally substituted aryl, an optionally substituted heteroaryl, an optionally substituted heterocyclyl and

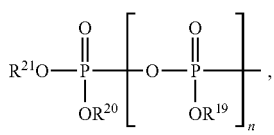

wherein $R^{19}$, $R^{20}$ and $R^{21}$ can be independently absent or hydrogen, and n can be 0 or 1; provided that when $R^1$ is $O^-$ or OH, then $R^2$ is

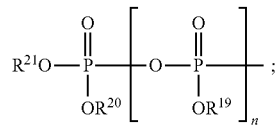

$R^{3a}$ and $R^{3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{3a}$ and $R^{3b}$ can be taken together to form an optionally substituted $C_{3-6}$ cycloalkyl; $R^4$ can be selected from hydrogen, azido, an optionally substituted $C_{1-6}$ alkyl, an optionally substituted $C_{2-6}$ alkenyl and an optionally substituted $C_{2-6}$ alkynyl; $R^5$ can be selected from hydrogen, halogen, azido, cyano, an optionally substituted $C_{1-6}$ alkyl, —$OR^{10}$ and —$OC(=O)R^{11}$; $R^6$ can be selected from hydrogen, halogen, azido, cyano, an optionally substituted $C_{1-6}$ alkyl, —$OR^{12}$ and —$OC(=O)R^{13}$; $R^7$ can be selected from hydrogen, halogen, azido, cyano, an optionally substituted $C_{1-6}$ alkyl, —$OR^{14}$ and —$OC(=O)R^{15}$; or $R^6$ and $R^7$ can be both oxygen atoms and linked together by a carbonyl group; $R^8$ can be selected from hydrogen, halogen, azido, cyano, an optionally substituted $C_{1-6}$ alkyl, —$OR^{16}$ and —$OC(=O)R^{17}$; $R^9$ can be selected from hydrogen, azido, cyano, an optionally substituted $C_{1-6}$ alkyl and —$OR^{18}$; $R^{10}$, $R^{12}$, $R^{14}$, $R^{16}$ and $R^{18}$ can be independently selected from hydrogen and an optionally substituted $C_{1-6}$ alkyl; and $R^{11}$, $R^{13}$, $R^{15}$ and $R^{17}$ can be independently selected from an optionally substituted $C_{1-6}$ alkyl and an optionally substituted $C_{3-6}$ cycloalkyl; with the proviso that when $R^{3a}$, $R^{3b}$, $R^4$, $R^5$, $R^7$, $R^8$ and $R^9$ are all hydrogen, then $R^6$ cannot be azido.

With respect to $R^2$, in some embodiments, $R^2$ can be an optionally substituted heteroaryl. In other embodiments, $R^2$ can be an optionally substituted heterocyclyl. In still other embodiments, $R^2$ can be an optionally substituted aryl. For example, $R^2$ can be an optionally substituted phenyl or an optionally substituted naphthyl. If $R^2$ is a substituted phenyl or a substituted naphthyl, the phenyl ring and the naphthyl ring(s) can be substituted one or more times. Suitable substituents that can be present on optionally substituted phenyl and an optionally substituted naphthyl include electron-donating groups and electron-withdrawing groups. In some embodiments, $R^2$ can be a para-substituted phenyl. In other embodiment, $R^2$ can be an unsubstituted phenyl or an unsubstituted naphthyl. In yet still other embodiments, $R^2$ can be

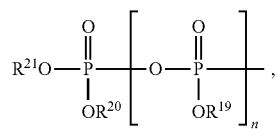

wherein $R^{19}$, $R^{20}$ and $R^{21}$ can be independently absent or hydrogen, and n can be 0 or 1. In some embodiments, n can be 0. In other embodiments, n can be 1. Those skilled in the art understand when n is 0, $R^2$ can be an α-thiodiphosphate. Similarly, those skilled in the art understand when n is 1, $R^2$ can be an α-thiotriphosphate. In some embodiments, at least one of $R^{19}$, $R^{20}$ and $R^{21}$ can be absent. In other embodiments, at least one of $R^{19}$, $R^{20}$ and $R^{21}$ can be hydrogen. In some embodiments, $R^{20}$ and $R^{21}$ can be absent. In other embodiments, $R^{20}$ and $R^{21}$ can be hydrogen. In some embodiments, $R^{19}$, $R^{20}$ and $R^{21}$ can be absent. In some embodiments, $R^{19}$, $R^{20}$ and $R^{21}$ can be hydrogen. Those skilled in the art understand that when any of $R^{19}$, $R^{20}$ and $R^{21}$ are absent the oxygen atom to which $R^{19}$, $R^{20}$ and $R^{21}$ are associated with can have a negative charge. For example, when $R^{20}$ is absent, the oxygen atom to which $R^{20}$ is associated with can be $O^-$. Depending upon the substituents attached to each phosphorus atoms, one or more the phosphorus atoms can be a chiral center. For example, when n is 1, the alpha-phosphorus (the phosphorus nearest to the pentose ring) can be a chiral center. In some embodiments, the alpha-phosphorus can be a (R)-stereocenter. In other embodiments, the alpha-phosphorus can be a (S)-stereocenter.

In some embodiments, $R^1$ can be absent. In other embodiments, $R^1$ can be hydrogen. In still other embodiments, $R^1$ can be an optionally substituted N-linked α-amino acid. In yet still other embodiments, $R^1$ can be an optionally substituted N-linked α-amino acid ester derivative. Various amino acids and amino acid ester derivatives can be used, including those described herein. Suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional suitable amino acids include, but are not limited to, alpha-ethyl-glycine, alpha-propyl-glycine and beta-alanine Examples of an N-linked amino acid ester derivatives include, but are not limited to, an ester derivatives of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of N-linked amino acid ester derivatives include, but are not limited to, an ester derivative of any of the following amino acids: alpha-ethyl-glycine, alpha-propyl-glycine and beta-alanine.

In an embodiment, $R^1$ can be an ester derivative of alanine. In an embodiment, $R^1$ can be selected from alanine methyl ester, alanine ethyl ester, alanine isopropyl ester, alanine cyclohexyl ester, alanine neopentyl ester, valine isopropyl ester and leucine isopropyl ester. In some embodiments, the optionally substituted N-linked amino acid or the optionally substituted N-linked amino acid ester derivative can be in the L-configuration. In other embodiments, the optionally substituted N-linked amino acid or the optionally substituted N-linked amino acid ester derivative can be in the D-configuration.

In some embodiments, when $R^1$ is an optionally substituted N-linked α-amino acid or an optionally substituted N-linked α-amino acid ester derivative, then $R^2$ can be selected from optionally substituted aryl, an optionally substituted heteroaryl and an optionally substituted heterocyclyl. In some embodiments, when $R^1$ is an optionally substituted N-linked α-amino acid ester derivative, then $R^2$ can be an optionally substituted aryl. In other embodiments, when $R^1$ is an optionally substituted N-linked α-amino acid ester derivative, then $R^2$ can be an optionally substituted heteroaryl. In still other embodiments, when $R^1$ is an optionally substituted N-linked α-amino acid ester derivative, then $R^2$ can be an optionally substituted heterocyclyl.

In some embodiments, $R^1$ can have the structure

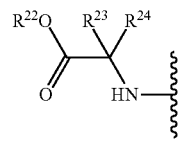

wherein $R^{22}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted $C_{1-6}$ haloalkyl; and $R^{23}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{24}$ can be hydrogen or an optionally substituted $C_{1-4}$-alkyl; or $R^{23}$ and $R^{24}$ can be taken together to form an optionally substituted $C_{3-6}$ cycloalkyl.

When $R^1$ has the structure shown above, $R^{23}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{23}$ is substituted, $R^{23}$ can be substituted with one or more substituents selected from N-amido, mercapto, alkylthio, an optionally substituted aryl, hydroxy, an optionally substituted heteroaryl, O-carboxy, and amino. In some embodiment, $R^{23}$ can be an unsubstituted $C_{1-6}$-alkyl, such as methyl, ethyl, n-propyl, isopropyl, n-butyl, isobutyl, tert-butyl, pentyl (branched and straight-chained), and hexyl (branched and straight-chained). In an embodiment, $R^{23}$ can be methyl.

As to $R^{22}$, in some embodiments, $R^{22}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{22}$ can be methyl or isopropyl. In some embodiments, $R^{22}$ can be ethyl or neopentyl. In other embodiments, $R^{22}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{22}$ can be an optionally substituted cyclohexyl. In still other embodiments, $R^{22}$ can be an optionally substituted aryl, such as phenyl and naphthyl. In yet still other embodiments, $R^{22}$ can be an optionally substituted aryl($C_{1-6}$ alkyl). In some embodiments, $R^{22}$ can be an optionally substituted benzyl. In some embodiments, $R^{22}$ can be an optionally substituted $C_{1-6}$ haloalkyl, for example, $CF_3$.

In some embodiments, $R^{24}$ can be hydrogen. In other embodiments, $R^{24}$ can be an optionally substituted $C_{1-4}$-alkyl, such as methyl, ethyl, n-propyl, isopropyl, n-butyl, isobutyl and tert-butyl. In an embodiment, $R^{24}$ can be methyl. In some embodiments, $R^{23}$ and $R^{24}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{23}$ and $R^{24}$, the carbon to which $R^{23}$ and $R^{24}$ are attached may be a chiral center. In some embodiment, the carbon to which $R^{23}$ and $R^{24}$ are attached may be a (R)-chiral center. In other embodiments, the carbon to which $R^{23}$ and $R^{24}$ are attached may be a (S)-chiral center.

Examples of a suitable

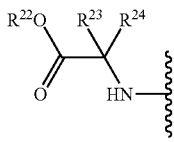

groups include the following:

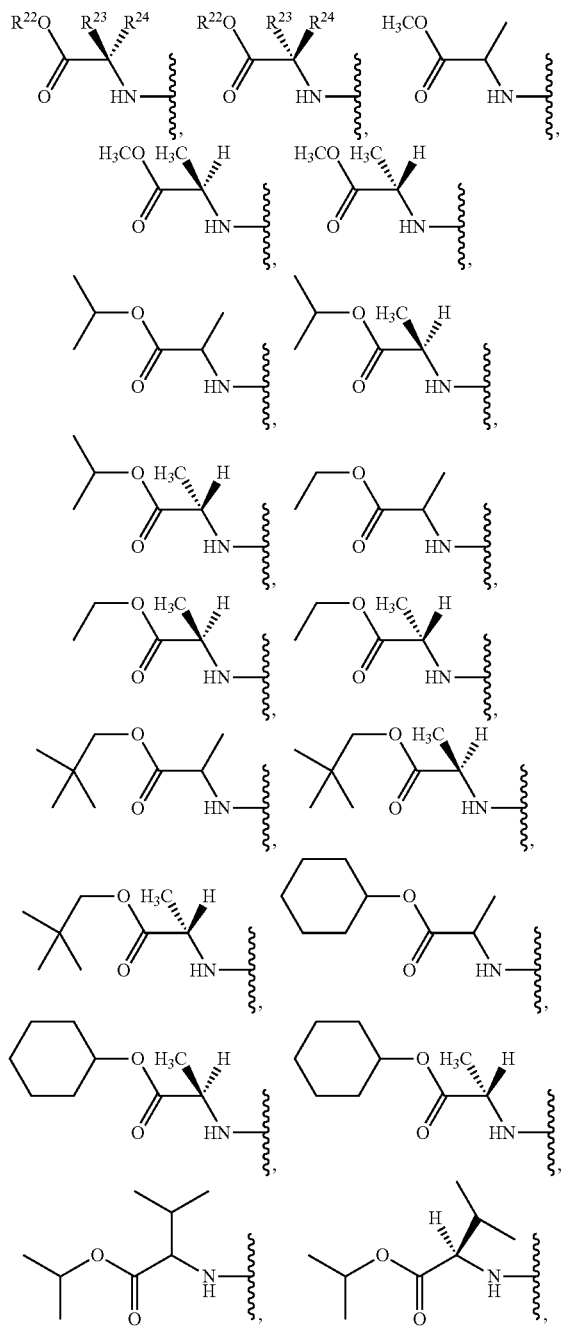

-continued

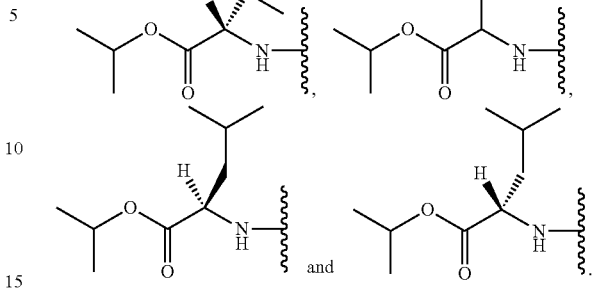

The substituents attached to the 5'-position of a compound of Formula (A) can vary. In some embodiments, $R^{3a}$ and $R^{3b}$ can be the same. In other embodiments, $R^{3a}$ and $R^{3b}$ can be different. In some embodiments, $R^{3a}$ and $R^{3b}$ can be both hydrogen. In some embodiments, at least one of $R^{3a}$ and $R^{3b}$ can be an optionally substituted $C_{1-6}$-alkyl; and the other of $R^{3a}$ and $R^{3b}$ can be hydrogen. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In an embodiment, at least one of $R^{3a}$ and $R^{3b}$ can be methyl, and the other of $R^{3a}$ and $R^{3b}$ can be hydrogen. In other embodiments, at least one of $R^{3a}$ and $R^{3b}$ can be an optionally substituted $C_{1-6}$-haloalkyl, and the other of $R^{3a}$ and $R^{3b}$ can be hydrogen. One example of a suitable optionally substituted $C_{1-6}$-haloalkyl is $CF_3$. In other still embodiments, $R^{3a}$ and $R^{3b}$ can be taken together to form an optionally substituted $C_{3-6}$ cycloalkyl. When the substituents attached to the 5'-carbon make the 5'-carbon chiral, in some embodiments, the 5'-carbon can be a (R)-stereocenter. In other embodiments, the 5'-carbon can be an (S)-stereocenter.

The substituents attached to the 4'-carbon can vary. In some embodiments, $R^4$ can be hydrogen. In other embodiments, $R^4$ can be azido. In still other embodiments, $R^4$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^4$ can be an optionally substituted $C_{2-6}$ alkenyl. In some embodiments, $R^4$ can be an optionally substituted $C_{2-6}$ alkynyl.

The substituents attached to the 2'-carbon and the 3'-carbon can also vary. In some embodiments, $R^5$ can be hydrogen. In other embodiments, $R^5$ can be halogen. In still other embodiments, $R^5$ can be azido. In yet still other embodiments, $R^5$ can be cyano. In some embodiments, $R^5$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In other embodiments, $R^5$ can be —$OR^{10}$, wherein $R^{10}$ can be hydrogen. In still other embodiments, $R^5$ can be —$OR^{10}$, wherein $R^{10}$ can be an optionally substituted $C_{1-6}$ alkyl. In yet still other embodiments, $R^5$ can be —$OC(=O)R^{11}$, wherein $R^H$ can be an optionally substituted $C_{1-6}$ alkyl or an optionally substituted $C_{3-6}$ cycloalkyl. Examples of suitable $C_{1-6}$ alkyls and $C_{3-6}$ cycloalkyls are described herein.

In some embodiments, $R^6$ can be hydrogen. In other embodiments, $R^6$ can be halogen. In still other embodiments, $R^6$ can be azido. In yet still other embodiments, $R^6$ can be cyano. In some embodiments, $R^6$ can be an optionally substituted $C_{1-6}$ alkyl. In other embodiments, $R^6$ can be —$OR^{12}$, wherein $R^{12}$ can be hydrogen. In still other embodiments, $R^6$ can be —$OR^{12}$, wherein $R^{12}$ can be an optionally substituted $C_{1-6}$ alkyl. A non-limiting list of examples of $R^6$ being —$OR^{12}$, wherein $R^{12}$ can be an optionally substituted $C_{1-6}$ alkyl are methoxy, ethoxy, n-propoxy, isopropoxy, n-butoxy, isobutoxy and tert-butoxy, pentoxy (straight-chained or branched) and hexoxy (straight-chained or branched). In yet still other embodiments, $R^6$ can be —$OC(=O)R^{13}$, wherein $R^{13}$ can be an optionally substituted $C_{1-6}$ alkyl or an optionally substituted $C_{3-6}$ cycloalkyl. Examples of suitable optionally substituted $C_{1-6}$ alkyls include optionally substituted variants of the following: methyl, ethyl, n-propyl, isopropyl, n-butyl, isobutyl, tert-butyl pentyl (branched and straight-chained), and hexyl (branched and straight-chained). Examples of suitable optionally substituted $C_{3-6}$ cycloalkyls include optionally substituted variants of the following: cyclopropyl, cyclobutyl, cyclopentyl and cyclohexyl.

In some embodiments, $R^7$ can be hydrogen. In other embodiments, $R^7$ can be halogen. In still other embodiments, $R^7$ can be azido. In yet still other embodiments, $R^7$ can be cyano. In some embodiments, $R^7$ can be an optionally substituted $C_{1-6}$ alkyl. In other embodiments, $R^7$ can be —$OR^{14}$. In an embodiment, when $R^{14}$ is hydrogen, $R^7$ can be a hydroxy group. In still other embodiments, when $R^{14}$ is an optionally substituted $C_{1-6}$ alkyl, $R^7$ can be an optionally substituted $C_{1-6}$ alkoxy. Examples, of $R^7$ being —$OR^{14}$, wherein $R^{14}$ can be an optionally substituted $C_{1-6}$ alkyl include, but are not limited to, are methoxy, ethoxy, n-propoxy, isopropoxy, n-butoxy, isobutoxy, tert-butoxy, pentoxy (straight-chained or branched) and hexoxy (straight-chained or branched). In yet still other embodiments, $R^7$ can be —$OC(=O)R^{15}$, wherein $R^{15}$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^7$ can be —$OC(=O)R^{15}$, wherein $R^{15}$ can be an optionally substituted $C_{3-6}$ cycloalkyl In some embodiments, $R^8$ can be hydrogen. In other embodiments, $R^8$ can be halogen. In still other embodiments, $R^8$ can be azido. In yet still other embodiments, $R^8$ can be cyano. In some embodiments, $R^8$ can be –$OR^{16}$. When $R^{16}$ is hydrogen, $R^8$ can be hydroxy. Alternatively, when $R^{16}$ is an optionally substituted $C_{1-6}$ alkyl, $R^8$ can be an optionally substituted $C_{1-6}$ alkoxy. Suitable alkoxy groups are described herein. In other embodiments, $R^8$ can be an optionally substituted $C_{1-6}$ alkyl. In still other embodiments, $R^8$ can be —$OC(=O)R^{17}$ in which $R^{17}$ is an optionally substituted $C_{1-6}$ alkyl. In yet still other embodiments, $R^8$ can be —$OC(=O)R^{17}$ in which $R^{17}$ is an optionally substituted $C_{3-6}$ cycloalkyl. Examples of suitable $C_{1-6}$ alkyl and $C_{3-6}$ cycloalkyl groups are described herein.

In some embodiments, $R^6$ and $R^7$ can both be hydroxy. In still other embodiments, $R^6$ and $R^7$ can both be both oxygen atoms and linked together by a carbonyl group, for example, —O—C(=O)—O—. In some embodiments, at least one of $R^7$ and $R^8$ can be a halogen. In some embodiments, $R^7$ and $R^8$ can both be a halogen. In other embodiments, $R^7$ can be a halogen and $R^8$ can be an optionally substituted $C_{1-6}$ alkyl, such as those described herein. In other embodiments, $R^7$ can be hydrogen and $R^8$ can be a halogen. In still other embodiments, at least one of $R^6$ and $R^7$ can be a hydroxy and $R^8$ can be an optionally substituted $C_{1-6}$ alkyl. In yet still other embodiments, $R^6$ can be hydroxy, $R^7$ can be hydroxy, H or halogen, and $R^8$ can be an optionally substituted $C_{1-6}$ alkyl. In some embodiments, $R^{3a}$, $R^{3b}$, $R^4$, $R^5$ and $R^9$ can be hydrogen in any of the embodiments described in this paragraph. In some embodiments, $B^1$ can be an optionally substituted adenine, an optionally substituted guanine, and optionally substituted thymine, optionally substituted cytosine, or an optionally substituted uracil in any of the embodiments described in this paragraph.

In some embodiments, $R^9$ can be hydrogen. In other embodiments, $R^9$ can be azido. In still other embodiments, $R^9$ can be cyano. In yet still other embodiments, $R^9$ can be an optionally substituted $C_{1-6}$ alkyl, such as those described herein. In some embodiments, $R^9$ can be —$OR^{18}$. In some embodiments, when $R^9$ is —$OR^{18}$, $R^9$ can be a hydroxy group. In other embodiments, when $R^9$ is —$OR^{18}$, $R^9$ can be an optionally substituted $C_{1-6}$ alkoxy. Examples of optionally substituted $C_{1-6}$ alkoxy include the following: methoxy, ethoxy, n-propoxy, isopropoxy, n-butoxy, isobutoxy, tert-butoxy, pentoxy (branched and straight-chained), and hexoxy (branched and straight-chained).

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

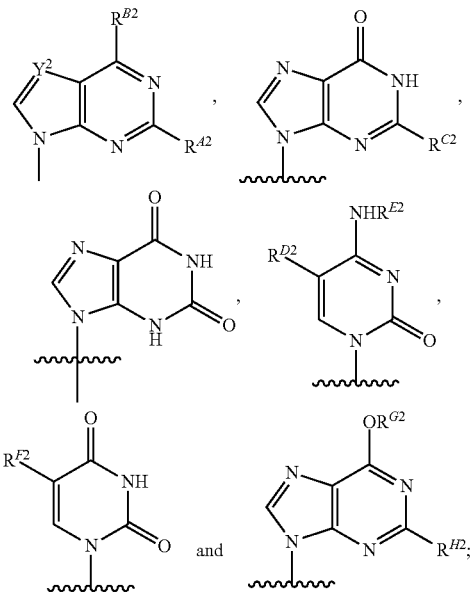

wherein: $R^{A2}$ can be selected from hydrogen, halogen and $NHR^{J2}$, wherein $R^{J2}$ can be selected from hydrogen, —$C(=O)R^{K2}$ and —$C(=O)OR^{L2}$; $R^{B2}$ can be halogen or $NHR^{W2}$, wherein $R^{W2}$ is selected from hydrogen, an optionally substituted $C_{1-6}$ alkyl, an optionally substituted $C_{2-6}$ alkenyl, an optionally substituted $C_{3-8}$ cycloalkyl, —$C(=O)R^{M2}$ and —$C(=O)OR^{N2}$; $R^{C2}$ can be hydrogen or $NHR^{O2}$, wherein $R^{O2}$ can be selected from hydrogen, —$C(=O)R^{P2}$ and —$C(=O)OR^{Q2}$; $R^{D2}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{E2}$ can be selected from hydrogen, an optionally substituted $C_{1-6}$ alkyl, an optionally substituted $C_{3-8}$ cycloalkyl, —C(=O)$R^{R2}$ and —C(=O)O$R^{S2}$; $R^{F2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^2$ can be N (nitrogen) or $CR^{J2}$, wherein $R^{J2}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{G2}$ can be an optionally substituted $C_{1-6}$ alkyl; $R^{H2}$ can be hydrogen or NH$R^{T2}$, wherein $R^{T2}$ can be independently selected from hydrogen, —C(=O)$R^{U2}$ and —C(=O)O$R^{V2}$, and $R^{K2}$, $R^{L2}$; $R^{M2}$, $R^{N2}$, $R^{P2}$, $R^{Q2}$, $R^{R2}$, $R^{S2}$, $R^{U2}$ and $R^{V2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloalkynyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl). In some embodiments, the structures shown above can be modified by replacing one or more hydrogens with substituents selected from the list of substituents provided for the definition of "substituted." Suitable optionally substituted $C_{1-6}$ alkyl groups that can be present on an optionally substituted heterocyclic base or an optionally substituted heterocyclic base with one or more protected amino groups are described herein, and include, optionally substituted variants of the following: methyl, ethyl, n-propyl, isopropyl, n-butyl, isobutyl, tert-butyl, pentyl (branched and straight-chained), and hexyl (branched and straight-chained).

In some embodiments, $B^1$ can be selected from adenine, guanine, thymine, cytosine and uracil. In some embodiments, $R^{B2}$ can be NH$_2$. In other embodiments, $R^{E2}$ can be hydrogen. In some embodiments, $B^1$ can be

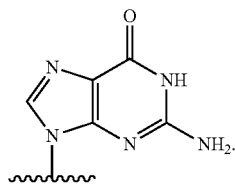 [SMILES: *n1cnc2c(=O)[nH]c(N)nc21]

In other embodiments, $B^1$ can be

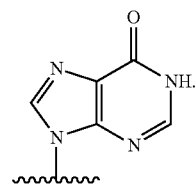 [SMILES: *n1cnc2c(=O)[nH]cnc21]

In some embodiments, $B^1$ can be

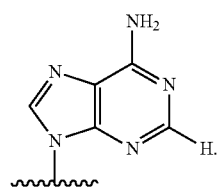

In some embodiments, $B^1$ can be

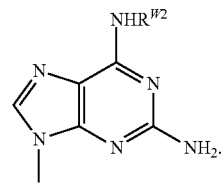

In still other embodiments, $B^1$ can be

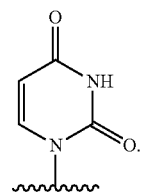 [SMILES: *n1ccc(=O)[nH]c1=O]

In yet still other embodiments, $B^1$ can be

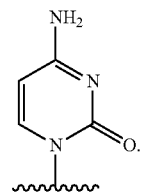 [SMILES: *n1ccc(N)nc1=O]

In some embodiments, $B^1$ can be

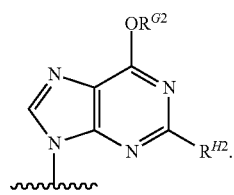

In some embodiments, when $R^2$ is a substituted or unsubstituted phenyl, then $R^1$ cannot be

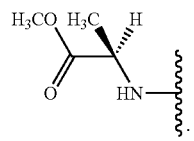

In other embodiments, when $R^2$ is a substituted or unsubstituted phenyl, then $R^1$ cannot be

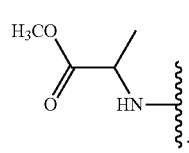 [SMILES: *NC(C)C(=O)OC]

In still other embodiments, when $R^2$ is a substituted or unsubstituted phenyl and $R^1$ is

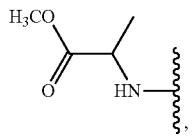

then at least one of $R^5$ and $R^6$ cannot be hydroxy.

In some embodiments, when $R^1$ is $O^-$ or OH, then $R^2$ cannot be

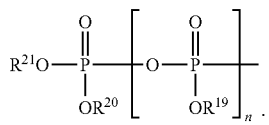

In some embodiments, at least one of $R^{3a}$ and $R^{3b}$ cannot be hydrogen. In some embodiments, $R^4$ is not azido. In some embodiments, when $R^4$ is not azido, then $R^7$ and $R^8$ are not both halogen. In some embodiments, when $R^4$ is azido, then $B^1$ is not an optionally substituted uracil, optionally substituted uracil with one or more protected amino groups, an optionally substituted cytosine or optionally substituted cytosine with one or more protected amino groups. In some embodiments, $R^6$ cannot be azido. In some embodiments, when $R^1$ is a methyl ester of glycine, alanine, valine, or phenylalanine; $R^2$ is p-chlorophenyl or p-nitrophenyl; $B^1$ is thymine; and $R^{3a}$, $R^{3b}$, $R^4$, $R^5$, $R^7$, $R^8$, and $R^9$ are all hydrogen; then $R^6$ cannot be azido. In some embodiments, at least one of $R^6$ and $R^7$ cannot be hydroxy. For example, $R^6$ cannot be hydroxy, $R^7$ cannot be hydroxy, or both of $R^6$ and $R^7$ cannot be hydroxy.

Some embodiments disclosed herein relate to a compound of Formula (A) or a pharmaceutically acceptable salt thereof, wherein: $B^1$ can be an optionally substituted heterocyclic base as described above; $R^1$ can be selected from $O^-$, OH, an optionally substituted N-linked amino acid and an optionally substituted N-linked amino acid ester derivative: $R^2$ can be selected from an optionally substituted aryl and

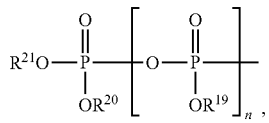

wherein $R^{19}$, $R^{20}$ and $R^{21}$ can be independently absent or hydrogen, and n can be 0 or 1; provided that when $R^1$ is $O^-$ or OH, then $R^2$ is

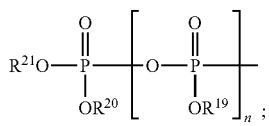

$R^{3a}$ and $R^{3b}$ can be hydrogen; $R^4$ can be hydrogen; $R^5$ can be selected from hydrogen, halogen, an optionally substituted $C_{1-6}$ alkyl and $-OR^{10}$; $R^6$ can be selected from hydrogen, halogen, optionally substituted $C_{1-6}$ alkyl, $-OR^{12}$ and $-OC(=O)R^{13}$; $R^7$ can be selected from hydrogen, halogen, azido, cyano, an optionally substituted $C_{1-6}$ alkyl, $-OR^{14}$ and $-OC(=O)R^{15}$; or $R^6$ and $R^7$ can be both oxygen atoms and linked together by a carbonyl group; $R^8$ can be selected from hydrogen, halogen, an optionally substituted $C_{1-6}$ alkyl and $-OR^{16}$; $R^9$ can be hydrogen; $R^{10}$, $R^{12}$, $R^{14}$ and $R^{16}$ can be independently selected from hydrogen and an optionally substituted $C_{1-6}$ alkyl; and $R^{13}$ and $R^{15}$ can be independently selected from an optionally substituted $C_{1-6}$ alkyl and an optionally substituted $C_{3-6}$ cycloalkyl.

Some embodiments disclosed herein relate to a compound of Formula (A) or a pharmaceutically acceptable salt thereof, wherein: $B^1$ can be an optionally substituted heterocyclic base or an optionally substituted heterocyclic base with a protected amino group selected from

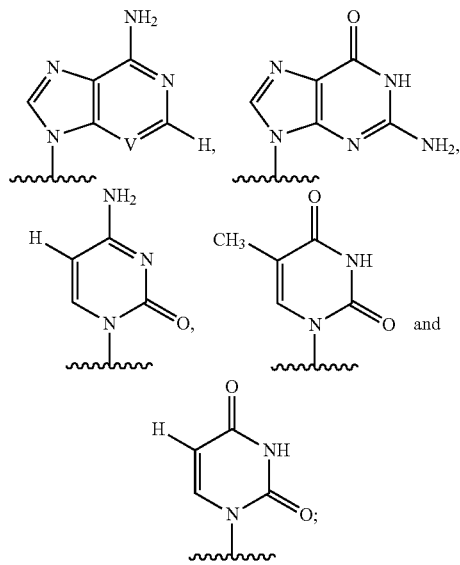

$R^1$ can be selected from $O^-$, OH, an optionally substituted N-linked amino acid and an optionally substituted N-linked amino acid ester derivative; $R^2$ can be selected from an optionally substituted aryl and

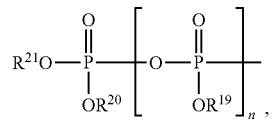

wherein $R^{19}$, $R^{20}$ and $R^{21}$ can be independently absent or hydrogen, and n can be 0 or 1; provided that when $R^1$ is $O^-$ or OH, then $R^2$ is

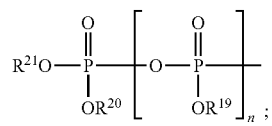

$R^{3a}$ and $R^{3b}$ can be hydrogen; $R^4$ can be hydrogen; $R^5$ can be selected from hydrogen, halogen, an optionally substituted $C_{1-6}$ alkyl and $-OR^{10}$; $R^6$ can be selected from hydrogen, halogen, optionally substituted $C_{1-6}$ alkyl, —$OR^{12}$ and —OC(=O)$R^{13}$; $R^7$ can be selected from hydrogen, halogen, azido, cyano, an optionally substituted $C_{1-6}$ alkyl, —$OR^{14}$ and —OC(=O)$R^{15}$; or $R^6$ and $R^7$ can be both oxygen atoms and linked together by a carbonyl group; $R^8$ can be selected from hydrogen, halogen, an optionally substituted $C_{1-6}$ alkyl and —$OR^{16}$; $R^9$ can be hydrogen; $R^{10}$, $R^{12}$, $R^{14}$ and $R^{16}$ can be independently selected from hydrogen and an optionally substituted $C_{1-6}$ alkyl; and $R^{13}$ and $R^{15}$ can be independently selected from an optionally substituted $C_{1-6}$ alkyl and an optionally substituted $C_{3-6}$ cycloalkyl.

In some embodiments, Formula (A) can be a compound of Formula (Iα), wherein: $B^1$ can be an optionally substituted heterocyclic base or an optionally substituted heterocyclic base with a protected amino group selected from cytosine, uridine, thymidine, guanine and adenine; $R^1$ can be selected from O⁻, OH, and an optionally substituted N-linked amino acid ester derivative of alanine, valine, or leucine; $R^2$ can be selected from an optionally substituted phenyl, an optionally substituted naphthyl, an optionally substituted pyridyl, an optionally substituted quinolyl, and

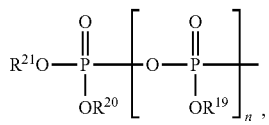

wherein $R^{19}$, $R^{20}$ and $R^{21}$ independently can be hydrogen or absent, and n can be 0 or 1; provided that when $R^1$ is O⁻ or OH, then $R^2$ is

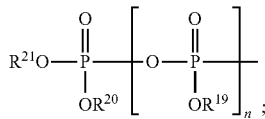

$R^{3a}$ and $R^{3b}$ can be hydrogen; $R^4$ can be hydrogen; $R^5$ can be hydrogen; $R^6$ can be —$OR^{12}$ or —OC(=O)$R^{13}$; $R^7$ can be selected from halogen, —$OR^{14}$ and —OC(=O)$R^{15}$; $R^8$ can be an optionally substituted $C_{1-6}$ alkyl; $R^9$ can be hydrogen; $R^{12}$ and $R^{14}$ can be independently hydrogen or an optionally substituted $C_{1-6}$ alkyl; and $R^{13}$ and $R^{15}$ can be independently an optionally substituted $C_{1-6}$ alkyl.

Some embodiments relate to a compound of Formula (A) or a pharmaceutically acceptable salt thereof, wherein: $B^1$ can be an optionally substituted heterocyclic base or an optionally substituted heterocyclic base with a protected amino group; $R^1$ can be selected from O⁻, OH, an optionally substituted N-linked amino acid and an optionally substituted N-linked amino acid ester derivative; $R^2$ can be selected from an optionally substituted aryl, an optionally substituted heteroaryl, an optionally substituted heterocyclyl and

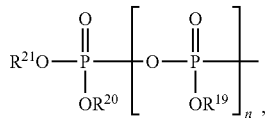

wherein $R^{19}$, $R^{20}$ and $R^{21}$ can be independently absent or hydrogen, and n can be 0 or 1; provided that when $R^1$ is O⁻ or OH, then $R^2$ is

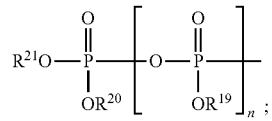

$R^{3a}$ and $R^{3b}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{3a}$ and $R^{3b}$ can be taken together to form an optionally substituted $C_{3-6}$ cycloalkyl; $R^4$ can be selected from hydrogen, azido, an optionally substituted $C_{1-6}$ alkyl, an optionally substituted $C_{2-6}$ alkenyl and an optionally substituted $C_{2-6}$ alkynyl; $R^5$ can be selected from hydrogen, halogen, azido, cyano, an optionally substituted $C_{1-6}$ alkyl, —$OR^{10}$ and —OC(=O)$R^{11}$; $R^6$ can be selected from hydrogen, halogen, azido, cyano, an optionally substituted $C_{1-6}$ alkyl, —$OR^{12}$ and —OC(=O)$R^{13}$; $R^7$ can be selected from hydrogen, halogen, azido, cyano, an optionally substituted $C_{1-6}$ alkyl, —$OR^{14}$ and —OC(=O)$R^{15}$; or $R^6$ and $R^7$ can be both oxygen atoms and linked together by a carbonyl group; $R^8$ can be selected from hydrogen, halogen, azido, cyano, an optionally substituted $C_{1-6}$ alkyl, —$OR^{16}$ and —OC(=O)$R^{17}$; $R^9$ can be selected from hydrogen, azido, cyano, an optionally substituted $C_{1-6}$ alkyl and —$OR^{18}$; $R^{10}$, $R^{12}$, $R^{14}$, $R^{16}$ and $R^{18}$ can be independently selected from hydrogen and an optionally substituted $C_{1-6}$ alkyl; and $R^{11}$, $R^{13}$, $R^{15}$ and $R^{17}$ can be independently an optionally substituted $C_{1-6}$ alkyl and an optionally substituted $C_{3-6}$ cycloalkyl.

In some embodiments, a compound of Formula (A) can be a single diastereomer. In other embodiments, a compound of Formula (A) can be a mixture of diastereomers. In some embodiments, a compound of Formula (A) can be a 1:1 mixture of two diastereomers. In some embodiments, a compound of Formula (A) can be diasteriometrically enriched (for example, one diastereomer can be present at a concentration of >55%, ≥75%, ≥80%, ≥90%, ≥95%, ≥98%, or ≥99% as compared to the total concentration of the other diastereomers).

Examples of compounds of Formula (A) are provided in FIG. 1.

Compounds of Formula (C)

Compounds of Formula (C) are therapeutic compounds that include HCV protease inhibitors, nucleoside HCV polymerase inhibitors, non-nucleoside HCV polymerase inhibitors, NS5A inhibitors, and other antivirals. Examples of compounds of Formula (C) are provided in FIG. 2.

Pharmaceutical Activity

In some embodiments, a composition comprising a compound of Formula (A), or a pharmaceutically acceptable salt, hydrate, or solvate thereof, can act as a chain terminator of HCV replication. For example, incorporation of compound of Formula (A) containing a moiety at the 2'-carbon position can terminate further elongation of the RNA chain of HCV. For example, a compound of Formula (A) can contain a 2'-carbon modification when $R^8$ of Formula (A) is a non-hydrogen group selected from halogen or an optionally substituted $C_{1-6}$ alkyl.

In some embodiments, a composition containing a compound of Formula (A), or a pharmaceutically acceptable salt, hydrate, or solvate thereof, can have increased metabolic and/or plasma stability. In some embodiments, a composition containing a compound of Formula (A), or a pharmaceutically acceptable salt, hydrate, or solvate of the aforementioned compounds. A non-limiting list of example properties include, but are not limited to, increased biological half life, increased bioavailability, increase potency, a sustained in vivo response, increased dosing intervals, decreased dosing amounts, decreased cytotoxicity, reduction in required amounts for treating disease conditions, reduction in viral load, reduction in time to seroreversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a composition containing a compound of Formula (A), or a pharmaceutically acceptable salt, hydrate, or solvate thereof, can have a biological half life of greater than 24 hours, e.g., a biological half life in the range of about 40 to 46 hours for some compounds of Formula (A). In some embodiments, a composition containing a compound of Formula (A), or a pharmaceutically acceptable salt, hydrate, or solvate thereof, can have more potent antiviral activity (for example, a lower $IC_{50}$ in an HCV replicon assay) as compared to the current standard of care.

Pharmaceutical Compositions

In some embodiments, a pharmaceutical composition can include a single diastereomer of a compound of Formula (A), or a pharmaceutically acceptable salt, hydrate, or solvate thereof, (for example, a single diastereomer is present in the pharmaceutical composition at a concentration of greater than 99% compared to the total concentration of the other diastereomers). In other embodiments, a pharmaceutical composition can include a mixture of diastereomers of a compound of Formula (A), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, a pharmaceutical composition includes a 1:1 mixture of two diastereomers of a compound of Formula (A), or a pharmaceutically acceptable salt, hydrate, or solvate thereof.

The term "pharmaceutical composition" refers to a mixture of one or more compounds disclosed herein with one or more chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

Figure 2:
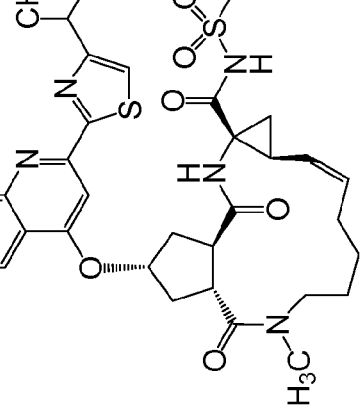
FIG. 2 shows example compounds of Formula (C), including Compounds 3000 through 3067, which include HCV protease inhibitors, nucleoside HCV polymerase inhibitors, non-nucleoside HCV polymerase inhibitors, NS5A inhibitors, and other antivirals.
Figure 2:
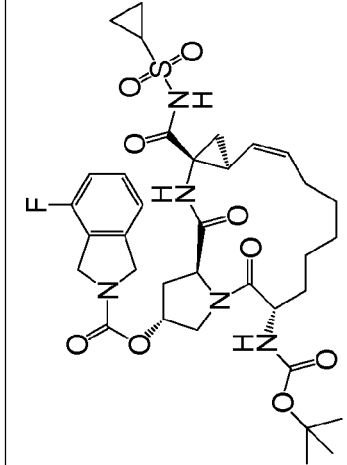
Figure 2:
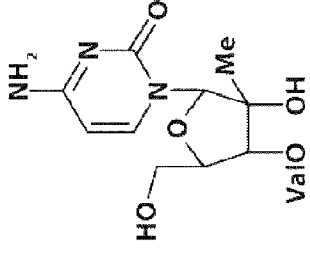
Figure 2:
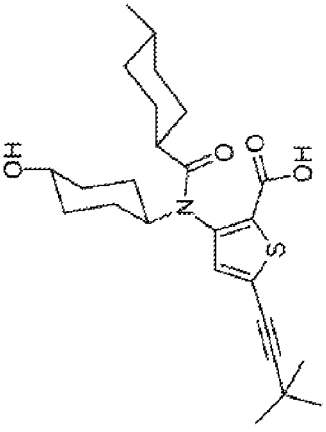
Figure 2:
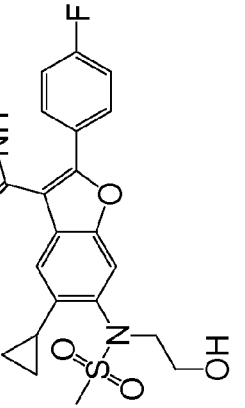
Figure 2:
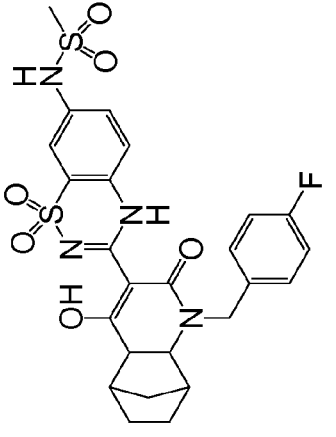
Figure 2:
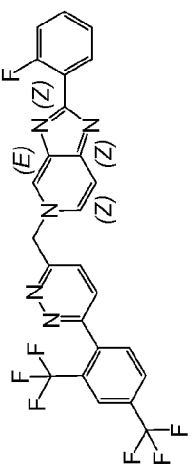
Figure 2:
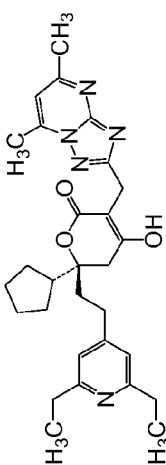
Figure 2:
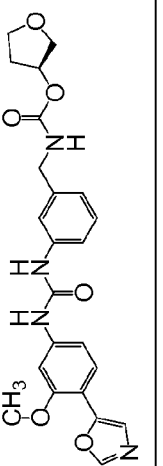
Figure 2:
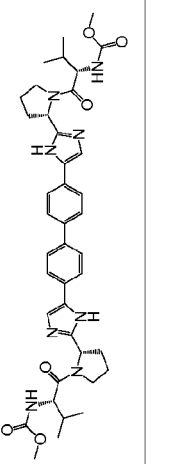
Figure 2:
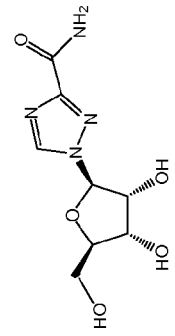

Combination therapies contemplated include use of a compound of Formula (A) selected from those listed in FIG. 1 and a compound (e.g., an HCV protease inhibitor, nucleoside HCV polymerase inhibitor, non-nucleoside HCV polymerase inhibitor, NS5A inhibitor, or other antiviral) selected from those listed in FIG. 2, or a pharmaceutically acceptable salt, hydrate, or solvate of the aforementioned compounds. Other combination therapies contemplated include use of a compound of Formula (A) selected from those listed in FIG. 1 and a compound of Formula (C) selected from 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. Other combination therapies contemplated include use of a compound selected from Compound 1000 through Compound 1032 and a compound selected from 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds.

Combination therapies also contemplated include use of a compound of Formula (A) selected from those listed in FIG. 1 and two different compounds of Formula (C) (e.g., HCV protease inhibitors, nucleoside HCV polymerase inhibitors, non-nucleoside HCV polymerase inhibitors, NS5A inhibitors, or other antivirals) selected from those listed in FIG. 2, or a pharmaceutically acceptable salt, hydrate, or solvate of the aforementioned compounds. Other combination therapies contemplated include use of a compound selected from Compound 1000 through Compound 1032 and two different compounds selected from Compound 3000 through Compound 3067. Still other combination therapies contemplated include use of a compound of Formula (A) selected from those listed in FIG. 1, a first compound of Formula (C) (e.g., HCV protease inhibitors, nucleoside HCV polymerase inhibitors, non-nucleoside HCV polymerase inhibitors, NS5A inhibitors, or other antivirals) selected from those listed in FIG. 2 and a second compound of Formula (C) selected from those listed in FIG. 2, or a pharmaceutically acceptable salt, hydrate, or solvate of the aforementioned compounds, wherein the first compound of Formula (C) and the second compound of Formula (C) are different. Yet still other combination therapies contemplated include use of a compound selected from Compound 1000 through Compound 1032; a first compound selected from Compound 3000 through Compound 3067; and a second compound selected from Compound 3000 through Compound 3067, or a pharmaceutically acceptable salt, hydrate, or solvate of the aforementioned compounds, wherein the first compound selected from Compound 3000 through Compound 3067 is different from the second compound selected from Compound 3000 through Compound 3067.

The pharmaceutically active ingredients of the combination therapy can be contained in a single unit dosage form, in two unit dosage forms, or in three unit dosage forms.

In some embodiments, a single unit dosage form can be provided containing a compound of Formula (A) selected from those listed in FIG. 1 and a compound of Formula (C) selected from those listed in FIG. 2, or a pharmaceutically acceptable salt, hydrate, or solvate of the aforementioned compounds. In some embodiments, a single unit dosage form can be provided containing a compound of Formula (A) selected from those listed in FIG. 1 and two different compounds of Formula (C) selected from those listed in FIG. 2, or a pharmaceutically acceptable salt, hydrate, or solvate of the aforementioned compounds.

In some embodiments, two unit dosage forms can be provided, with one containing a compound of Formula (A) selected from those listed in FIG. 1 and the other containing a compound of Formula (C) selected from those listed in FIG. 2, or a pharmaceutically acceptable salt, hydrate, or solvate of the aforementioned compounds. In some embodiments, two unit dosage forms can be provided, with one containing a compound of Formula (A) selected from those listed in FIG. 1, and the other containing two different compounds of Formula (C) selected from those listed in FIG. 2, or a pharmaceutically acceptable salt, hydrate, or solvate of the aforementioned compounds. In some embodiments, two unit dosage forms can be provided, with one containing a compound of Formula (A) selected from those listed in FIG. 1 and a first compound of Formula (C) selected from those listed in FIG. 2, and the other containing a second compound of Formula (C) selected from those listed in FIG. 2, or a pharmaceutically acceptable salt, hydrate, or solvate of the aforementioned compounds, wherein the first and second compound are not the same.

In some embodiments, three unit dosage forms can be provided, with one unit dosage form containing a compound of Formula (A) selected from those listed in FIG. 1 and two additional unit dosage forms, each containing a different compound of Formula (C) selected from those listed in FIG. 2, or a pharmaceutically acceptable salt, hydrate, or solvate of the aforementioned compounds.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound or a composition exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound or composition in a local rather than systemic manner, for example, via injection of the compound or composition directly into the infected area, often in a depot or sustained release formulation. Furthermore, one may administer the compound or composition in a targeted drug delivery system, for example, in a liposome coated with a tissue-specific antibody. The liposomes can be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include one or more compounds described herein formulated in a compatible pharmaceutical carrier may also be prepared, placed in an appropriate container, and labeled for treatment of an indicated condition.

Methods of Use

Some embodiments disclosed herein relate to a method of treating and/or ameliorating a disease or condition that can include administering to a subject an effective amount of a combination of compounds described herein. In some embodiments, such methods include administering an effective amount of a combination of a compound of Formula (A), and one or more compounds of Formula (C) selected from those listed in FIG. 2, or a pharmaceutically acceptable salt, hydrate, or solvate of the aforementioned compounds. In some embodiments, such methods include administering an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In some embodiments, such methods include administering an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In some embodiments, such methods include administering an effective amount of a combination of a compound selected from Compound 1000 through Compound 1032 and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, such methods include administering an effective amount of a combination of a compound of Formula (A), a first compound of Formula (C) and a second compound of Formula (C), or a pharmaceutically acceptable salt, hydrate, or solvate of the aforementioned compounds, wherein the first compound of Formula (C) is different from the second of Formula (C). In some embodiments, such methods include administering an effective amount of a combination of a compound selected from Compound 1000 through Compound 1032, a first compound selected from Compound 3000 through Compound 3067 and a second compound selected from Compound 3000 through Compound 3067, or a pharmaceutically acceptable salt, hydrate, or solvate of the aforementioned compounds, wherein the first compound selected from Compound 3000 through Compound 3067 is different from the second compound selected from Compound 3000 through Compound 3067.

Other embodiments disclosed herein relates to a method of ameliorating or treating a viral infection that can include administering an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, the viral infection can be caused by a virus selected from an adenovirus, an Alphaviridae, an Arbovirus, an Astrovirus, a Bunyaviridae, a Coronaviridae, a Filoviridae, a Flaviviridae, a Hepadnaviridae, a Herpesviridae, an Alphaherpesvirinae, a Betaherpesvirinae, a Gammaherpesvirinae, a Norwalk Virus, an Astroviridae, a Caliciviridae, an Orthomyxoviridae, a Paramyxoviridae, a Paramyxoviruses, a Rubulavirus, a Morbillivirus, a Papovaviridae, a Parvoviridae, a Picornaviridae, an Aphthoviridae, a Cardioviridae, an Enteroviridae, a Coxsackie virus, a Polio Virus, a Rhinoviridae, a Phycodnaviridae, a Poxyiridae, a Reoviridae, a Rotavirus, a Retroviridae, an A-Type Retrovirus, an Immunodeficiency Virus, a Leukemia Viruses, an Avian Sarcoma Viruses, a Rhabdoviruses, a Rubiviridae, a Togaviridae an Arenaviridae and/or a Bornaviridae. In some embodiments, the viral infection can be a hepatitis C viral (HCV) infection. HCV is an enveloped positive strand RNA virus in the Flaviviridae family. There are various nonstructural proteins of HCV, such as NS2, NS3, NS4, NS4A, NS4B, NS5A, and NS5B. NS5B is believed to be an RNA-dependent RNA polymerase involved in the replication of HCV RNA.

Some embodiments disclosed herein relate to methods of ameliorating and/or treating a viral infection (for example, an HCV infection) that can include contacting a cell infected with the virus with an effective amount of a combination of compounds described herein. Other embodiments described herein relate to using a combination of compounds described herein in the manufacture of a medicament for ameliorating and/or treating a viral infection (for example, an HCV infection) that can include contacting a cell infected with the virus with an effective amount of said combination of compounds described herein. Still other embodiments described herein relate to a combination of compounds described herein that can be used for ameliorating and/or treating a viral infection (for example, an HCV infection) by contacting a cell infected with the virus with an effective amount of said combination of compounds described herein. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

Some embodiments disclosed herein relate to methods of inhibiting replication of a virus (such as a hepatitis C virus) that can include contacting a cell infected with the virus with an effective amount of a combination of compounds described herein. Other embodiments described herein relate to using a combination of compounds described herein in the manufacture of a medicament for inhibiting replication of a virus (such as a hepatitis C virus) that can include contacting a cell infected with the virus with an effective amount of said combination of compounds. Still other embodiments described herein relate to a combination of compounds described herein that can be used for inhibiting replication of a virus (such as a hepatitis C virus) by contacting a cell infected with the virus with an effective amount of said combination of compounds. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

Some embodiments described herein relate to a method of inhibiting an RNA dependent RNA polymerase can include contacting a cell (for example, a cell infected with HCV) with an effective amount of a combination of compounds described herein. Other embodiments described herein relate to using a combination of compounds described herein in the manufacture of a medicament for inhibiting an RNA dependent RNA polymerase that can include contacting a cell (for example, a cell infected with HCV) with an effective amount of said combination of compounds. Still other embodiments described herein relate to a combination of compounds described herein that can be used for inhibiting an RNA dependent RNA polymerase that can include contacting a cell (for example, a cell infected with HCV) with an effective amount of said combination of compounds. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

Some embodiments described herein relate to a method of inhibiting NS5B polymerase activity that can include contacting a cell (for example, a cell infected with HCV) with an effective amount of a combination of compounds described herein. Other embodiments described herein relate to using a combination of compounds described herein in the manufacture of a medicament for inhibiting NS5B polymerase activity that can include contacting a cell (for example, a cell infected with HCV) with an effective amount of said combination of compounds. Still other embodiments described herein relate to a combination of compounds described herein that can be used for inhibiting NS5B polymerase activity that can include contacting a cell (for example, a cell infected with HCV) with an effective amount of said combination of compounds. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

Some embodiments described herein relate to a method of inhibiting an HCV polymerase (for example, NS5B polymerase) can include contacting a cell (for example, a cell infected with HCV) with an effective amount of a combination of compounds described herein. Other embodiments described herein relate to using a combination of compounds described herein in the manufacture of a medicament for inhibiting an HCV polymerase (for example, NS5B polymerase) that can include contacting a cell (for example, a cell infected with HCV) with an effective amount of said combination of compounds. Still other embodiments described herein relate to a combination of compounds described herein that can be used for inhibiting an HCV polymerase (for example, NS5B polymerase) that can include contacting a cell (for example, a cell infected with HCV) with an effective amount of said combination of compounds. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

Some embodiments described herein relate to a method of ameliorating and/or treating HCV infection in a subject suffering from an HCV infection that can include administering to the subject an effective amount of a combination of compounds described herein. Other embodiments described herein relate to using a combination of compounds described herein in the manufacture of a medicament for ameliorating and/or treating HCV infection in a subject suffering from an HCV infection that can include administering to the subject an effective amount of said combination of compounds. Still other embodiments described herein relate to a combination of compounds described herein that can be used for ameliorating and/or treating HCV infection in a subject suffering from an HCV infection that can include administering to the subject an effective amount of said combination of compounds. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

Some embodiments described herein relate to a method of ameliorating and/or treating a condition selected from liver fibrosis, liver cirrhosis, and liver cancer in a subject suffering from one or more of the aforementioned liver conditions that can include administering an effective amount of a combination of compounds described herein. Other embodiments described herein relate to using a combination of compounds described herein in the manufacture of a medicament for ameliorating and/or treating a condition selected from liver fibrosis, liver cirrhosis, and liver cancer in a subject suffering from one or more of the aforementioned liver conditions that can include administering an effective amount of said combination of compounds. Still other embodiments described herein relate to a combination of compounds described herein that can be used for ameliorating and/or treating a condition selected from liver fibrosis, liver cirrhosis, and liver cancer in a subject suffering from one or more of the aforementioned liver conditions that can include administering an effective amount of said combination of compounds. In some embodiments, the one or more conditions selected from liver fibrosis, liver cirrhosis and liver cancer can be the result of an HCV infection. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

A cause of liver fibrosis, liver cirrhosis, and/or liver cancer can be an HCV infection. Some embodiments described herein relate to a method of increasing liver function in a subject having an HCV infection that can include administering to the subject an effective amount of a combination of compounds described herein. Other embodiments described herein relate to using a combination of compounds described herein in the manufacture of a medicament for increasing liver function in a subject having an HCV infection that can include administering to the subject an effective amount of said combination of compounds. Still other embodiments described herein relate to a combination of compounds described herein that can be used for increasing liver function in a subject having an HCV infection that can include administering to the subject an effective amount of said combination of compounds. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same.

Also contemplated is a method for reducing or eliminating further virus-caused liver damage in a subject having an HCV infection by administering an effective amount of a combination of compounds described herein. Other embodiments described herein relate to using a combination of compounds described herein in the manufacture of a medicament for reducing or eliminating further virus-caused liver damage in a subject having an HCV infection by administering an effective amount of said combination of compounds. Still other embodiments described herein relate to a combination of compounds described herein that can be used for reducing or eliminating further virus-caused liver damage in a subject having an HCV infection by administering an effective amount of said combination of compounds. In some embodiments, including those of this paragraph, the combination can include an effective amount of a combination of a compound of Formula (A) selected from those listed in FIG. 1, and one or more compounds of Formula (C) selected from those listed in FIG. 2, or a pharmaceutically acceptable salt, hydrate, or solvate of the aforementioned compounds. In some embodiments, including those of this paragraph, the combination can include an effective amount of a combination of a compound selected from Compound 1000 through Compound 1032, and one or more compounds selected from Compound 3000 through Compound 3067, or a pharmaceutically acceptable salt, hydrate, or solvate of the aforementioned compounds. In other embodiments, including those of this paragraph, the combination can include an effective amount of a combination of a compound of Formula (A) selected from those listed in FIG. 1, and a compound selected from Compound 3015, 3016, 3025, 3026, 3027, 3028, 3037, 3038, 3039, 3040, 3041, 3042, 3048, 3049, 3050, 3051, 3052, 3053, 3054, 3057, 3058, 3059, 3060, 3061, 3062, 3063, 3064, 3065 and 3067, or a pharmaceutically acceptable salt, hydrate, or solvate of the aforementioned compounds. In some embodiments, including those of this paragraph, the combination can include an effective amount of a combination of a compound of Formula (A) selected from those listed in FIG. 1, and two different compounds of Formula (C) selected from those listed in FIG. 2, or a pharmaceutically acceptable salt, hydrate, or solvate of the aforementioned compounds. In other embodiments, including those of this paragraph, the combination can include an effective amount of a combination of a compound selected from Compound 1000 through Compound 1032, and two different compounds selected from Compound 3000 through Compound 3067, or a pharmaceutically acceptable salt, hydrate, or solvate of the aforementioned compounds. In still other embodiments, including those of this paragraph, the combination can include an effective amount of a combination of a compound of Formula (A), a first compound of Formula (C), and a second compound of Formula (C), or a pharmaceutically acceptable salt, hydrate, or solvate of the aforementioned compounds, wherein the first compound of Formula (C) and the second compound of Formula (C) are not the same. In yet still other embodiments, including those of this paragraph, the combination can include an effective amount of a combination of a compound selected from Compound 1000 through Compound 1032, a first compound selected from Compound 3000 through Compound 3067, and a second compound selected from Compound 3000 through Compound 3067, or a pharmaceutically acceptable salt, hydrate, or solvate of the aforementioned compounds, wherein the first compound selected from Compound 3000 through Compound 3067 and the second compound selected from Compound 3000 through Compound 3067 are not the same. In some embodiments, this method or use can include slowing or halting the progression of liver disease. In other embodiments, the course of the liver disease can be reversed, and stasis or improvement in liver function can be achieved.

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4-e; 5a; 6a; 7a-7b; 8a-8b; 9a; 10a; and 11a). In some embodiments, a combination therapy as described herein can be effective to treat at least one genotype of HCV. In some embodiments, a combination therapy described herein (e.g., a combination therapy including a compound of Formula (A) selected from those listed in FIG. 1 and one or more compounds of Formula (C) selected from those listed in FIG. 2, or a pharmaceutically acceptable salt, hydrate, or solvate of the aforementioned compounds) can be effective to treat all 11 genotypes of HCV. In some embodiments, a combination therapy described herein (e.g., a combination therapy including a compound of Formula (A) selected from those listed in FIG. 1 and one or more compounds of Formula (C) listed in FIG. 2 can be effective to treat 3 or more, 5 or more, 7 or more of 9 more genotypes of HCV. In some embodiments, a combination therapy described herein (e.g., a combination therapy including a compound of Formula (A) selected from those listed in FIG. 1 and one or more compounds of Formula (C) listed in FIG. 2 is more effective against a larger number of HCV genotypes than the standard of care. In some embodiments, a combination therapy described herein (e.g., a combination therapy including a compound of Formula (A) from those listed in FIG. 1 and one or more compounds of Formula (C) listed in FIG. 2 is more effective against a particular HCV genotype than the standard of care (such as genotype 1, 2, 3, 4, 5 and/or 6).

Various indicators for determining the effectiveness of a method for treating an HCV infection are known to those skilled in the art. Example of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease, stasis in liver function, improvement in liver function, reduction in one or more markers of liver dysfunction, including alanine transaminase, aspartate transaminase, total bilirubin, conjugated bilirubin, gamma glutamyl transpeptidase, and/or other indicator of disease response. Similarly, successful therapy with a combination therapy described herein (e.g., a combination therapy including a compound of Formula (A) selected from those listed in FIG. 1 and one or more compounds of Formula (C) listed in FIG. 2, or pharmaceutically acceptable salts, hydrates, or solvates of the aforementioned compounds) can reduce the incidence of liver cancer in HCV patients.

In some embodiments, an amount of a combination as described herein of a compound of Formula (A) and one or more compounds selected from those of FIG. 2 (Formula (C)), or pharmaceutically acceptable salts, hydrates, or solvates of the aforementioned compounds, is an amount that is effective to reduce viral titers to undetectable levels, to about 100 to about 500, to about 50 to about 100, to about 10 to about 50, or to about 15 to about 25 international units/mL serum. In some embodiments, an amount of a combination as described herein of a compound of Formula (A) and one or more compounds selected from those of FIG. 2 (Formula (C)), or pharmaceutically acceptable salts, hydrates, or solvates of the aforementioned compounds, is an amount that is effective to reduce viral load compared to the viral load before administration of a combination as described herein of a compound of Formula (A) and one or more compounds selected from those of FIG. 2 (Formula (C)), or pharmaceutically acceptable salts, hydrates, or solvates of the aforementioned compounds. For example, wherein the viral load is measured before administration of a combination as described herein of a compound of Formula (A) and one or more compounds selected from those of FIG. 2 (Formula (C)), or pharmaceutically acceptable salts, hydrates, or solvates of the aforementioned compounds, and again after completion of the treatment regime with a combination as described herein of a compound of Formula (A) and one or more compounds selected from those of FIG. 2 (Formula (C)), or pharmaceutically acceptable salts, hydrates, or solvates of the aforementioned compounds (for example, 1 month after completion). In some embodiments, an amount of a combination as described herein of a compound of Formula (A) and one or more compounds selected from those of FIG. 2 (Formula (C)), or pharmaceutically acceptable salts, hydrates, or solvates of the aforementioned compounds, can be an amount that is effective to reduce viral load to lower than about 100 genome copies/mL serum. In some embodiments, an amount of a combination as described herein of a compound of Formula (A) and one or more compounds selected from those of FIG. 2 (Formula (C)), or pharmaceutically acceptable salts, hydrates, or solvates of the aforementioned compounds, is an amount that is effective to achieve a reduction in viral titer in the serum of the subject in the range of about 1.5-log to about a 2.5-log reduction, about a 3-log to about a 4-log reduction, or a greater than about S-log reduction compared to the viral load before administration of a combination as described herein of a compound of Formula (A) and one or more compounds selected from those of FIG. 2 (Formula (C)), or pharmaceutically acceptable salts, hydrates, or solvates of the aforementioned compounds. For example, the viral load can be measured before administration of a combination as described herein of a compound of Formula (A) and one or more compounds selected from those of FIG. 2 (Formula (C)), or pharmaceutically acceptable salts, hydrates, or solvates of the aforementioned compounds, and again after completion of the treatment regime with a combination as described herein of a compound of Formula (A) and one or more compounds selected from those of FIG. 2 (Formula (C)), or pharmaceutically acceptable salts, hydrates, or solvates of the aforementioned compounds (for example, 1 month after completion).

In some embodiments, a combination as described herein of a compound of Formula (A) and one or more compounds selected from those of FIG. 2 (Formula (C)), or pharmaceutically acceptable salts, hydrates, or solvates of the aforementioned compounds, can result in at least a 1, 2, 3, 4, 5, 10, 15, 20, 25, 50, 75, 100-fold or more reduction in the replication of HCV relative to pre-treatment levels in a subject, as determined after completion of the treatment regime (for example 1 month after completion). In some embodiments, a combination as described herein of a compound of Formula (A) and one or more compounds selected from those of FIG. 2 (Formula (C)), or pharmaceutically acceptable salts, hydrates, or solvates of the aforementioned compounds, can result in a reduction of the replication of HCV relative to pre-treatment levels in the range of about 2 to about 5 fold, about 10 to about 20 fold, about 15 to about 40 fold, or about 50 to about 100 fold. In some embodiments, a combination as described herein of a compound of Formula (A) and one or more compounds selected from those of FIG. 2 (Formula (C)), or pharmaceutically acceptable salts, hydrates, or solvates of the aforementioned compounds, can result in a reduction of HCV replication in the range of 1 to 1.5 log, 1.5 log to 2 log, 2 log to 2.5 log, 2.5 to 3 log, 3 log to 3.5 log or 3.5 to 4 log more reduction of HCV replication compared to the reduction of HCV replication achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an amount of a combination as described herein of a compound of Formula (A) and one or more compounds selected from those of FIG. 2 (Formula (C)), or pharmaceutically acceptable salts, hydrates, or solvates of the aforementioned compounds, is an amount that is effective to achieve a sustained viral response, for example, non-detectable or substantially non-detectable HCV RNA (e.g., less than about 500, less than about 400, less than about 200, or less than about 100 genome copies per milliliter serum) is found in the subject's serum for a period of at least about one month, at least about two months, at least about three months, at least about four months, at least about five months, or at least about six months following cessation of therapy.

In some embodiments, an amount of a combination as described herein of a compound of Formula (A) and one or more compounds selected from those of FIG. 2 (Formula (C)), or pharmaceutically acceptable salts, hydrates, or solvates of the aforementioned compounds, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers includes measuring the levels of serum alanine aminotransferase (ALT), asparatate aminotransferacse (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a combination as described herein of a compound of Formula (A) and one or more compounds selected from those of FIG. 2 (Formula (C)), or pharmaceutically acceptable salts, hydrates, or solvates of the aforementioned compounds is an amount effective to reduce ALT, AST, ALP, GGT and/or TBIL levels to within what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a combination as described herein of a compound of Formula (A) and one or more compounds selected from those of FIG. 2 (Formula (C)), or pharmaceutically acceptable salts, hydrates, or solvates of the aforementioned compounds, can be administered to a treatment failure subject suffering from HCV. In some embodiments, a combination as described herein of a compound of Formula (A) and one or more compounds selected from those of FIG. 2 (Formula (C)), or pharmaceutically acceptable salts, hydrates, or solvates of the aforementioned compounds, can be administered to a non-responder subject suffering from HCV. In some embodiments, a combination as described herein of a compound of Formula (A) and one or more compounds selected from those of FIG. 2 (Formula (C)), or pharmaceutically acceptable salts, hydrates, or solvates of the aforementioned compounds, can be administered to a relapsed subject suffering from HCV.

After a period of time, infectious agents can develop resistance to one or more therapeutic compounds. The term "resistance" as used herein refers to a viral strain displaying a delayed, lessened and/or null response to a therapeutic compound(s). For example, after treatment with an antiviral agent, the viral load of a subject infected with a resistant virus may be reduced to a lesser degree compared to the amount in viral load reduction exhibited by a subject infected with a non-resistant strain. In some embodiments, a combination as described herein of a compound of Formula (A) and one or more compounds selected from those of FIG. 2 (Formula (C)), or pharmaceutically acceptable salts, hydrates, or solvates of the aforementioned compounds, can be administered to a subject infected with an HCV strain that is resistant to one or more different anti-HCV agents. In some embodiments, development of resistant HCV strains is delayed when patients are treated with a combination as described herein of a compound of Formula (A) and one or more compounds selected from those of FIG. 2 (Formula (C)), or pharmaceutically acceptable salts, hydrates, or solvates of the aforementioned compounds, or a pharmaceutically acceptable salt thereof, compared to the development of HCV strains resistant to other HCV drugs.

In some embodiments, an effective amount of a combination as described herein of a compound of Formula (A) and one or more compounds selected from those of FIG. 2 (Formula (C)), or pharmaceutically acceptable salts, hydrates, or solvates of the aforementioned compounds, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a combination as described herein of a compound of Formula (A) and one or more compounds selected from those of FIG. 2 (Formula (C)), or pharmaceutically acceptable salts, hydrates, or solvates of the aforementioned compounds, can be provided to a subject that is hypersensitive to interferon or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a combination as described herein of a compound of Formula (A) and one or more compounds selected from those of FIG. 2 (Formula (C)), or pharmaceutically acceptable salts, hydrates, or solvates of the aforementioned compounds, can be administered to a subject experiencing viral load rebound, or can prevent such viral load rebound when used to treat the subject.

The standard of care for treating HCV has been associated with several side effects (adverse events). In some embodiments, a combination as described herein of a compound of Formula (A) and one or more compounds selected from those of FIG. 2 (Formula (C)), or pharmaceutically acceptable salts, hydrates, or solvates of the aforementioned compounds, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a combination as described herein of a compound of Formula (A) and one or more compounds selected from those of FIG. 2 (Formula (C)), or pharmaceutically acceptable salts, hydrates, or solvates of the aforementioned compounds, can be provided to a subject that discontinued an HCV therapy because of one or more adverse effects or side effects associated with one or more other HCV agents.

Table A provides some embodiments of a combination as described herein of a compound of Formula (A) and one or more compounds selected from those of FIG. 2 (Formula (C)), or pharmaceutically acceptable salts, hydrates, or solvates of the aforementioned compounds, compared to the standard of care. Examples include the following: in some embodiments, a combination as described herein of a combination as described herein of a compound of Formula (A) and one or more compounds selected from those of FIG. 2 (Formula (C)), or pharmaceutically acceptable salts, hydrates, or solvates of the aforementioned compounds, results in a percentage of non-responders that is 10% less than the percentage of non-responders receiving the standard of care; in some embodiments, a combination as described herein of a compound of Formula (A) and one or more compounds selected from those of FIG. 2 (Formula (C)), or pharmaceutically acceptable salts, hydrates, or solvates of the aforementioned compounds, results in a number of side effects that is in the range of about 10% to about 30% less than compared to the number of side effects experienced by a subject receiving the standard of care; and in some embodiments, a combination as described herein of a compound of Formula (A) and one or more compounds selected from those of FIG. 2 (Formula (C)), or pharmaceutically acceptable salts, hydrates, or solvates of the aforementioned compounds, results in a severity of a side effect (such as one of those described herein) that is 25% less than compared to the severity of the same side effect experienced by a subject receiving the standard of care. Methods of quantifying the severity of a side effect are known to those skilled in the art.

TABLE A

| Percentage of non-responders | Percentage of relapsers | Percentage of resistance | Percentage of viral load rebound | Number of side effects | Severity of side effects |
| --- | --- | --- | --- | --- | --- |
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "effective amount" is used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a combination therapy including a combination as described herein of a compound of Formula (A) and one or more compounds selected from those of FIG. 2 (Formula (C)), or pharmaceutically acceptable salts, hydrates, or solvates of the aforementioned compounds, can be administered less frequently compared to the frequency of administration of an agent within the standard of care. In some embodiments, a combination therapy including a combination as described herein of a compound of Formula (A) and one or more compounds selected from those of FIG. 2 (Formula (C)) can be administered one time per day. For example, a combination therapy including a combination as described herein of a compound of Formula (A) and one or more compounds selected from those of FIG. 2 (Formula (C)), or pharmaceutically acceptable salts, hydrates, or solvates of the aforementioned compounds, can be administered one time per day to a subject suffering from an HCV infection. In some embodiments, the total time of the treatment regime with a combination therapy including a combination as described herein of a compound of Formula (A) and one or more compounds selected from those of FIG. 2 (Formula (C)), or pharmaceutically acceptable salts, hydrates, or solvates of the aforementioned compounds, can be less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

Some embodiments relate to combination therapies that can include an effective amount of a combination of compounds described herein (e.g., a combination as described herein of a compound of Formula (A) and one or more compounds selected from those listed in FIG. 2 (Formula (C)), or pharmaceutically acceptable salts, hydrates, or solvates of the aforementioned compounds), and one or more pharmaceutically acceptable carriers, diluents, excipients or combinations thereof.

Combination therapies contemplated include use of a compound of Formula (A) selected from those listed in FIG. 1 and two different compounds (e.g., HCV protease inhibitors, nucleoside HCV polymerase inhibitors, non-nucleoside HCV polymerase inhibitors, NS5A inhibitors, or other antivirals) selected from those listed in FIG. 2 (Formula (C)), or pharmaceutically acceptable salts, hydrates, or solvates of the aforementioned compounds.

The dosing amount(s) and dosing schedule(s) when using a combination as described herein of a compound of Formula (A) and one or more compounds selected from those listed in FIG. 2 (Formula (C)), or pharmaceutically acceptable salts, hydrates, or solvates of the aforementioned compounds, are within the knowledge of those skilled in the art, using effective amounts and dosing protocols as described herein.

The order of administration of a combination of a compound of Formula (A) and one or more agent(s) (such as those listed in FIG. 2), or pharmaceutically acceptable salts, hydrates, or solvates of the aforementioned compounds, can vary. In some embodiments, a compound of Formula (A), or a pharmaceutically acceptable salt, hydrate, or solvate thereof, can be administered prior to all compounds (such as those listed in FIG. 2), or pharmaceutically acceptable salts, hydrates, or solvates of the aforementioned compounds. In other embodiments, a compound of Formula (A), or a pharmaceutically acceptable salt, hydrate, or solvate thereof, can be administered prior to at least one compound (such as those listed in FIG. 2), or pharmaceutically acceptable salts, hydrates, or solvates of the aforementioned compounds. In still other embodiments, a compound of Formula (A), or a pharmaceutically acceptable salt, hydrate, or solvate thereof, can be administered concomitantly with one or more compound(s) (such as those listed in FIG. 2), or pharmaceutically acceptable salts, hydrates, or solvates of the aforementioned compounds. In yet still other embodiments, a compound of Formula (A), or a pharmaceutically acceptable salt, hydrate, or solvate thereof, can be administered subsequent to the administration of at least one agents (such as those listed in FIG. 2), or pharmaceutically acceptable salts, hydrates, or solvates of the aforementioned compounds. In some embodiments, a compound of Formula (A), or a pharmaceutically acceptable salt, hydrate, or solvate thereof, can be administered subsequent to the administration of all other agents (such as those listed in FIG. 2), or pharmaceutically acceptable salts, hydrates, or solvates of the aforementioned compounds.

In some embodiments, the combination of a compound of Formula (A) with one or more compounds selected from FIG. 2 (Formula (C)), or pharmaceutically acceptable salts, hydrates, or solvates of the aforementioned compounds, can result in an additive effect. In some embodiments, the combination of a compound of Formula (A), with one or more compounds selected from FIG. 2 (Formula (C)), or pharmaceutically acceptable salts, hydrates, or solvates of the aforementioned compounds, can result in a synergistic effect. In some embodiments, the combination of a compound of Formula (A), with one or more compounds selected from FIG. 2 (Formula (C)), or pharmaceutically acceptable salts, hydrates, or solvates of the aforementioned compounds, can result in a strongly synergistic effect. In some embodiments, the combination of a compound of Formula (A), with one or more compounds selected from FIG. 2 (Formula (C)), or pharmaceutically acceptable salts, hydrates, or solvates of the aforementioned compounds, is not antagonistic.

As used herein, the term "antagonistic" means that the activity of the combination of compounds is less compared to the sum of the activities of the compounds in combination when the activity of each compound is determined individually (i.e., as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compounds in the combination when the activity of each compound is determined individually.

A potential advantage of utilizing a combination of a compound of Formula (A) with one or more compounds selected from FIG. 2 (Formula (C)), or pharmaceutically acceptable salts, hydrates, or solvates of the aforementioned compounds, may be a reduction in the required amount(s) of the compound(s) that is effective in treating a disease condition disclosed herein (for example, HCV), as compared to the amount required to achieve same therapeutic result when the compound(s) from FIG. 2 (Formula (c)), or pharmaceutically acceptable salts, hydrates, or solvates of the aforementioned compounds, is administered without a compound of Formula (A), or a pharmaceutically acceptable salt, hydrate, or solvate thereof. For example, the amount of the agent from FIG. 2 (Formula (C)), or pharmaceutically acceptable salts, hydrates, or solvates of the aforementioned compounds, can be less compared to the amount of the compound from FIG. 2 (Formula (C)), or pharmaceutically acceptable salts, hydrates, or solvates of the aforementioned compounds, needed to achieve the same viral load reduction when administered as a monotherapy. Another potential advantage of utilizing a compound of Formula (A), or pharmaceutically acceptable salts, hydrates, or solvates of the aforementioned compounds, with one or more compounds selected from FIG. 2 (Formula (C)), or pharmaceutically acceptable salts, hydrates, or solvates of the aforementioned compounds, is that the use of two or more compounds having different mechanisms of action can create a higher barrier to the development of resistant viral strains compared to the barrier when a compound is administered as monotherapy.

Additional advantages of utilizing a combination as described herein of a combination of a compound Formula (A) with one or more compounds selected from FIG. 2 (Formula (C)), or pharmaceutically acceptable salts, hydrates, or solvates of the aforementioned compounds, may include little to no cross resistance between a combination of a compound of Formula (A), or a pharmaceutically acceptable salt, hydrate, or solvate thereof, and the one or more compounds selected from FIG. 2 (Formula (C)), or pharmaceutically acceptable salts, hydrates, or solvates of the aforementioned compounds; different routes for elimination of a combination of a compound of Formula (A), or a pharmaceutically acceptable salt, hydrate, or solvate thereof, and the one or more compounds selected from FIG. 2 (Formula (C)), or pharmaceutically acceptable salts, hydrates, or solvates of the aforementioned compounds; little to no overlapping toxicities between a combination of a compound of Formula (A), or a pharmaceutically acceptable salt, hydrate, or solvate thereof, and the one or more compounds selected from FIG. 2 (Formula (C)), or pharmaceutically acceptable salts, hydrates, or solvates of the aforementioned compounds; little to no significant effects on cytochrome P450; and/or little to no pharmacokinetic interactions between a combination of a compound of Formula (A), or a pharmaceutically acceptable salt, hydrate, or solvate thereof, and the one or more compounds selected from FIG. 2 (Formula (C)), or pharmaceutically acceptable salts, hydrates, or solvates of the aforementioned compounds.

A non-limiting list of example combinations of a compound of Formula (A) selected from those of FIG. 1 and one compound selected from those of FIG. 2 (Formula (C)) is provided in Table B. Provided in Table C is a non-limiting list of example combinations of a compound of Formula (A) selected from those of FIG. 1 and two different compounds selected from those of FIG. 2 (Formula (C)).

Compound 1002 encompasses a mixture of diastereomers including Compound 1003 and Compound 1004, each of which are depicted below.

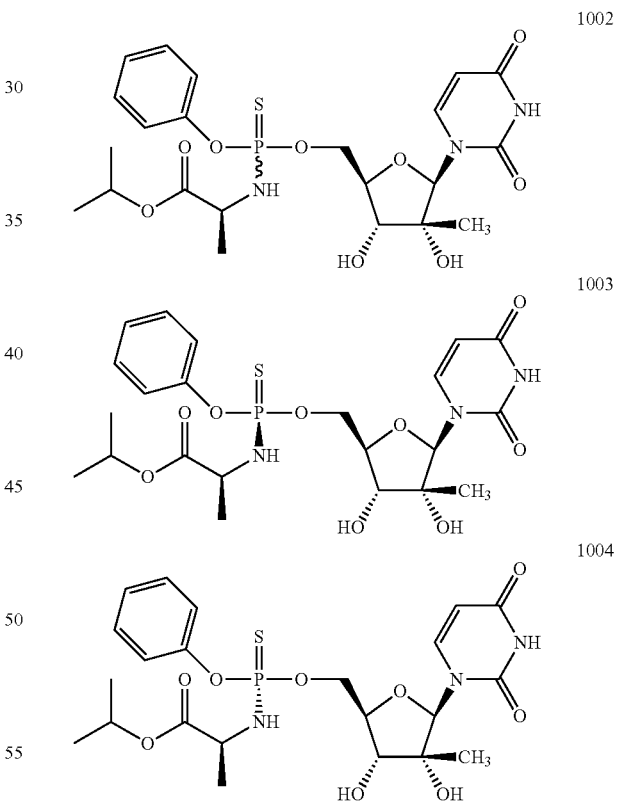

Each numbered compound in Tables B and C has a corresponding name and/or structure provided in FIGS. 1 and 2. The numbered compounds in Tables B and C include pharmaceutically acceptable salts, hydrates, and solvates of the compounds and pharmaceutical compositions containing the compounds or a pharmaceutically acceptable salt, hydrate, or solvate thereof. For example, 1001 includes the compound corresponding to 1001, pharmaceutically acceptable salts, hydrates, and solvates of the aforementioned compound, and pharmaceutical compositions that include compound 1001, or pharmaceutically acceptable salts, hydrates, or solvates of the aforementioned compound. The combinations exemplified in Table B are designated by the Formula A:C, which represents a combination of a compound of Formula (A) with a compound of Formula (C). The combinations exemplified in Table C are designated by the Formula A:C:C, which represents a combination of a compound of Formula (A) with a first compound of Formula (C) with a second compound of Formula (C). For example, the combination designated as 1001:3001:3002 in Table C represents a combination of compound 1001 with compound 3001 and with compound 3002, including pharmaceutically acceptable salts, hydrates, and solvates of compound 1001, 3001, and/or 3002, and pharmaceutical compositions including compound 1001, 3001, and/or 3002 (including pharmaceutical compositions that include pharmaceutically acceptable salts, hydrates, and solvates of compound 1001, 3001, and/or 3002). Thus, the combination designated as 1001:3001:3002 in Table C represents the combination of

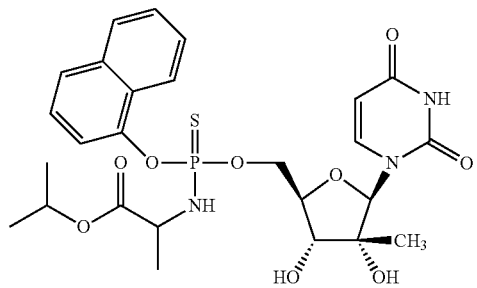 [SMILES: CC(C)OC(=O)C(C)NP(=S)(OC[C@H]1O[C@@H](n2ccc(=O)[nH]c2=O)[C@](C)(O)[C@@H]1O)Oc1cccc2ccccc12]

(compound 1001, as shown in FIG. 1), Telaprevir (compound 3001, as shown in FIG. 2), and MK-5172 (compound 3002, as shown in FIG. 2) including pharmaceutically acceptable salts, hydrates, and solvates of compounds 1001, 3001, and/or 3002, and pharmaceutical compositions including compounds 1001, 3001, and/or 3002 (including pharmaceutical compositions that include pharmaceutically acceptable salts, hydrates, and solvates of compound 1001, 3001, and/or 3002). Each of the combinations provided in Tables B and C can be used with one, two, three or more compounds described herein. In some embodiments, including embodiments described herein, the combination of compounds can be used to treat, ameliorate and/or inhibit a virus and/or a viral infection, wherein the virus can be HCV and the viral infection can be an HCV viral infection.

---

Lengthy table referenced here

US09012427-20150421-T00001

Please refer to the end of the specification for access instructions.

---

Lengthy table referenced here

US09012427-20150421-T00002

Please refer to the end of the specification for access instructions.

---

Additional examples of compounds that can be used in combination with a compound described herein (for example, a compound of Formula (A), or a pharmaceutically acceptable salt thereof) include those described in the following: WO 99/07733 (Boehringer Ingelheim), WO 99/07734 (Boehringer Ingelheim), WO 00/09558 (Boehringer Ingelheim), WO 00/09543 (Boehringer Ingelheim), WO 00/59929 (Boehringer Ingelheim), WO 02/060926 (BMS), WO 2006/039488 (Vertex), WO 2005/077969 (Vertex), WO 2005/035525 (Vertex), WO 2005/028502 (Vertex), WO 2005/007681 (Vertex), WO 2004/092162 (Vertex), WO 2004/092161 (Vertex), WO 2003/035060 (Vertex), WO 03/087092 (Vertex), WO 02/18369 (Vertex), WO 98/17679 (Vertex), WO 03/010140 (Boehringer Ingelheim), WO 03/026587 (Bristol Myers Squibb), WO 02/100846 A1, WO 02/100851 A2, WO 01/85172 AI (GSK), WO 02/098424 A1 (GSK), WO 00/06529 (Merck), WO 02/06246 A1 (Merck), WO 01/47883 (Japan Tobacco), WO 03/000254 (Japan Tobacco), EP 1 256 628 A2 (Agouron), WO 01/90121 A2 (Idenix), WO 02/069903 A2 (Biocryst Pharmaceuticals Inc.), WO 02/057287 A2 (Merck/Isis), WO 02/057425 A2 (Merck/Isis), WO 2010/117635, WO 2010/117977, WO 2010/117704, WO 2010/1200621, WO 2010/096302, WO 2010/017401, WO 2009/102633, WO 2009/102568, WO 2009/102325, WO 2009/102318, WO 2009/020828, WO 2009/020825, WO 2008/144380, WO 2008/021936, WO 2008/021928, WO 2008/021927, WO 2006/133326, WO 2004/014852, WO 2004/014313, WO 2010/096777, WO 2010/065681, WO 2010/065668, WO 2010/065674, WO 2010/062821, WO 2010/099527, WO 2010/096462, WO 2010/091413, WO 2010/094077, WO 2010/111483, WO 2010/120935, WO 2010/126967, WO 2010/132538, WO 2010/122162 and WO 2006/019831 (PTC therapeutics), wherein all the aforementioned are hereby incorporated by reference for the limited purpose of the chemical structures and chemical compounds disclosed therein.

Further examples of compounds that can be used in combination with a compound described herein (for example, a compound of Formula (A), or a pharmaceutically acceptable salt thereof) include the following: a NS3/4A inhibitor, a viral serine protease inhibitor, a viral helicase inhibitor, an immunomodulating agent, an antioxidant agent, an antibacterial agent, a therapeutic vaccine, a hepatoprotectant agent, an antisense agent, an inhibitor of HCV NS2/3 protease and an inhibitor of internal ribosome entry site (IRES). Examples of the aforementioned compounds along with other compounds that can be used in combination with a compound of Formula (A), or a pharmaceutically acceptable salt thereof, include, but are not limited to, the following: R1626, R1479 (Roche), MK-0608 (Merck), R1656, (Roche-Pharmasset), Valopicitabine (Idenix), JTK-002/003, JTK-109 (Japan Tobacco), GS-7977(Gilead), EDP-239 (Enanta), PPI-1301 (Presido Pharmaceuticals), (Gao M. et al. Nature, 465, 96-100 (2010)), INX-189 (Inhibitex), JTK-853 (Japan Tobacco), RO-5303253 Hoffmann-La Roche), IDX-184 (Idenix Pharmaceuticals), class I interferons (such as alpha-interferons, beta-interferons, delta-interferons, omega-interferons, tau-inteferons, x-interferons, consensus interferons and asialo-interferons), class II interferons (such as gamma-interferons), pegylated interferons, interferon alpha 1A, interferon alpha 1B, interferon alpha 2A, and interferon alpha 2B, thalidomide, IL-2; hematopoietins, IMPDH inhibitors (for example, Merimepodib (Vertex Pharmaceuticals Inc.)), natural interferon (such as OMNIFERON, Viragen and SUMIFERON, Sumitomo, and a blend of natural interferons), natural interferon alpha (ALFERON, Hemispherx Biopharma, Inc.), interferon alpha n1 from lymphblastoid cells (WELLFERON, Glaxo Wellcome), oral alpha interferon, Peg-interferon, Peg-interferon alpha 2a (PEGASYS, Roche), recombinant interferon alpha 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), synthetic thymosin alpha 1 (ZADAXIN, SciClone Pharmaceuticals Inc.), an antisense agent (for example, ISIS-14803), SCH-6, ITMN-B (InterMune), GS9132 (Gilead), ISIS-14803 (ISIS Pharmaceuticals), ribavirin, amantadine, merimepodib, Levovirin, Viramidine, maxamine, silybum marianum, interleukine-12, amantadine, ribozyme, thymosin, N-acetyl cysteine and cyclosporin.

EXAMPLES

Additional embodiments are disclosed in further detail in the following examples, which are not in any way intended to limit the scope of the claims.

Example 1

HCV Replicon Assay

Dual Combination and Triple Combination

Materials

Macrocyclic NS3-4A protease inhibitor, Compound 3013, was purchased from Acme Bioscience Inc. (Palo Alto, Calif.). Compound 1004 and NS5A inhibitor, Compound 3043, were synthesized at Vertex Pharmaceuticals Incorporated (Cambridge, Mass.). DMEM (cat number 10313-021), 200 mM L-glutamine (catalog number 25030-081), 100× non-essential amino acids (catalog number 11140-050), and PenStrep (catalog number 15140) were purchased from Invitrogen Corporation (Carlsbad, Calif.). Fetal bovine serume (catalog number F4135) and DMSO (catalog number D2650) was purchased from Sigma Chemical Company (St Louis, Mo.). Cell Titer Glo® luminescent cell viability assay reagent (catalog number G7573) and luciferase assay kit (catalog number E4550) were purchased from Promega Corporation (Madison, Wis.). Ingenio electroporation solution (catalog number 50117) was purchased from Minis Bio LLC (Madison, Wis.).

Compound Handling

All compounds were dissolved in 100% DMSO (dimethyl sulfoxide) to a stock concentration of 10 mM and stored at −20° C. Serial 2-fold or 3-fold dilution series of compounds were prepared in 100% DMSO at 400-fold of the final concentration to be used in cell culture experiments that would result in a final DMSO concentration of 0.25% in growth medium.

In Vitro Combination Assay

Drug combination studies were carried out using the transient replicon system. On day one, in vitro transcribed RNA of a genotype 1b replicon carrying the firefly luciferase reporter was transfected into Huh-7-ET-cured cells using Minis transfection reagent. (Lohmann V et al., "Replication of subgenomic hepatitis C virus RNAs in a hepatoma cell line" *Science* (1999) 285(5424):110-113, which is hereby incorporated by reference in its entirety) Ten thousand transfected cells were cultured in complete DMEM medium [DMEM medium supplemented with 2 mM L-glutamine, 1× non-essential amino acids, 10% heat inactivated FBS and PenStrep (100 units/mL penicillin and 100 ug/mL streptomycin)] in the central 60 wells of 96-well, flat bottom, tissue culture treated plates and cultured at 37° C./5% $CO_2$ humidified incubator for 24 h. The next day, compounds were serially diluted (2× or 3× dilution series) in 100% DMSO, mixed together in a checkerboard fashion and added to cells, and the plates were returned to the incubator for an additional 72 h. Each concentration combination of two compounds was tested in 4 replicates for effect on HCV replicon replication. The highest concentration of compounds tested was ~10 to 20-fold the replicon $IC_{50}$ value such that the $IC_{50}$ concentration appeared in the middle of the dilution series. At the end of the incubation, cells from one set of the plates were lysed and the luciferase activity was measured using a luciferase assay kit. In experiments involving three compounds combinations, the two compound combination experiments were conducted at different constant concentrations of the third compound.

Data Analysis

The effects of dual combinations were evaluated using the Bliss independence model. (Greco et al., "The search for synergy: a critical review from a response surface perspective" *Pharmacol. Rev.* (1995) 47(2):331-385, which is hereby incorporated by reference in its entirety) The experimental data (RLU) was analyzed by using MacSynergy, a three-dimensional analytical method developed by Prichard and Shipman. (Prichard et al., "A three-dimensional model to analyze drug-drug interactions" *Antiviral Res.* (1990) 14(4-5):181-205, which is hereby incorporated by reference in its entirety) In this model, the theoretical additive effect is calculated from the dose-response curves of individual compounds by the equation $Z=X+Y(1-X)$, where X and Y represent the inhibition produced by drug 1 alone and drug 2 alone, respectively, and Z represents the effect produced by the combination of drug 1 and drug 2. The theoretical additive surface is subtracted from the actual experimental surface, resulting in a surface that would appear as a horizontal plane at 0% inhibition if the combination is merely additive. Any peak above this plane would indicate synergy, whereas any depression below it would indicate antagonism. The 95% confidence intervals for the experimental dose-response surface are used to evaluate the data statistically. The volume of the peak or depression is calculated to quantify the overall synergy or antagonism produced.

A separate set of plates (3 replicates) was set up concurrently to determine the effect of combinations of varying concentrations of the two compounds on cell viability using the Cell Titer Glo® luminescent reagent from Promega that measures cellular ATP as a function of cell viability.

Combination Therapies

The effect of drug combinations on HCV replication was evaluated in a genotype 1b transient replicon system using the MacSynergy program as described herein. Independent experiments were conducted and the number of experiments for each combination is indicated in Table 1A by "n." A dual combination of Compound 1004 with Compound 3013 or Compound 3043 showed minor synergy, and a dual combination of Compound 3013 with Compound 3043 showed minor synergy. In the triple combination of Compound 1004, Compound 3013 and Compound 3043, an interaction ranging from additive to moderate synergy was observed. No significant cytotoxicity was observed at the concentrations tested in these studies.

| Compound | | |
|---|---|---|
| Compound 1004 | | 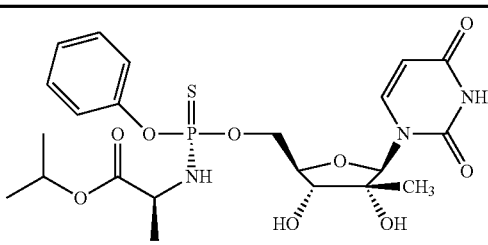 |
| Compound 3013 | TMC-435 TMC-435350 | 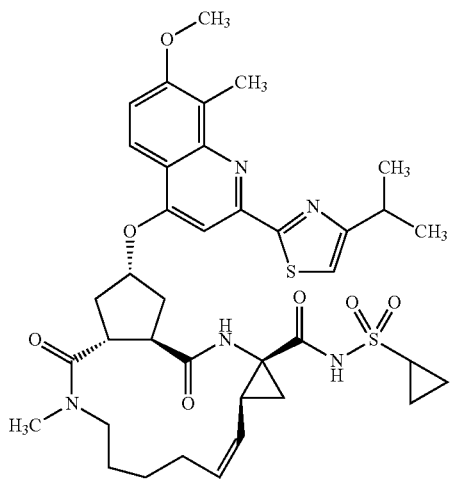 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C] |
| Compound 3043 | BMS-790052 BMS052 S1482 Daclatasvir | 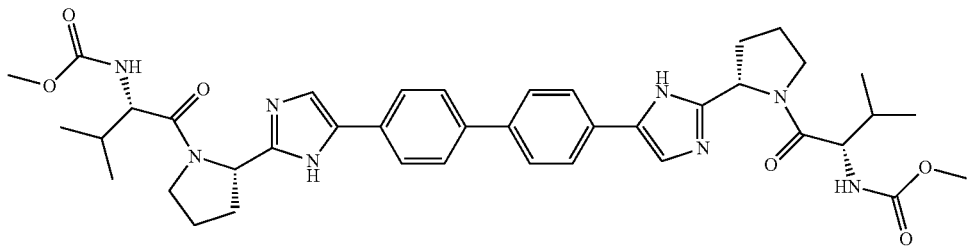 |

TABLE 1A

Summary of results of in vitro combination studies

| Compound 1[a] | Compound 2[a] | Compound 3[a] | Synergy Volume[b] (95% CI) | Antagonism Volume[b] (95% CI) | Combination Result* |
|---|---|---|---|---|---|
| 1004 | 3013 | — | 14.58 27.85 65.61 | −0.41 −0.25 −3.68 | Minor Synergy (n = 3) |
| 1004 | 3043 | — | 7.73 90.08 37.58 | −0.06 −3.21 −0.08 | Minor Synergy (n = 3) |
| 3043 | 3013 | — | 73.18 19.15 | −5.43 −9.59 | Minor Synergy (n = 2) |
| 3043 | 3013 | 1004 (80.6 nM) | 52.44 64.74 | −0.36 −17.31 | Minor Synergy (n = 2) |
| 3043 | 3013 | 1004 (161.2 nM) | 82.83 61.01 | −0.46 −0.28 | Moderate Synergy (n = 2) |
| 3043 | 3013 | 1004 (322.3 nM) | 38.5 80.76 | −0.49 −0.51 | Moderate Synergy (n = 2) |
| 3043 | 3013 | 1004 (644.6 nM) | 22.47 104.66 | −0.46 −0.54 | Moderate Synergy (n = 2) |
| 3043 | 3013 | 1004 (1289.2 nM) | 0.06 12.27 | −26.57 −5.26 | Additive (n = 2) |
| 3043 | 3013 | 1004 (2578.5 nM) | 5.96 | −6.99 | Additive (n = 1) |

[a]Individual IC$_{50}$ values: Compound 1004 = 357 nM, n = 3; Compound 3013 = 2.1 nM, n = 3 and Compound 3043 = 0.0114 nM, n = 3.
[b]Where multiple experiments were performed each individual determination is listed.
*Combination result is defined based on the MacSynergy volume: −25-25 → additive, 25-50 → minor synergy, 50-100 → moderate synergy, >100 → strong synergy Example 2

HCV Replicon Assay

Triple Combination

Materials

HCV inhibitor Compound 1002 provided by Alios BioPharma, Inc. (San Francisco, Calif. 94080, USA). Compound 3001 (TVR), and Compound 3028 were synthesized at Vertex (Cambridge, USA). DMEM (cat number 10313-021), 200 mM L-glutamine (catalog number 25030-081), 100× non-essential amino acids (catalog number 11140-050), PenStrep (catalog number 15140) and G418 (catalog number 11811-023) were purchased from Invitrogen Corporation (Carlsbad, Calif.). Fetal bovine serum (catalog number F4135) and DMSO (catalog number D2650) was purchased from Sigma Chemical Company (St Louis, Mo.). Cell Titer Glo® luminescent cell viability assay reagent (catalog number G7573) and luciferase assay kit (catalog number E4550) were purchased from Promega Corporation (Madison, Wis.).

Compound 1002
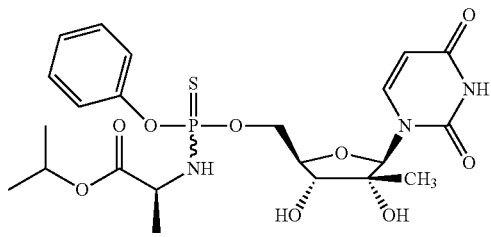 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

Compound 3001  Telaprevir VX-950
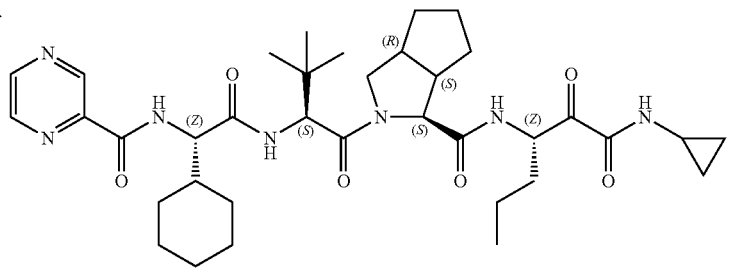

Compound 3028  VX-222 S1480 VCH-222
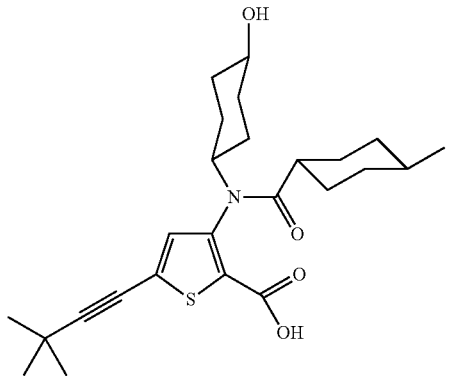 [SMILES: CC1CCC(C(=O)N(c2cc(C#CC(C)(C)C)sc2C(=O)O)C2CCC(O)CC2)CC1]

Compound Handling

For in vitro virological assays, Compound 1002, was dissolved in 100% DMSO (dimethyl sulfoxide) to a stock concentration of 10 mM and stored at −20° C. Serial 2-fold or 3-fold dilution series of compounds were prepared in 100% DMSO at 100 to 200-fold the final concentration to be used in cell culture experiments that would result in a final DMSO concentration of ≤0.5% in growth medium.

Cell Viability Assays

Cytotoxicity of compounds against HCV replicon cells (transient or stable replicons cells) was evaluated in separate assays that were run concurrently with the 3-day or 2-day replicon assays and the effect of compounds on cell viability was determined using the Cell Titer Glo® luminescence reagent that measures cellular ATP as a function of cell viability. The resulting RLU values were analyzed applying the 4-parametric curve fitting method using the SoftMaxPro software (Molecular Devices, Inc., Sunnyvale Calif.) to derive $CC_{50}$ values (concentration of compound that results in a 2-fold reduction in cell viability). Each compound concentration was tested at least in duplicates and the average value of replicates was used for curve fitting.

In Vitro Combination Assays

Drug combination studies were carried out using the transient replicon system described above. On day one, in vitro transcribed RNA of GT 1b WT replicon carrying the firefly luciferase reporter was transfected into Huh-7-ET-cured cells using the Mirus transfection reagent. Approximately, ten thousand transfected cells were cultured in complete DMEM medium [DMEM medium supplemented with 2 mM L-glutamine, 1× non-essential amino acids, 10% heat inactivated fetal bovine serum and PenStrep (100 units/mL penicillin and 100 μg/mL streptomycin)] in central 60 wells of 96-well, flat bottom, tissue culture treated plates and cultured at 37° C./5% $CO_2$ humidified incubator for 24 h. The next day, compounds were serially diluted (2× or 3× dilution series) in 100% DMSO, mixed together in a checkerboard fashion and added to cells, and the plates were returned to the incubator for an additional 72 h. Each concentration combination of two compounds was tested in 4 replicates for effect on HCV replicon replication. The highest concentration of compounds tested was ~10 to 20-fold the replicon $IC_{50}$ value such that the $IC_{50}$ concentration appeared in the middle of the dilution series. At the end of the incubation period, the cells from one set of plates were lysed and the luciferase activity was measured using a luciferase assay kit.

The effects of drug-drug combinations were evaluated using the Bliss independence model (Greco W R, Bravo G, Parsons J C. The search for synergy: a critical review from a response surface perspective. *Pharmacol Rev.* 1995. 47(2): 331-385). The experimental data (RLU) were analyzed by using MacSynergy, a three-dimensional analytical method developed by Prichard and Shipman (Prichard M N and Shipman C Jr.). A three-dimensional model to analyze drug-drug interactions. *Antiviral Res* 1990. 14(4-5): 181-205). In this model, the theoretical additive effect is calculated from the dose-response curves of individual compounds by the equation Z=X+Y(1−X), where X and Y represent the inhibition produced by drug 1 alone and drug 2 alone, respectively and Z represents the effect produced by the combination of drug 1 and drug 2. The theoretical additive surface is subtracted from the actual experimental surface, resulting in a surface that would appear as a horizontal plane at 0% inhibition if the combination is merely additive. Any peak above this plane would indicate synergy, whereas any depression below it would indicate antagonism. The 95% confidence intervals for the experimental dose-response surface are used to evaluate the data statistically. The volume of the peak or depression is calculated to quantify the overall synergy or antagonism produced.

A separate set of plates (3 replicates) were set up concurrently to determine the effect of combinations of varying concentrations of the two compounds on cell viability using the Cell Titer Glo® luminescent reagent from Promega that measures cellular ATP as a function of cell viability.

Combination Therapies

The effect of combinations of Compound 1002, Compound 3001, and Compound 3028 on HCV replication was evaluated in five independent experiments. The combination was found to have an additive effect (Table 1B). No significant cytotoxicity or antagonism was observed at the concentrations tested in these studies.

TABLE 1B

Summary of results of in vitro combination studies

| Compound Formula (A) | Compound Formula (C) | Compound Formula (C) | Synergy Volume (95% CI) | Antagonism Volume (95% CI) | Combination Result[a] |
|---|---|---|---|---|---|
| 1002 (0.112 uM) | 3001 | 3028 | 14.96 | −0.04 | Additive |
| 1002 (0.225 uM) | 3001 | 3028 | 5.41 | −0.01 | Additive |
| 1002 (0.449 uM) | 3001 | 3028 | 23.15 | −0.31 | Additive |
| 1002 (0.899 uM) | 3001 | 3028 | 18.2 | 0.0 | Additive |
| 1002 (1.80 uM) | 3001 | 3028 | 19.26 | −0.62 | Additive |

[a]Combination result is defined based on the MacSynergy volume: <25 → additive, 25-50 → minor synergy, 50-100 → moderate synergy, >100 → strong synergy Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

LENGTHY TABLES

The patent contains a lengthy table section. A copy of the table is available in electronic form from the USPTO web site (http://seqdata.uspto.gov/?pageRequest=docDetail&DocID=US09012427B2). An electronic copy of the table will also be available from the USPTO upon request and payment of the fee set forth in 37 CFR 1.19(b)(3).

What is claimed is:

1. A pharmaceutical composition comprising an effective amount of:

a compound of Formula (A), or a pharmaceutically acceptable salt, hydrate, or solvate thereof, wherein the compound of Formula (A) has the structure:

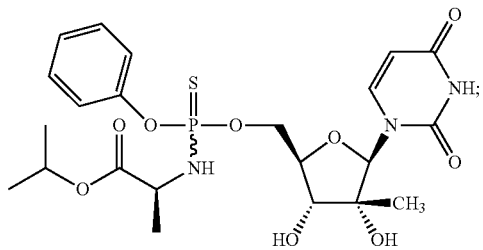 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is

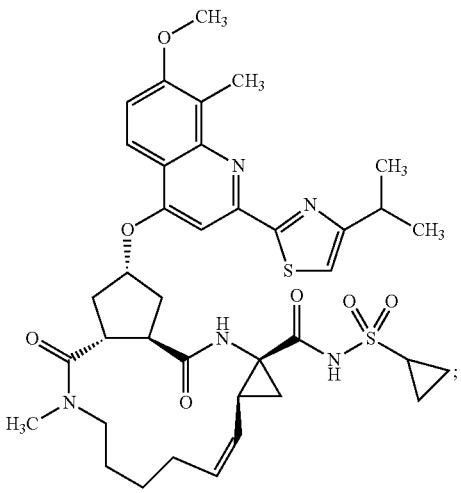 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C]

and a second compound of Formula (C), or a pharmaceutically acceptable salt, hydrate, or solvate thereof, the second compound of Formula (C) is selected from the group consisting of daclatasvir, PPI-461, ACH-2928, GS-5885, BMS-824393, ABT 267, ACH-3102, AZD-7295, IDX719, PPI-668, MK8742 and GSK805.

2. The pharmaceutical composition of claim 1, wherein the second compound of Formula (C) is daclatasvir, or a pharmaceutically acceptable salt, hydrate, or solvate thereof.

3. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

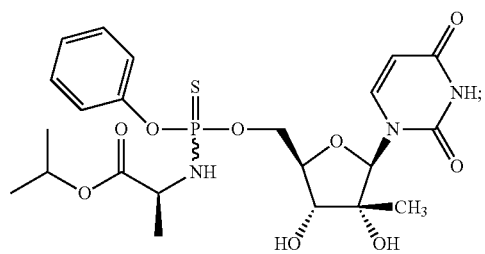 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is

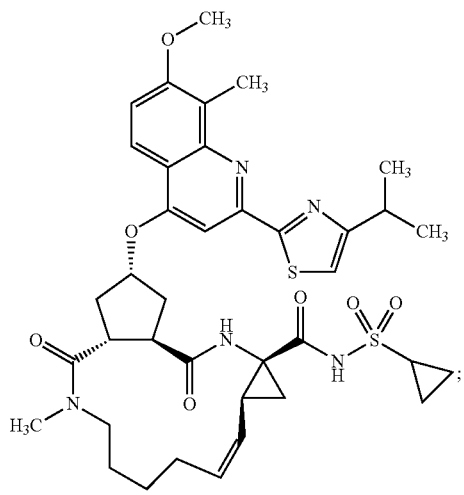 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C]

and a second compound of Formula (C), or a pharmaceutically acceptable salt, hydrate, or solvate thereof, the second compound of Formula (C) is selected from the group consisting of daclatasvir, PPI-461, ACH-2928, GS-5885, BMS-824393, ABT 267, ACH-3102, AZD-7295, IDX719, PPI-668, MK8742 and GSK805.

4. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

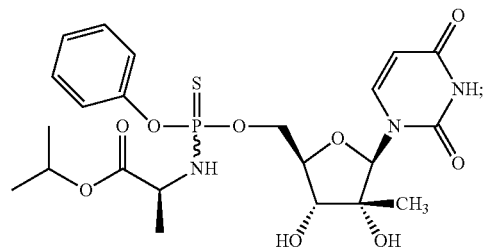 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is

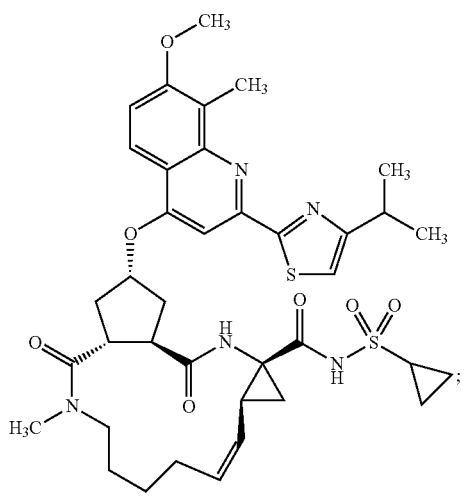 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C]

and a second compound of Formula (C), or a pharmaceutically acceptable salt, hydrate, or solvate thereof, the second compound of Formula (C) is selected from the group consisting of daclatasvir, PPI-461, ACH-2928, GS-5885, BMS-824393, ABT 267, ACH-3102, AZD-7295, IDX719, PPI-668, MK8742 and GSK805.

5. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

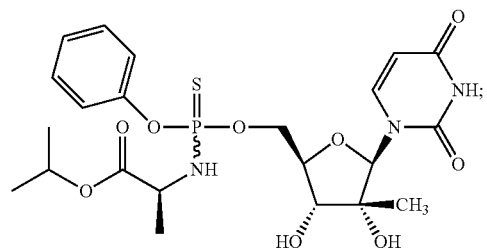 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is

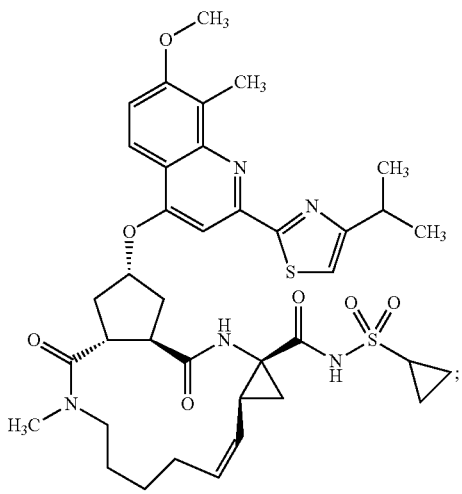 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C]

and a second compound of Formula (C), or a pharmaceutically acceptable salt, hydrate, or solvate thereof, the second compound of Formula (C) is selected from the group consisting of daclatasvir, PPI-461, ACH-2928, GS-5885, BMS-824393, ABT 267, ACH-3102, AZD-7295, IDX719, PPI-668, MK8742 and GSK805.

6. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:Exa

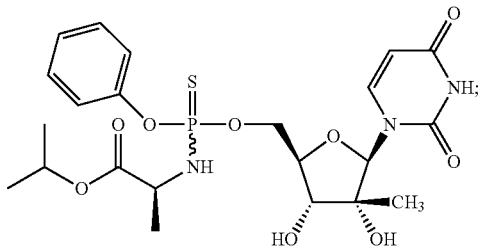 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is daclatasvir; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

7. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

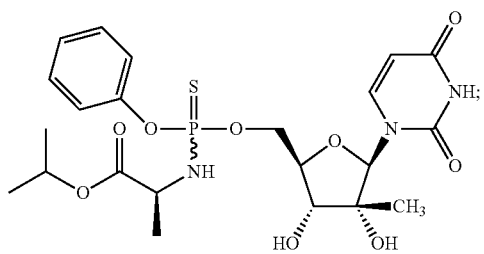 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is daclatasvir; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

8. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

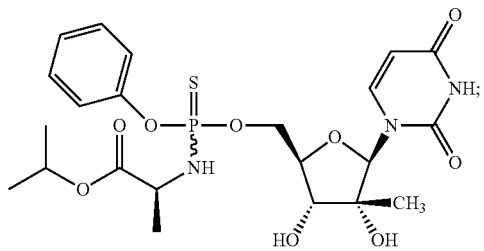 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is daclatasvir; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

9. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

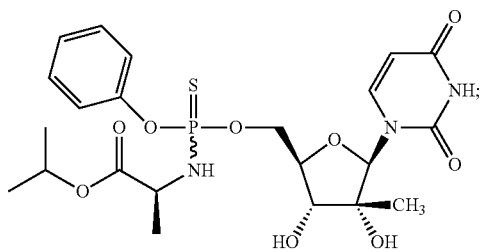 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

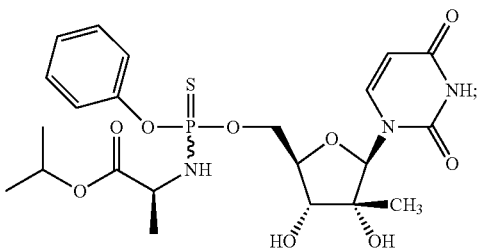 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is PPI-461; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

10. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is PPI-461; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

12. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

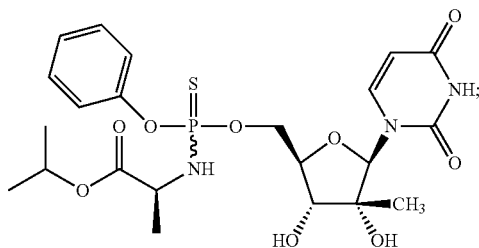 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

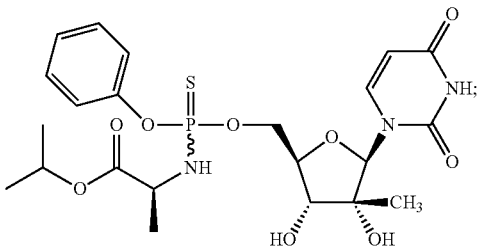 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is PPI-461; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

11. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is ACH-2928; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

13. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

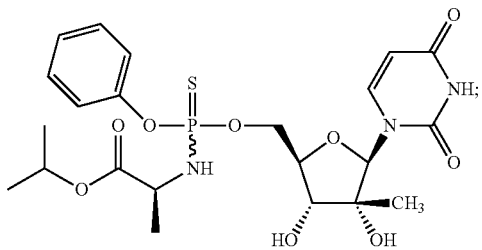 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is ACH-2928; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

14. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

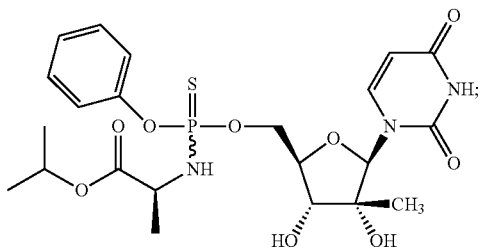 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is ACH-2928; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

15. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is GS-5885; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

16. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

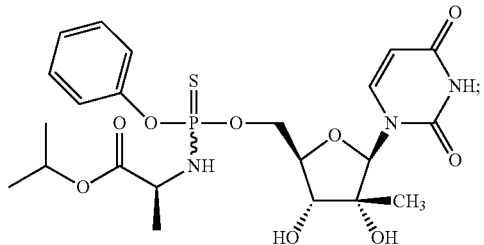 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is GS-5885; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

17. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

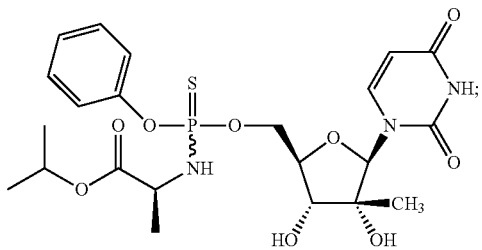 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

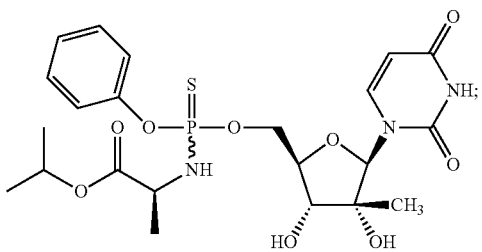 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is GS-5885; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

18. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is BMS-824393; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

20. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

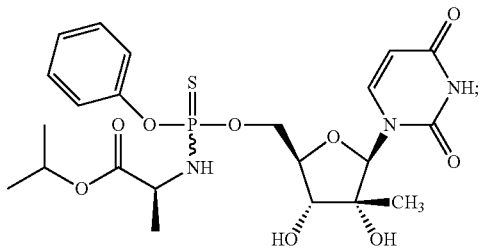 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

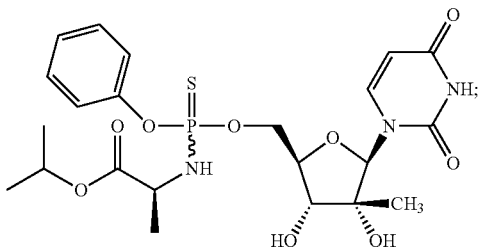 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is BMS-824393; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

19. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is BMS-824393; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

21. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

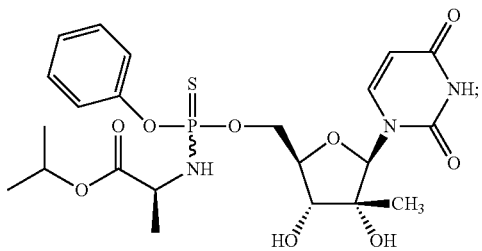 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

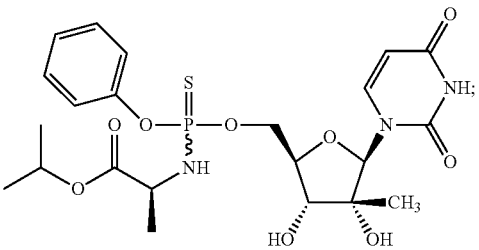 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is ABT 267; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

22. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is ABT 267; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

24. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

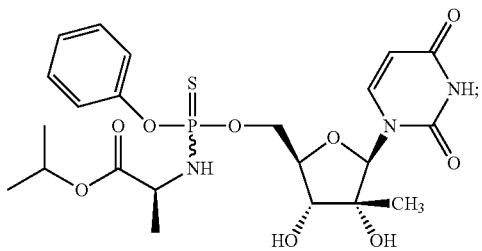 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

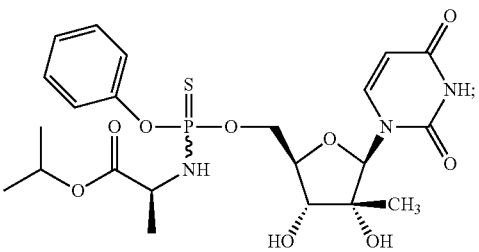 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is ABT 267; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

23. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is ACH-3102; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

25. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

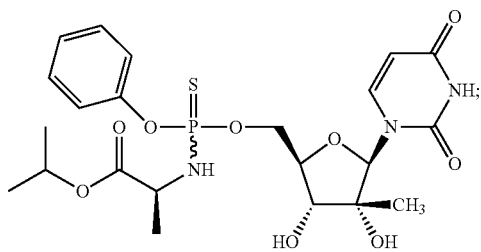 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

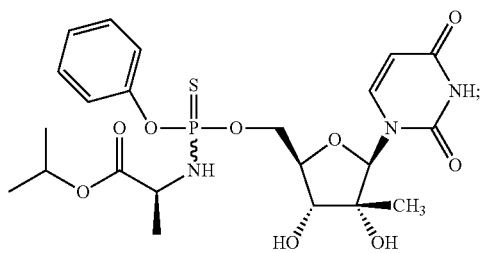

a first compound of Formula (C), or a pharmaceutically acceptable salt, hydrate, or solvate thereof, the first compound of Formula (C) is ACH-3102; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

26. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is AZD-7295; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

28. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

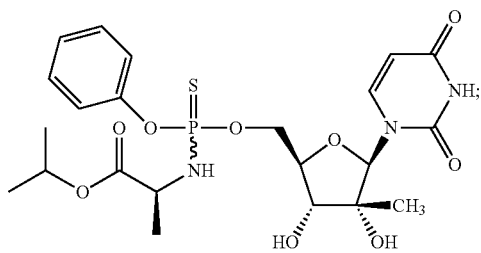 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

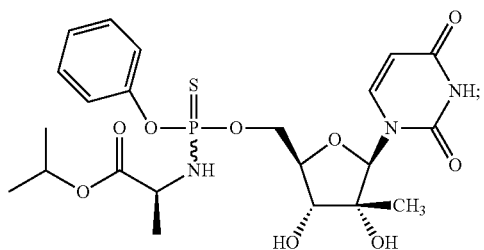 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is ACH-3102; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

27. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is AZD-7295; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

29. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

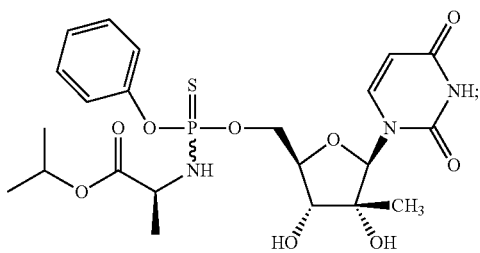 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

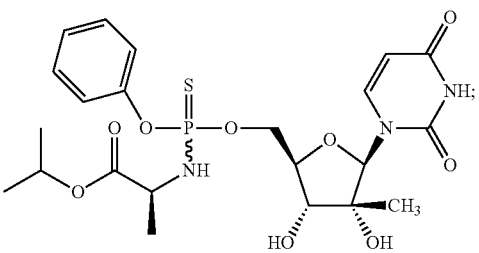 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is AZD-7295; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

30. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

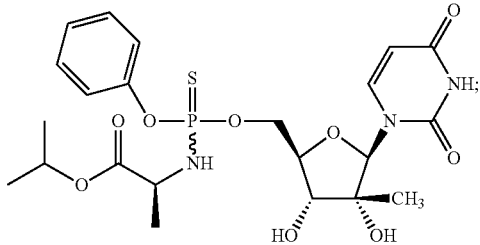 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is IDX719; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

31. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is IDX719; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

32. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

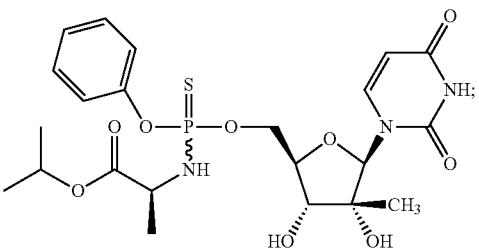 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is IDX719; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

33. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

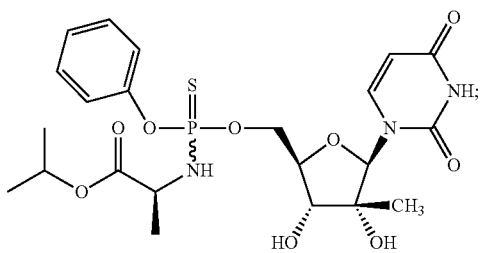 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

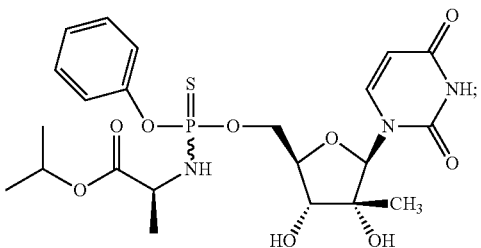 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is PPI-668; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

34. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is PPI-668; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

36. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

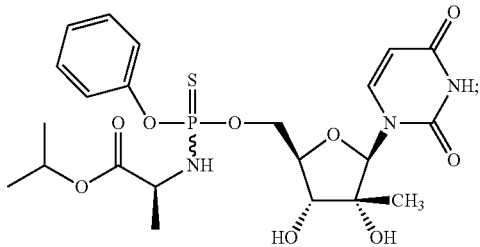 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

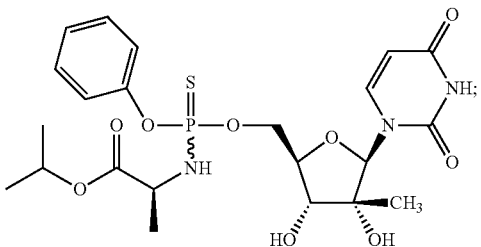 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is PPI-668; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

35. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is MK8742; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

37. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

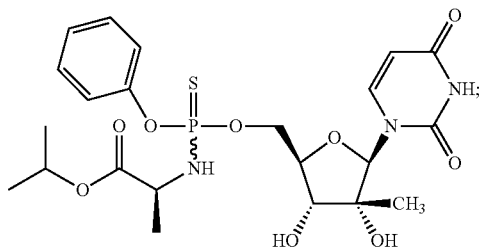 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is MK8742; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

38. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

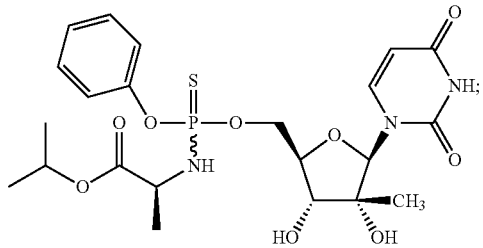 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is MK8742; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

39. A method for ameliorating or treating a hepatitis C viral infection comprising administering to a subject suffering from an hepatitis C viral infection an effective amount of a combination of:

a compound of Formula (A), or a pharmaceutically acceptable salt, hydrate, or solvate thereof, wherein the compound of Formula (A) has the structure:

a first compound of Formula (C), or a pharmaceutically acceptable salt, hydrate, or solvate thereof, the first compound of Formula (C) is GSK805; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

40. A method for inhibiting replication of a hepatitis C virus comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

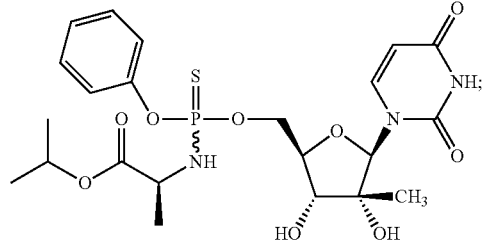 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

a first compound of Formula (C), or a pharmaceutically acceptable salt, hydrate, or solvate thereof, the first compound of Formula (C) is GSK805; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

41. A method for ameliorating or treating a hepatitis C viral infection comprising contacting a cell infected with the hepatitis C virus with an effective amount of a combination of:

a compound of Formula (A), or a pharmaceutically acceptable salt, hydrate, or solvate thereof, wherein the compound of Formula (A) has the structure:

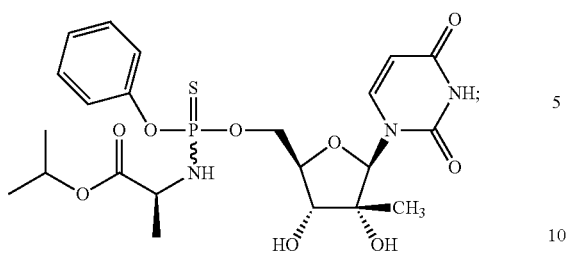

a first compound of Formula (C), or a pharmaceutically acceptable salt, hydrate, or solvate thereof, the first compound of Formula (C) is GSK805; and a second compound of Formula (C), or a pharmaceutically acceptable salt, hydrate, or solvate thereof, the second compound of Formula (C) is selected from the group consisting of telaprevir, asunaprevir, boceprevir, ACH-1625, ACH-2684, danoprevir, vaniprevir, ABT-333, setrobuvir and TMC647055.

* * * * *